United States Patent [19]
Kato et al.

[11] Patent Number: 6,123,519
[45] Date of Patent: Sep. 26, 2000

[54] DELIVERY BLOOD STORING MEMBER-EQUIPPED BLOOD RESERVOIR TANK AND BLOOD DELIVERY INSTRUMENT FOR EXTRACORPOREAL CIRCULATION CIRCUIT

[75] Inventors: Yukitoshi Kato; Mitsuaki Ogihara; Shinji Maruyama; Kazuhiko Takeuchi, all of Kanagawa-ken, Japan

[73] Assignee: Terumo Kabushiki Kaisha, Tokyo, Japan

[21] Appl. No.: 09/056,766

[22] Filed: Apr. 8, 1998

Related U.S. Application Data

[63] Continuation-in-part of application No. 08/725,228, Oct. 3, 1996, Pat. No. 5,931,646.

[30] Foreign Application Priority Data

| Oct. 3, 1995 | [JP] | Japan | 7-282474 |
| Apr. 8, 1997 | [JP] | Japan | 9-106730 |
| Dec. 1, 1997 | [JP] | Japan | 9-347012 |

[51] Int. Cl.[7] .................................... F04B 45/10
[52] U.S. Cl. ............................... 417/395; 417/384
[58] Field of Search ................... 417/395, 411, 417/384, 386, 387, 389; 604/320, 408, 321, 405, 317; 23/258.5; 422/45; 210/195.2, 188, 806, 97; 128/214 R, 276; 55/16

[56] References Cited

U.S. PATENT DOCUMENTS

| 3,007,416 | 11/1961 | Childs | 103/44 |
| 3,907,504 | 9/1975 | Hammond et al. | 23/258.5 |
| 4,014,329 | 3/1977 | Welch et al. | 128/214 R |
| 4,552,552 | 11/1985 | Polaschegg et al. | 604/4 |
| 4,599,093 | 7/1986 | Steg, Jr. | 55/16 |
| 4,610,656 | 9/1986 | Mortensen | 604/4 |
| 4,634,430 | 1/1987 | Porlaschegg | 604/141 |
| 4,897,189 | 1/1990 | Greenwood et al. | 210/195.2 |
| 5,279,550 | 1/1994 | Habib et al. | 604/38 |
| 5,411,705 | 5/1995 | Thor et al. | 422/45 |
| 5,486,099 | 1/1996 | Montoya | 417/477.13 |
| 5,512,042 | 4/1996 | Montoya et al. | 604/4 |

FOREIGN PATENT DOCUMENTS

| 0 030 760 | 6/1981 | European Pat. Off. . |
| 0 111 918 | 6/1984 | European Pat. Off. . |
| 0 309 642 | 4/1989 | European Pat. Off. . |
| 0 390 380 | 10/1990 | European Pat. Off. . |
| 0 498 740 | 8/1992 | European Pat. Off. . |
| 0 587 251 | 3/1994 | European Pat. Off. . |
| 0 766 974 | 4/1997 | European Pat. Off. . |
| 93/01858 | 2/1993 | WIPO . |

*Primary Examiner*—Charles G. Freay
*Assistant Examiner*—Robert Z. Evora
*Attorney, Agent, or Firm*—Burns, Doane, Swecker & Mathis, LLP

[57] ABSTRACT

A delivery blood storing member-equipped blood reservoir tank has a blood reservoir tank portion, and a delivery blood storing member that communicates with a blood outlet formed in the blood reservoir tank portion. The delivery blood storing member allows blood to flow out of an interior thereof when pressed from outside. The delivery blood storing member reserves amounts of blood in accordance with the height of liquid surface in the blood reservoir tank portion if the amount of blood in the blood reservoir tank portion becomes equal to or less than a predetermined value. The delivery blood storing member includes a body part that is formed from a hard material, and a flexible diaphragm whose peripheral end is fixed to the delivery blood storing member body part. The diaphragm produces substantially no self-restoring force against deformation.

41 Claims, 51 Drawing Sheets

F I G. 19
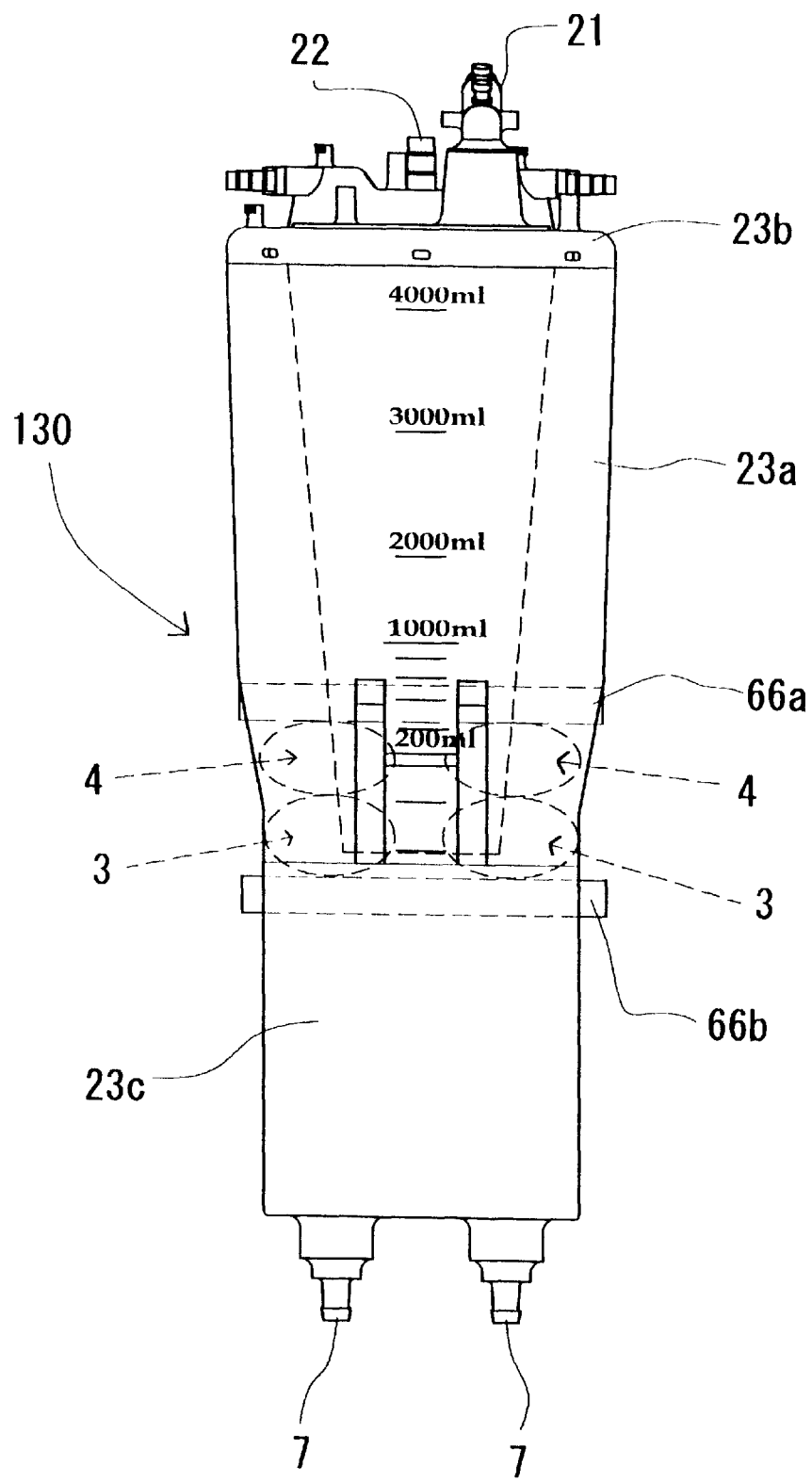

F I G. 21
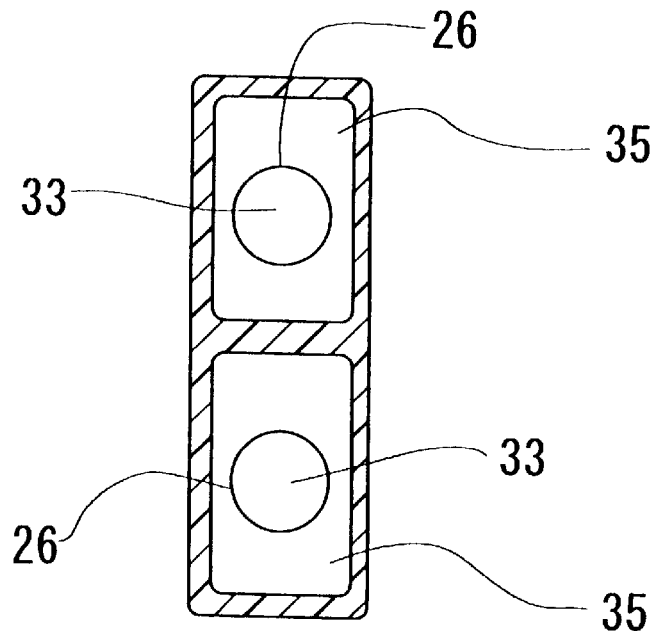
F I G. 22
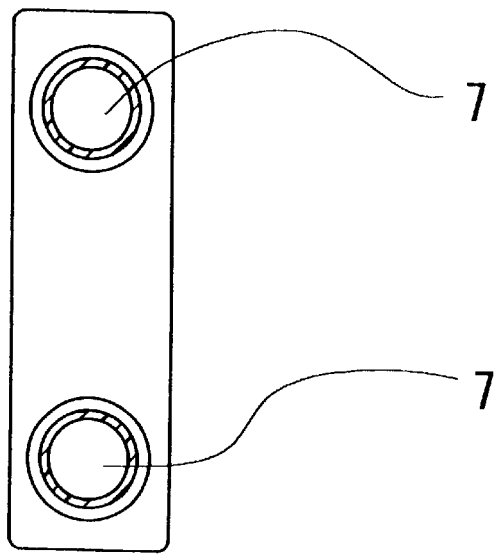

F I G. 26
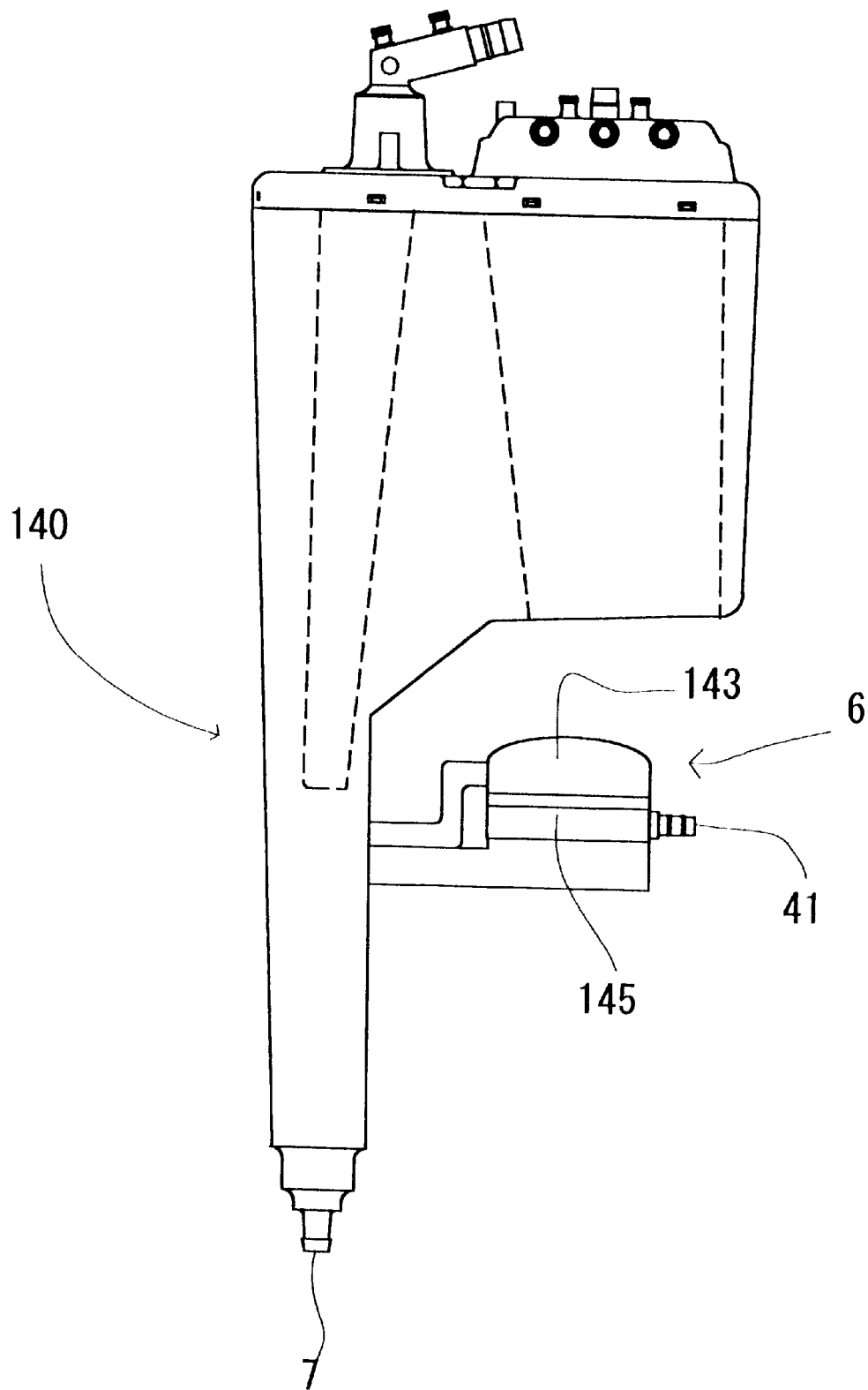

F I G. 31
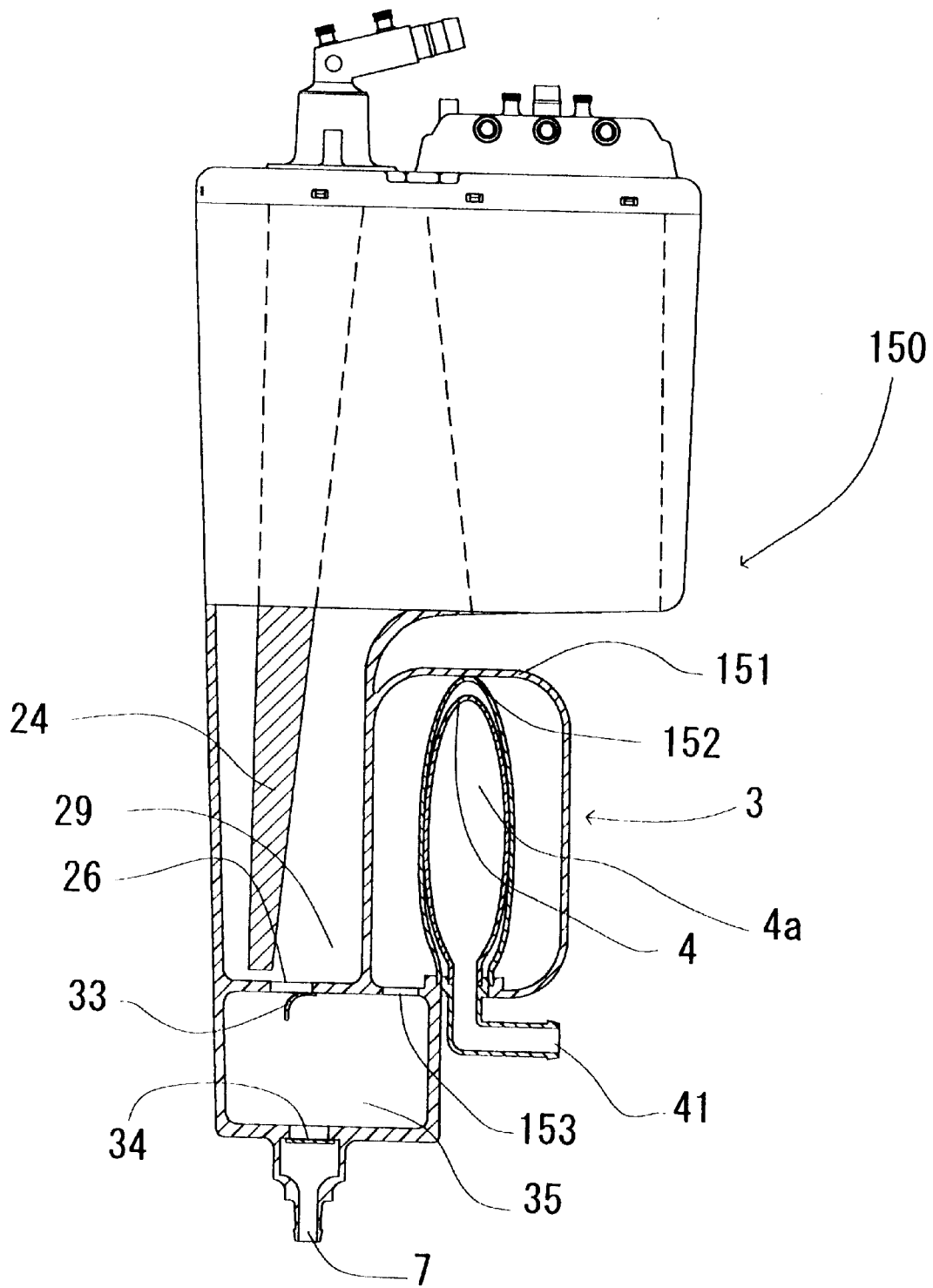

F I G. 33
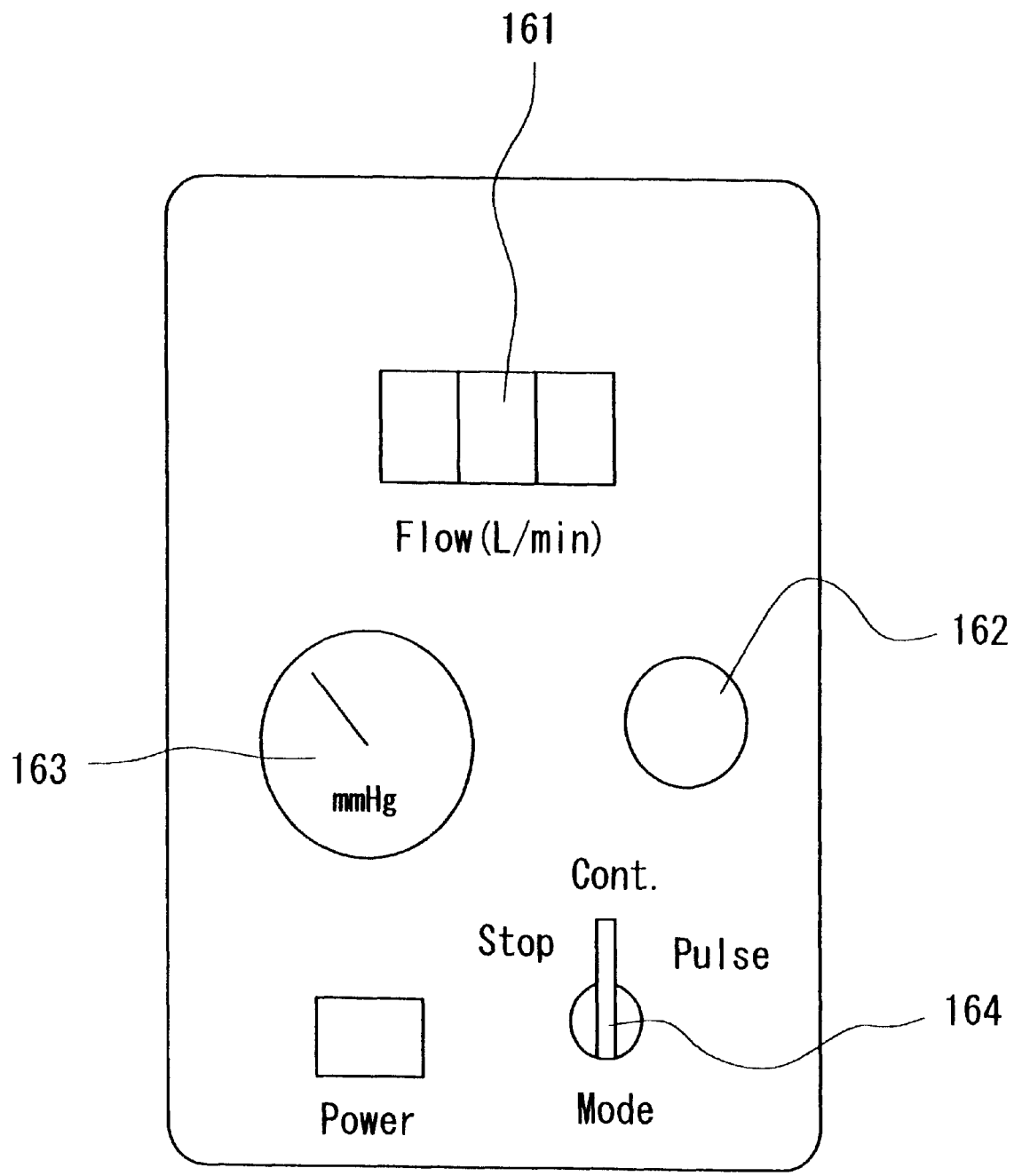

F I G. 35
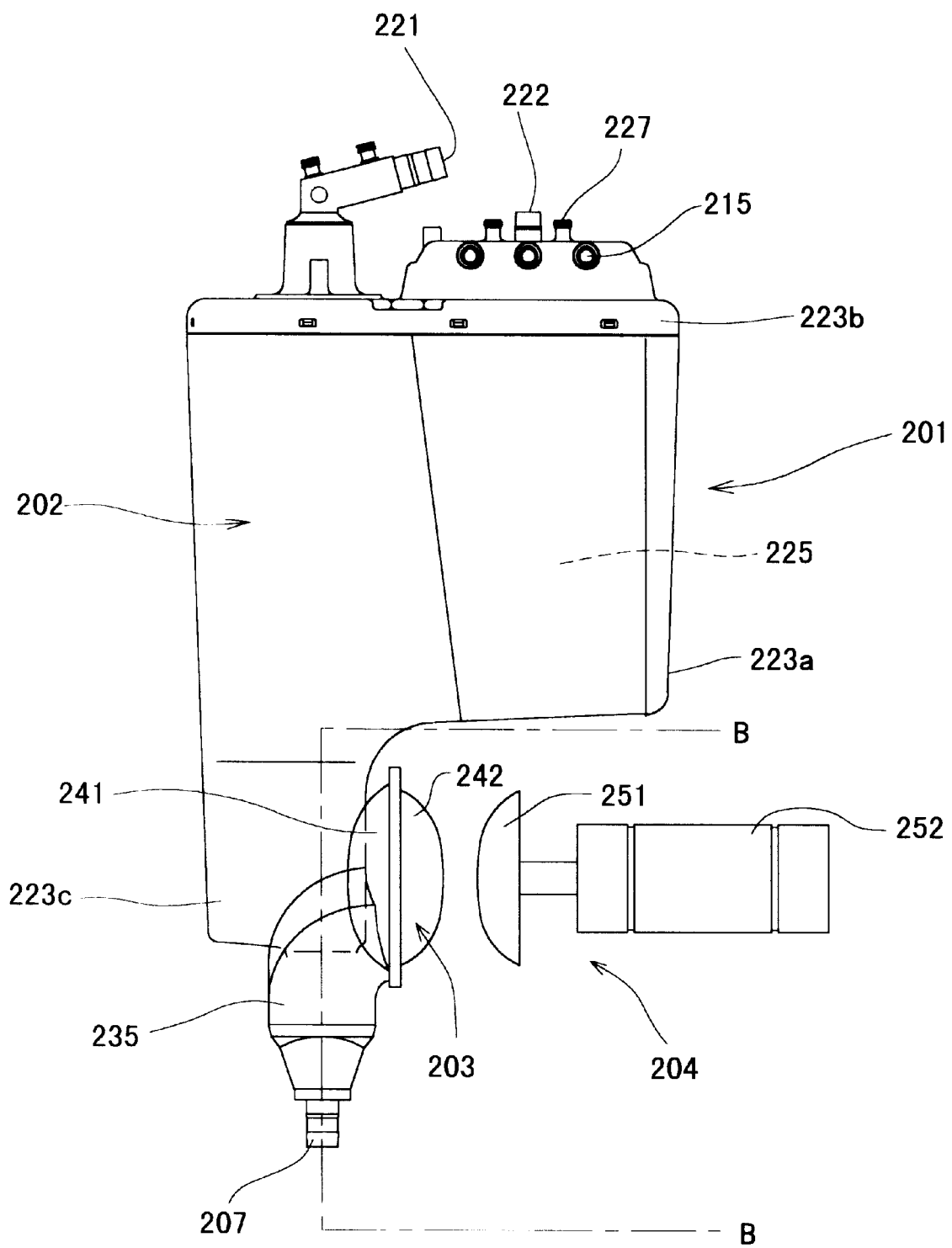

F I G. 44
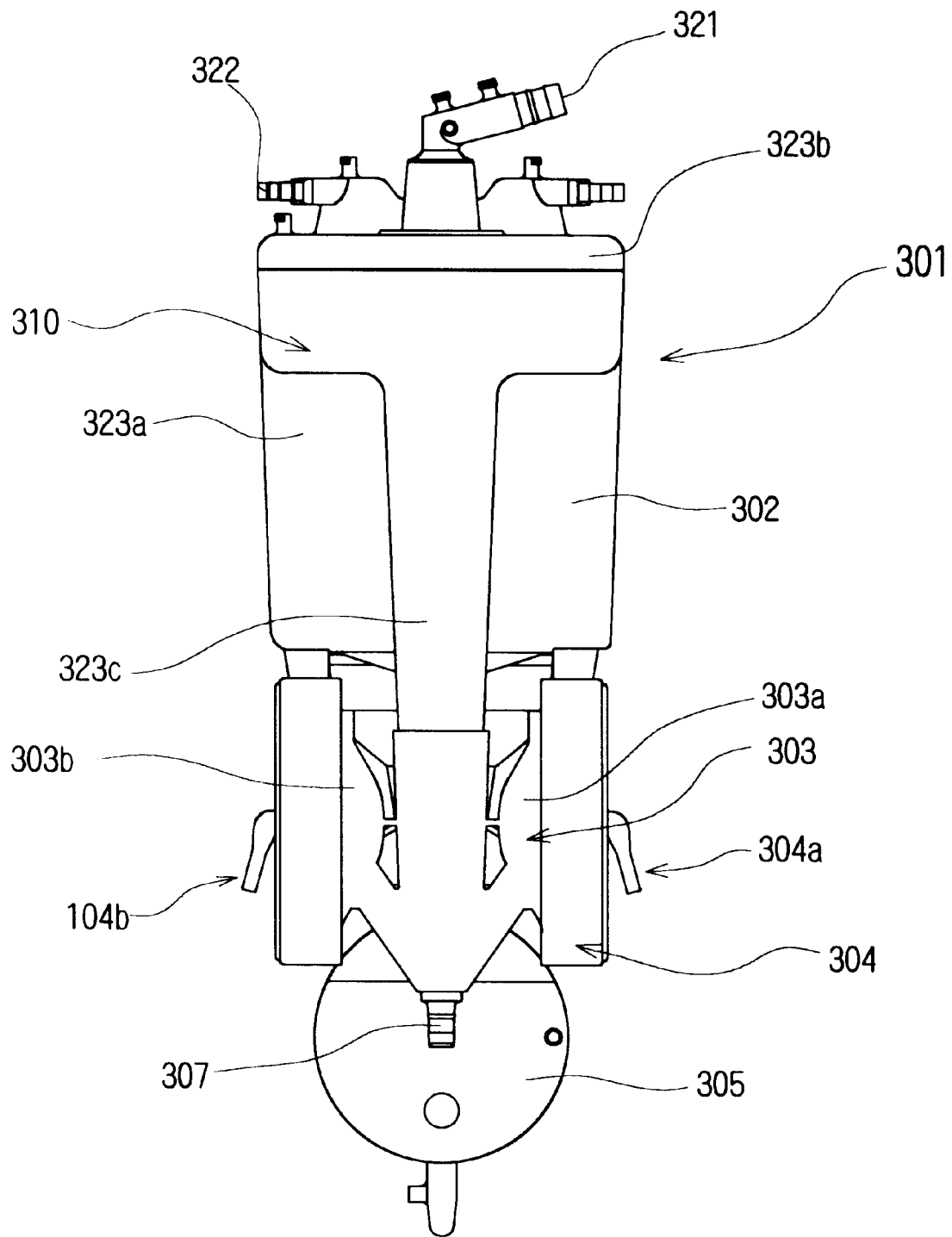

DELIVERY BLOOD STORING MEMBER-EQUIPPED BLOOD RESERVOIR TANK AND BLOOD DELIVERY INSTRUMENT FOR EXTRACORPOREAL CIRCULATION CIRCUIT

CROSS-REFERENCE TO RELATED APPLICATIONS

This application is a CIP of U.S. application Ser. No. 08/725,228, filed Oct. 3, 1996, now U.S. Pat. No. 5,931,646, the entire contents of which are incorporated herein by reference.

BACKGROUND OF THE INVENTION

The present invention relates to a delivery blood storing member-equipped blood reservoir tank that is equipped with a delivery blood storing member for temporarily storing blood and delivering stored blood in an extracorporeal blood circulation circuit for use with, for example, an artificial lung or the like. The invention also relates to a blood delivery instrument for an extracorporeal blood circulation circuit provided downstream from the blood reservoir tank.

Heart surgery often uses an extracorporeal blood circulation circuit having incorporated therein an artificial lung for removing carbon dioxide from blood and adding oxygen to blood instead of the living lung. The extracorporeal circulation circuit is to drain blood from the patient's vein, subject the blood to gas exchange in the artificial lung, and return the blood to the patient's artery. The extracorporeal circulation circuit also includes a cardiotomy line for sucking in blood from the operation area, removing foreign matter therefrom, and returning the blood.

In general, the extracorporeal circulation circuit with an artificial lung includes a blood tank for temporarily storing blood drained from the patient and a cardiotomy reservoir for filtering blood sucked from the operation area and temporarily storing the blood. The blood tank and cardiotomy reservoir serve a buffering function of adjusting the amount of blood in the circuit and maintaining a constant amount of blood returned to the patient.

There is a situation that the volume of blood in the blood tank becomes zero during extracorporeal blood circulation. If the blood feed pump continues to operate, air can be fed into the extracorporeal circulation circuit. To avoid such inconvenience, the tank is provided with a level sensor for monitoring the volume of blood in the tank. When the sensor detects that the volume of blood in the tank is below a predetermined value, the feed pump is interrupted to stop blood delivery action until the volume of blood in the blood tank is restored. The temporary interruption of blood delivery, however, is undesirable because it causes blood stagnation throughout the circuit including the artificial lung.

Therefore, there is a need to provide a delivery blood storing member-equipped blood reservoir tank capable of changing the flow of blood delivery in accordance with the amount of blood stored if the amount of blood stored in the blood reservoir tank becomes equal to or less than a predetermined value, and a blood delivery instrument for an extracorporeal blood circulation circuit disposed downstream from the blood reservoir tank.

It is a first object of the invention to provide a delivery blood storing member-equipped blood reservoir tank and a blood delivery instrument for an extracorporeal blood circulation circuit that, if the amount of blood in the blood reservoir tank becomes equal to or less than a predetermined value, are able to reserve an amount of blood in sensitive correspondence to the amount of blood stored.

It is a second object of the invention to provide a delivery blood storing member-equipped blood reservoir tank and a blood delivery instrument for an extracorporeal blood circulation circuit wherein the delivery blood storing member, which is pressed for blood delivery, is prevented from being damaged.

It is a third object of the invention to provide a blood delivery mechanism-equipped blood reservoir tank that considerably reduces the incidence of air bubbles that can be formed due to collision between a surface of the blood stored in a blood storing portion and an incoming blood current when blood delivery based on a blood delivery flow corresponding to the amount of blood stored in the blood storing portion is performed after the amount of blood in the tank blood storing portion has decreased to or below the predetermined value, and when the amount of blood stored increases back to or above the predetermined value.

It is a fourth object of the invention to provide a blood delivery mechanism-equipped blood reservoir tank that considerably reduces the damages to a delivery blood reserving portion that may be caused at the time of blood delivery.

It is a fifth object of the invention to provide a blood delivery mechanism-equipped blood reservoir tank that is equipped with a blood delivery driving unit for pressing a delivery blood reserving member, wherein even if the blood delivery driving unit is designed to press the delivery blood storing member by expansion of a blood reserving member-pressurizing portion formed of an expandable sheet material, the blood reserving member-pressurizing portion does not affect the delivery blood reserving member when the blood reserving member-pressurizing portion is not expanded, so that when the amount of blood in a blood storing portion becomes equal to or less than a predetermined value, the delivery blood reserving member reserves amounts of blood in sensitive correspondence to the amount of blood stored.

Lately, the conveyance of blood into the blood reservoir tank and the drainage of blood from a patient are often performed by a method using a suction device (negative pressure applying device) connected to the blood reservoir tank. When this device is operated, the pressure in the blood reservoir tank portion becomes negative, and the negative pressure affects the interior of the delivery blood reserving member. That is, the delivery blood reserving member becomes exposed to a negative pressure inside the member due to the operation of the suction device (negative pressure applying device), while receiving the atmospheric pressure on the outside. Therefore, the delivery blood reserving member is pressed by a differential pressure between the inside and outside pressures, so that the liquid surface-sensitive (pressure-sensitive, pre-load-sensitive) function of the delivery blood reserving member may be impeded.

It is a sixth object of the invention to provide a blood delivery mechanism-equipped blood reservoir tank that will not impede the liquid surface-sensitive (pressure-sensitive, pre-load-sensitive) function of a delivery blood reserving member even if a suction device (negative pressure applying device) is connected to the blood reservoir tank.

SUMMARY OF THE INVENTION

The aforementioned first object of the invention can be achieved by a delivery blood storing member-equipped blood reservoir tank including a blood reservoir tank portion, and a delivery blood storing member that communicates with the blood reservoir tank portion for receiving blood from the blood reservoir tank portion. The delivery blood storing member allows blood to flow out of an interior thereof when pressed from outside. The delivery blood storing member reserves an amount of blood in accordance with a height of liquid surface in the blood reservoir tank portion if an amount of blood in the blood reservoir tank portion becomes equal to or less than a predetermined value. The delivery blood storing member includes a body part of the delivery blood storing member which body part is formed from a hard material, and a flexible diaphragm whose peripheral end is fixed to the body part of the delivery blood storing member. The diaphragm produces substantially no self-restoring force against deformation.

The first object can also be achieved by a blood delivery instrument for use in an extracorporeal blood circulation circuit, which includes a connecting portion to the extracorporeal blood circulation circuit, and a delivery blood storing member that receives blood from the extracorporeal blood circulation circuit and allows blood to flow out of an interior thereof when pressed from outside. The delivery blood storing member reserves an amount of blood in accordance with a height of liquid surface in a blood reservoir tank provided in the extracorporeal blood circulation circuit or a height of liquid surface in an upstream portion of the blood delivery instrument upstream from the delivery blood storing member, if an amount of blood present in the blood reservoir tank or an amount of blood present in the upstream portion of the blood delivery instrument becomes equal to or less than a predetermined value. The delivery blood storing member includes a body part of the delivery blood storing member which body part is formed from a hard material, and a flexible diaphragm whose peripheral end is fixed to the body part of the delivery blood storing member. The diaphragm produces substantially no self-restoring force against deformation.

The second object can be achieved by a delivery blood storing member-equipped blood reservoir tank including a blood reservoir tank portion, and a delivery blood storing member that communicates with the blood reservoir tank portion for receiving blood from the blood reservoir tank portion. The delivery blood storing member allows blood to flow out of an interior thereof when pressed from outside. The delivery blood storing member reserves an amount of blood in accordance with a height of liquid surface in the blood reservoir tank portion if an amount of blood in the blood reservoir tank portion becomes equal to or less than a predetermined value. The delivery blood storing member includes a body part of the delivery blood storing member which body part is formed from a hard material, a flexible diaphragm whose peripheral end is fixed to the body part of the delivery blood storing member, and a reinforcement which covers the diaphragm and whose peripheral end is fixed to the body part of the delivery blood storing member.

The second object can also be achieved by a blood delivery instrument for use in an extracorporeal blood circulation circuit, which includes a connecting portion to the extracorporeal blood circulation circuit, and a delivery blood storing member that receives blood from the extracorporeal blood circulation circuit and allows blood to flow out of an interior thereof when pressed from outside. The delivery blood storing member reserves an amount of blood in accordance with a height of liquid surface in a blood reservoir tank provided in the extracorporeal blood circulation circuit or a height of liquid surface in an upstream portion of the blood delivery instrument upstream from the delivery blood storing member, if an amount of blood present in the blood reservoir tank or an amount of blood present in the upstream portion of the blood delivery instrument becomes equal to or less than a predetermined value. The delivery blood storing member includes a body part of the delivery blood storing member which body part is formed from a hard material, a flexible diaphragm whose peripheral end is fixed to the body part of the delivery blood storing member, and a reinforcement which covers the diaphragm and whose peripheral end is fixed to the body part of the delivery blood storing member.

The third object can be achieved by a blood delivery mechanism-equipped blood reservoir tank that includes a blood storing portion, and a blood reserving member including a blood reserving portion that communicates with the blood storing portion and receives blood from the blood storing portion. The blood reserving portion reserves an amount of blood proportional to an amount of blood stored in the blood storing portion when the amount of blood stored in the blood storing portion becomes equal to or less than a predetermined value. The blood reserving portion allows blood to flow out of an interior thereof when pressed from outside. The blood delivery mechanism-equipped blood reservoir tank further includes at least one of a bubble eliminating member and a bubble removing member that is positioned inside the blood storing portion. A lower end of the at least one of the bubble eliminating member and the bubble removing member is positioned below a lower end of the blood reserving portion of the blood reserving member.

The third object can also be achieved by a blood delivery mechanism-equipped blood reservoir tank that includes a blood storing portion, and a blood reserving member including a blood reserving portion that communicates with the blood storing portion and receives blood from the blood storing portion. The blood reserving portion reserves an amount of blood proportional to an amount of blood stored in the blood storing portion when the amount of blood stored in the blood storing portion becomes equal to or less than a predetermined value. The blood reserving portion allows blood to flow out of an interior thereof when pressed from outside. The blood delivery mechanism-equipped blood reservoir tank further includes at least one of a bubble eliminating member and a bubble removing member that is positioned inside the blood storing portion. A lower end of the at least one of the bubble eliminating member and the bubble removing member is positioned so as to remain below a surface of blood in the blood storing portion even if the surface of blood therein becomes the same level as a lower end of the blood reserving portion of the blood reserving member.

The fourth object can be achieved by a blood reservoir tank equipped with a blood delivery mechanism that includes a blood storing portion, and a blood reserving member including a blood reserving portion that communicates with the blood storing portion. The blood reserving portion reserves an amount of blood proportional to an amount of blood stored in the blood storing portion when the amount of blood stored in the blood storing portion becomes equal to or less than a predetermined value. The blood reserving portion allows blood to flow out of an interior thereof when pressed from outside. The blood delivery mechanism-equipped blood reservoir tank further includes a blood delivering drive unit that operates when blood is to be sent out of an interior of the blood reserving member. The blood reserving member includes a body portion of the blood reserving member which body portion is provided with a concavity surface portion formed from a hard material, and a flexible diaphragm retained liquid-tightly to a peripheral end portion of the concavity surface portion of the body portion of the blood reserving member. The blood delivering drive unit includes a blood reserving member-pressurizing portion formed from an expandable sheet material, and a blood delivering fluid flow port for expanding and contracting the blood reserving member-pressurizing portion. The flexible diaphragm is pressed against the concavity surface portion of the body portion of the blood reserving member, without forming any substantial bent point, when the blood reserving member-pressurizing portion is expanded.

The fifth object can be achieved by a blood reservoir tank equipped with a blood delivery mechanism that includes a blood storing portion, and a blood reserving member including a blood reserving portion that communicates with the blood storing portion. The blood reserving portion reserves an amount of blood proportional to an amount of blood stored in the blood storing portion when the amount of blood stored in the blood storing portion becomes equal to or less than a predetermined value. The blood reserving portion allows blood to flow out of an interior thereof when pressed from outside. The blood delivery mechanism further includes a blood delivering drive unit that operates when blood is to be sent out of an interior of the blood reserving member. The blood reserving member includes a body portion of the blood reserving member which body portion is formed from a hard material, and a flexible diaphragm whose peripheral portion is retained to the body portion of the blood reserving member. The blood delivering drive unit includes a blood reserving member-pressurizing portion formed from an expandable sheet material, and a blood delivering fluid flow port for expanding and contracting the blood reserving member-pressurizing portion. The blood delivery mechanism-equipped blood reservoir tank further includes a communication passage that connects a space formed between the diaphragm and the blood reserving member-pressurizing portion to the outside.

The fifth object can also be achieved by a blood reservoir tank equipped with a blood delivery mechanism that includes a blood storing portion, and a blood reserving member including a blood reserving portion that communicates with the blood storing portion. The blood reserving portion reserves an amount of blood proportional to an amount of blood stored in the blood storing portion when the amount of blood stored in the blood storing portion becomes equal to or less than a predetermined value. The blood reserving portion allows blood to flow out of an interior thereof when pressed from outside. The blood delivery mechanism further includes a blood delivering drive unit that operates when blood is to be sent out of an interior of the blood reserving member. The blood reserving member includes a body portion of the blood reserving member which body portion is formed from a hard material, and a flexible diaphragm whose peripheral portion is retained to the body portion of the blood reserving member. The blood delivering drive unit includes a blood reserving member-pressurizing portion formed from an expandable sheet material, and a blood delivering fluid flow port for expanding and contracting the blood reserving member-pressurizing portion. The blood delivery mechanism-equipped blood reservoir tank further includes a communication passage that connects a space formed between the diaphragm and the blood reserving member-pressurizing portion to an upper portion of the blood storing portion.

The sixth object can be achieved by a blood delivery mechanism-equipped blood reservoir tank that includes a blood storing portion, and a blood reserving member including a blood reserving portion that communicates with the blood storing portion. The blood reserving portion reserves an amount of blood proportional to an amount of blood stored in the blood storing portion when the amount of blood stored in the blood storing portion becomes equal to or less than a predetermined value. The blood reserving portion allows blood to flow out of an interior thereof when pressed from outside. The blood delivery mechanism-equipped blood reservoir tank further includes a blood reserving member-pressurizing portion that operates when blood is to be sent out of the blood reserving member. The blood reserving member is a soft material-made tubular body. The blood reserving member-pressurizing portion is a pump that compresses the soft material-made tubular body to force blood out of an interior of the tubular body. The blood delivery mechanism-equipped blood reservoir tank further includes a case member separating the soft material-made tubular body and a pump site that is a portion that compresses the soft material-made tubular body to force blood out of the interior of the tubular body, substantially airtightly from the outside. A communication passage connects between an interior of the case member and an upper portion of the blood storing portion.

BRIEF DESCRIPTION OF THE DRAWINGS

The foregoing and further objects, features and advantages of the present invention will become apparent from the following description of preferred embodiments with reference to the accompanying drawings, wherein like numerals are used to represent like elements and wherein:

FIGS. 18 to 24 show a blood reservoir according to a further embodiment of the invention.

FIG. 18 is a front elevational view of the reservoir.

FIG. 19 is a left side view of the reservoir.

FIG. 20 is a top view of the reservoir.

FIG. 21 is a cross section taken alone lines D—D of FIG. 18.

FIG. 22 is a cross section taken along lines E—E of FIG. 18.

FIG. 23 is a partial cross-sectional view of FIG. 18.

FIG. 24 is a schematic view for explaining the operation of the blood reservoir of FIG. 18.

FIGS. 26 to 28 show a blood reservoir according to a still further embodiment of the invention.

FIG. 26 is a front elevation of the reservoir.

FIG. 27 is a side view of the reservoir.

FIG. 28 is a partial cross-sectional view of the reservoir of FIG. 26.

FIGS. 29 to 32 show a blood reservoir according to a still further embodiment of the invention.

FIG. 29 is a front elevation of the reservoir.

FIG. 30 is a side view of the reservoir of FIG. 29.

FIG. 31 is a partial cross-sectional view of the reservoir of FIG. 29.

FIG. 32 is a partial cross-sectional view of the reservoir of FIG. 29.

FIG. 33 is a schematic view explaining a fluid feed unit for use in combination with the blood reservoir according to the invention.

FIG. 35 is a side view of the delivery blood storing member-equipped blood reservoir tank provided with a blood delivering drive unit according to the present invention.

FIG. 44 is a front elevation of a blood delivery mechanism-equipped blood reservoir tank according to an embodiment of the present invention, with an artificial lung connected.

DETAILED DESCRIPTION OF PREFERRED EMBODIMENTS

Figure 1:
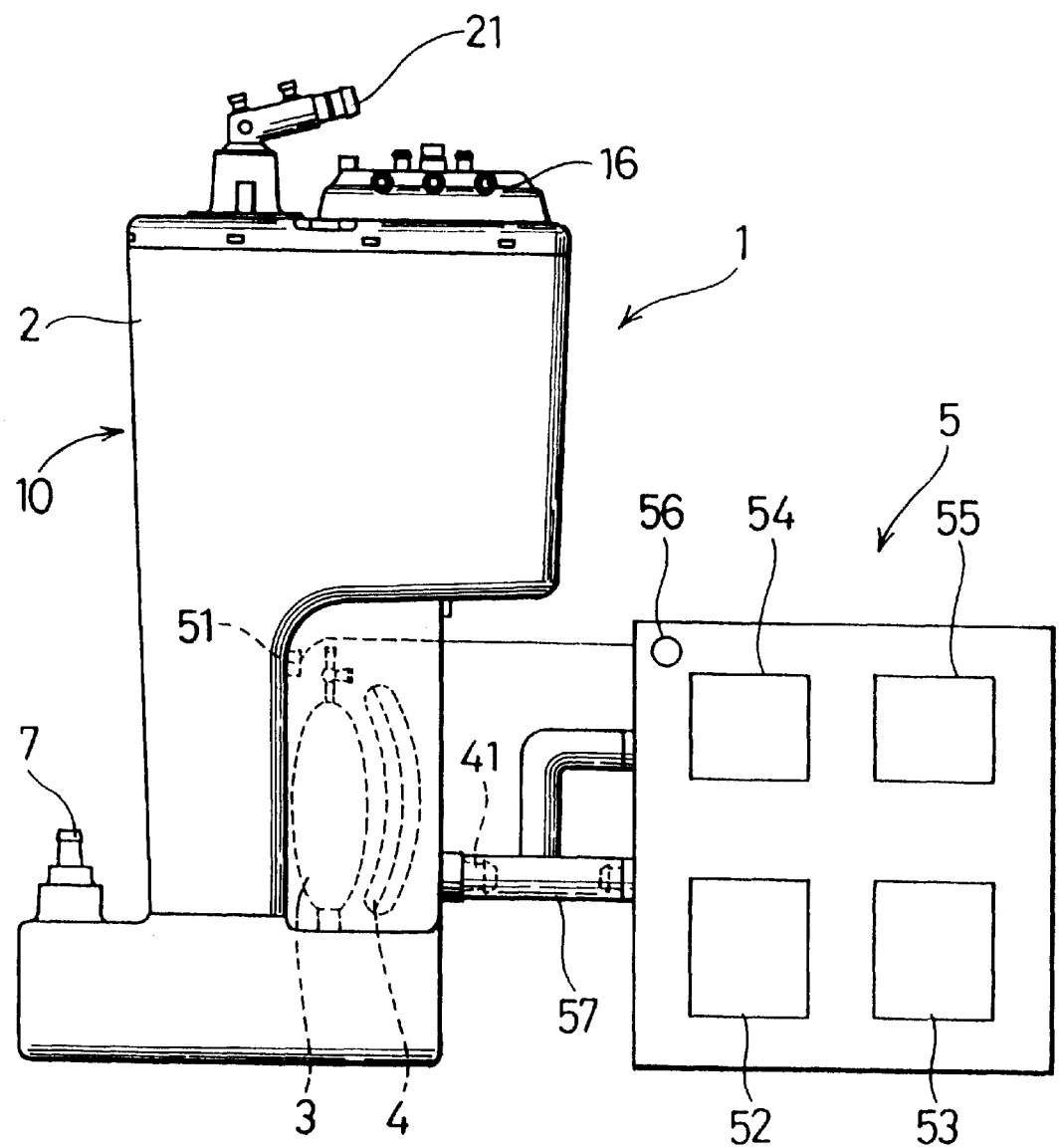
FIG. 1 is a schematic view of a blood delivery apparatus comprising a blood reservoir and a fluid feed unit according to a first embodiment of the invention.

The blood reservoir and blood delivery apparatus according to the invention are described in detail in conjunction with several preferred embodiments shown in the drawings.

Referring to FIGS. 1 through 9, a blood delivery apparatus 1 according to the invention includes a blood reservoir 10 and a blood delivery fluid feed unit 5.

The blood reservoir 10 includes a blood tank 2 having blood inlets 21, 22 and a blood outlet 26, a blood accumulator 3 in communication with the blood outlet 26, and a pumping means 4 for the driving accumulator 3 so as to deliver blood in the accumulator 3 to a downstream destination. The blood accumulator 3 is adapted to store blood in an amount proportional to the volume of blood reserved in the tank 2 at least when the volume of blood reserved in the tank 2 is below a predetermined value. The pumping means 4 is intermittently operated to drive the accumulator 3 so as to intermittently deliver blood therefrom. The pumping means 4 is controlled by a fluid feeder 5 for delivery.

As mentioned above, the blood accumulator 3 stores blood in an amount proportional to the volume of blood in the tank 2 when the volume of blood in the tank 2 is below the predetermined value and the pumping means 4 acts to intermittently deliver blood from the accumulator 3. As the residual blood volume in the tank 2 decreases, blood is accordingly delivered in a smaller amount. Even when the residual blood volume in the tank 2 is very small, delivery of a minor amount of blood is maintained. It is unnecessary to interrupt blood delivery when the residual blood volume in the tank 2 decreases, thereby avoiding blood stagnation in an extracorporeal blood circulation circuit.

The blood reservoir 10 includes the blood tank 2 and a blood delivery instrument 6 which includes the blood accumulator 3 and the pumping means 4.

Figure 2:
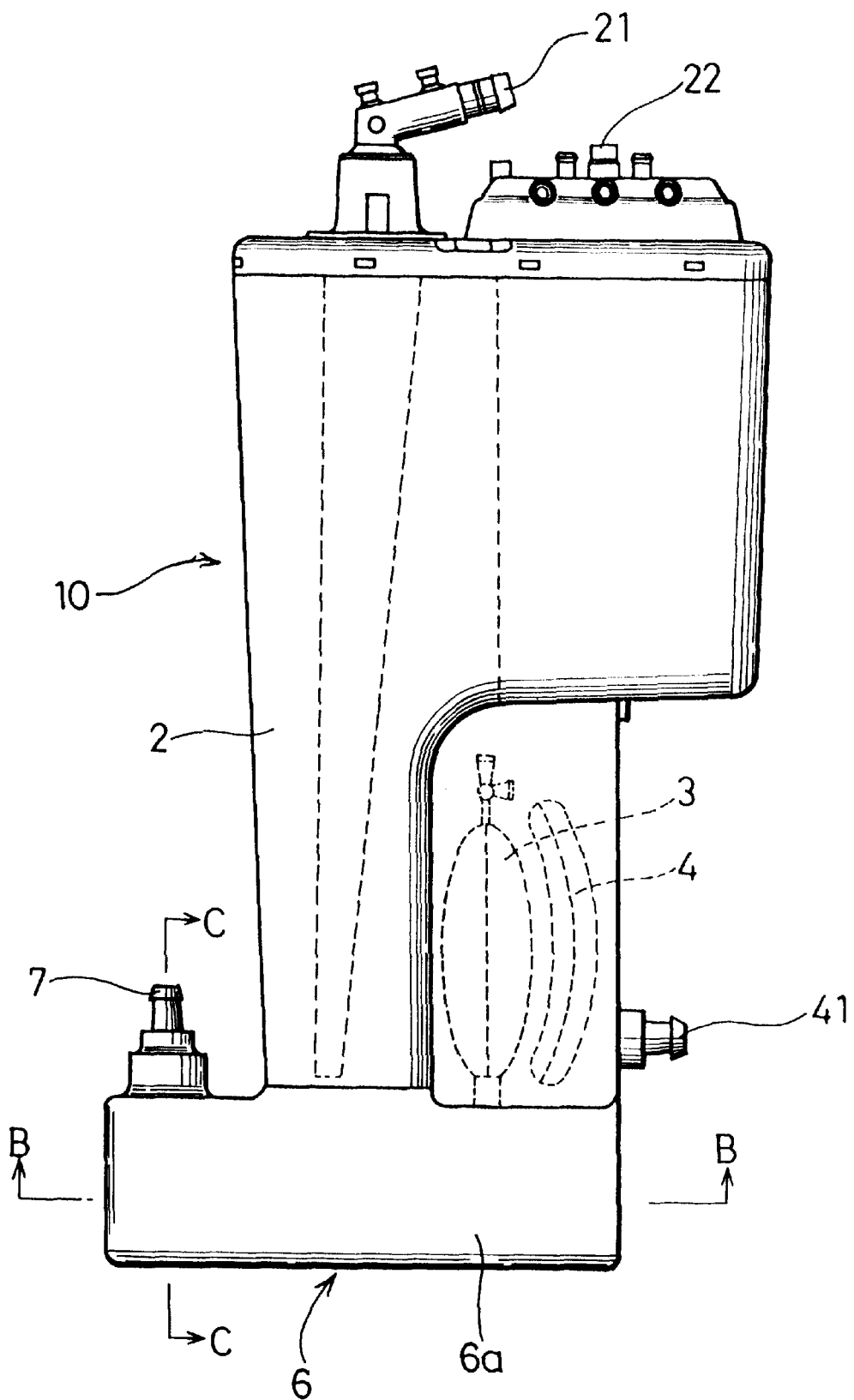
FIG. 2 is a front elevation of the blood reservoir according to the invention.
Figure 4:
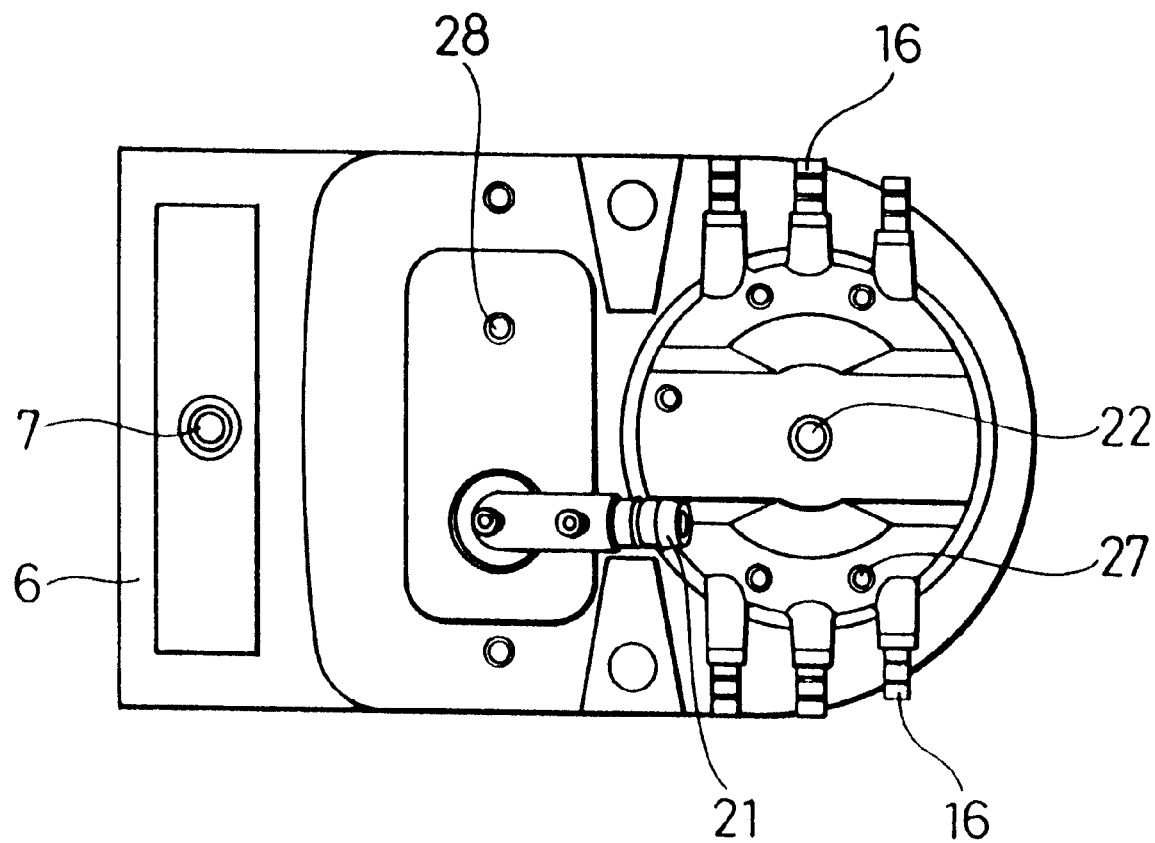
FIG. 4 is a top view of the reservoir of FIG. 2.
Figure 6:
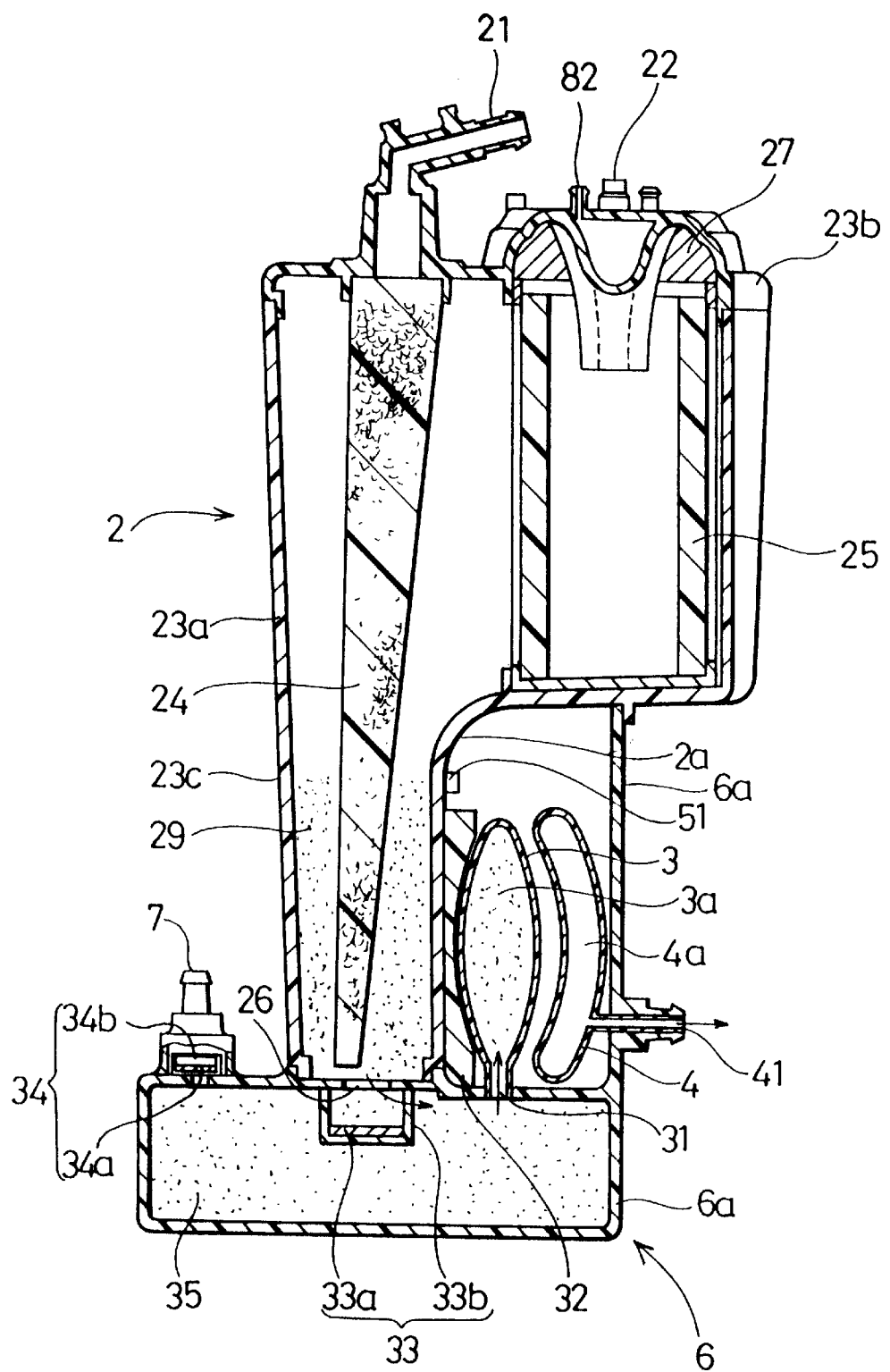
FIG. 6 is a cross-sectional view taken along lines A—A in FIG. 5.

As shown in FIG. 6, the blood tank 2 includes a tank housing consisting of a main body 23a and a cover 23b both made of rigid resin. The cover 23b is fitted on the top end of the housing main body 23a so as to cover the upper opening of main body 23a as shown in FIGS. 2 and 6. The cover 23b has blood flow inlets 21 and 22 and air vents 27 and 28 as shown in FIG. 4. The blood flow inlet 22 is connected to a cardiotomy line for feeding blood from the operation area. The blood flow inlet 21 is connected to a drainage line for feeding blood from a drainage cannula inserted into the heart ascending/descending veins of the patient. Received in the housing main body 23a are a cardiotomy blood filter 25 for filtering the blood incoming from inlet 22 and a venous blood filter 24 for filtering the blood incoming from the inlet 21.

The housing main body 23a has a downward projection 23c. The blood outlet 26 is formed in the bottom of the projection 23c.

The housing may be formed of any desired resin, for example, polycarbonate, acrylic resin, polyethylene terephthalate, polyethylene, polypropylene, polystyrene, polyvinyl chloride, acryl-styrene copolymers, and acryl-butadiene-styrene copolymers. Polycarbonate, acryl resin, polystyrene, and polyvinyl chloride are especially preferred.

Figure 3:
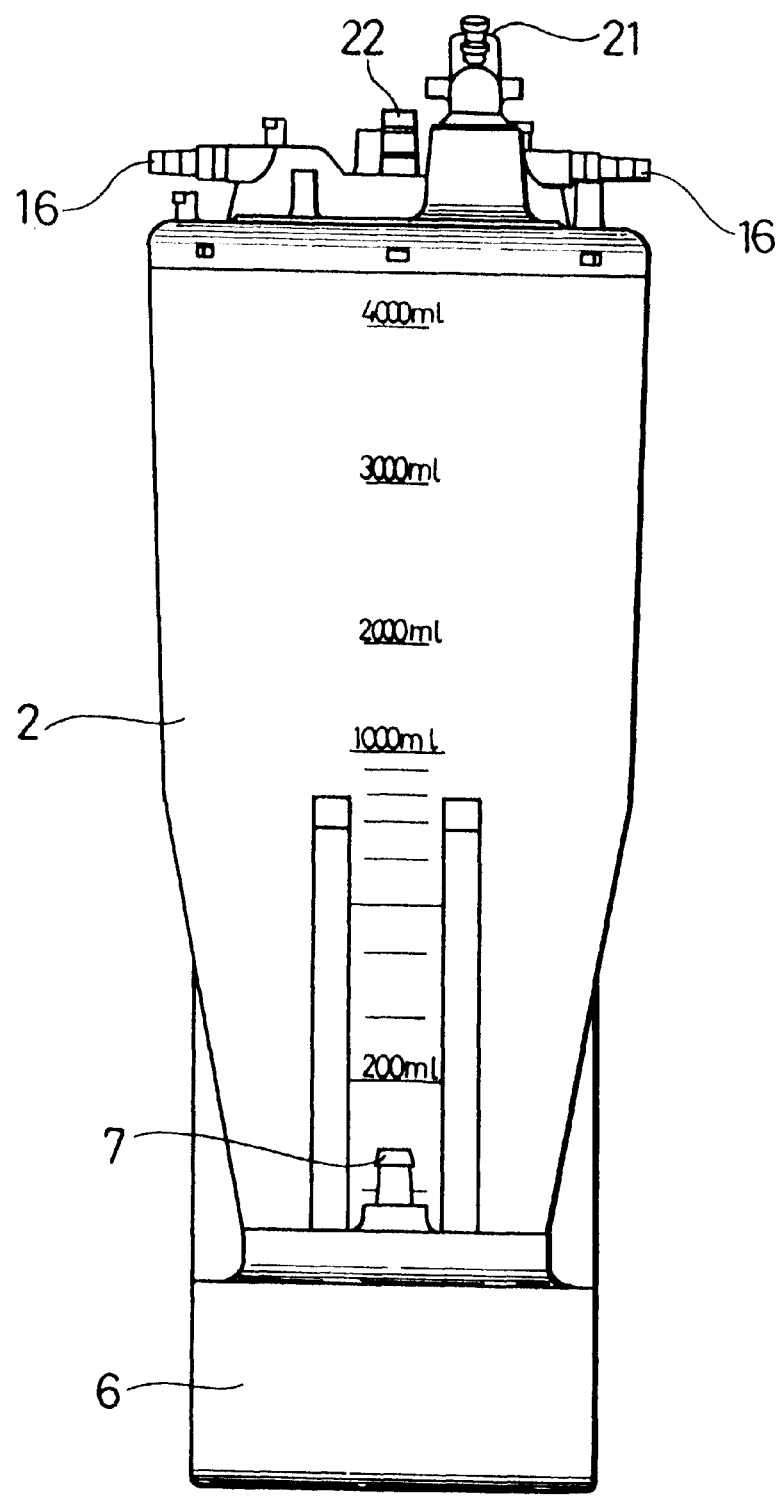
FIG. 3 is a left side view of the reservoir of FIG. 2.

Defined within the blood tank housing is a blood reserve portion 29 for temporarily reserving blood as shown in FIG. 6. The blood reserve portion 29 may have any desired volume although it generally has a volume of about 3,000 to 5,000 ml for adults and about 1,000 to 2,500 ml for children. The housing is preferably substantially transparent or semi-transparent so that the volume or state of blood reserved may be readily ascertained. The downward projection 23c has a reduced horizontal cross-section so that when the volume of blood reserved lowers, the volume of blood reserved or a change thereof can be correctly and readily read. As shown in FIG. 3, the projection 23c is convergent downward, that is, has a cross-sectional area decreasing toward the bottom. Scale marks are printed on the outside wall of the projection 23c. The blood tank 2 may also be a flexible tank formed of flexible resin. In this case, the blood tank is of the closed type.

Attached at the bottom of the blood tank 2 is the blood delivery instrument 6 which includes a housing 6a joined to the tank housing 23a. The blood delivery instrument 6 further includes the blood accumulator 3 and the blood delivery pumping means 4 received between the instrument housing 6a and the tank housing 23a. Disposed between the blood tank housing 23a and the blood accumulator 3 is a backing 32 for retaining the accumulator 3. The backing 32 has a side configured in conformity with one side shape of the accumulator 3 when the accumulator 3 is full of the maximum amount of blood.

A blood channel section 35 is defined by the blood delivery instrument 6 on its lower side and provides fluid communication between the interior 29 of the blood tank 2 and the blood accumulator 3. Disposed in proximity to blood flow the outlet 26 of the blood tank 2 is a first check valve 33 which permits blood passage from the blood tank 2 to the blood channel section 35 (and hence, the blood accumulator 3), but restricts or prohibits the blood passage in the opposite direction. This first check valve 33 functions as a flowpath control member for shutting off communication between the blood tank 2 and the accumulator 3 during operation of the pumping means 4 as will be described later. The blood delivery instrument 6 is provided with a blood exit port 7 in communication with the blood channel section 35. Disposed in proximity to the blood exit port 7 is a second check valve 34 which permits blood passage to a side downstream of the blood channel section 35 (and hence, downstream of the blood accumulator 3), but restricts or prohibits blood passage in the opposite direction. This second check valve 34 functions as a flowpath control member for shutting off blood flow from the downstream side into the accumulator side (and hence, blood channel side) when the pumping means 4 is inoperative as will be described later.

Each check valve 33, 34 has a disc-shaped movable valve body 33a, 34a and a cage 33b, 34b adapted to receive the valve body therein and formed with an opening for blood passage. The movable valve body 33a, 34a preferably has a specific gravity substantially equal to or slightly lighter than the specific gravity of blood so that the valve body may be fully responsive. For example, the valve body is made of expanded polyethylene and has a thickness of about 1 to 10 mm, especially 3 to 8 mm.

In another embodiment, the check valve takes the form of a movable valve body a part of which is fixedly secured to the housing. Preferably the movable valve body is slightly lighter than the specific gravity of blood and a hardness of about 3 to 7 on Shore A scale. For example, the valve body is made of styrene elastomer oil gel or silicone gel and has a thickness of about 1 to 5 mm.

The blood accumulator 3 is in fluid communication with the blood channel section 35 via a blood passage port 31 which is located below or at the lower end of the accumulator 3 and formed at a position of the same height as the lower end of the blood reserve portion 29 (the outlet 26) of the blood tank 2 in a vertical direction. The blood tank 2 has the blood reserve portion 29 and the outlet 26 located at a lower end portion thereof. The accumulator 3 is located upwards than the outlet 26. The blood accumulator 3 extends substantially vertically upward and substantially parallel to the projection 23c of the blood tank 2 in this embodiment. The accumulator 3 is formed as a bag or bladder of flexible resin. Under the condition that blood accumulator 3 is set so as to extend upward and parallel to the projection 23c of the blood tank 2, if the surface of blood in the tank 2 is below the uppermost end of the interior of the accumulator 3, an amount of blood proportional to the blood surface in the tank 2 flows into the accumulator 3. Inversely, now that the maximum containment amount of the blood accumulator 3 remains unchanged, if the surface of blood in the tank 2 is above the uppermost end of the interior of the accumulator 3, this maximum containment amount of blood flows into the accumulator 3.

Differently stated, the blood accumulator 3 is a pressure sensitive container since a pressure proportional to the volume of blood reserved in the tank 2 is applied thereto. When the volume of blood in the tank 2 is above a predetermined value (or the surface of blood in the tank 2 is above the uppermost end of the interior of the accumulator 3 in the illustrated embodiment), the maximum containment amount of the accumulator 3 becomes preferential to the pressure exerted by the volume of blood in the tank 2 so that the accumulator 3 contains the maximum containment amount of blood. If the volume of blood in the tank 2 is below the predetermined value (or the surface of blood in the tank 2 is below the uppermost end of the interior of the accumulator 3 in the illustrated embodiment), the accumulator 3 exerts a pressure sensitive function to contain blood in an amount proportional to the volume of blood in the tank 2 (or the height of the blood surface in the tank 2). Thus, the accumulator 3 has the function of automatically storing blood in an amount proportional to the volume of blood in the tank 2 when the volume of blood in the tank 2 is below the predetermined value.

It is preferred that the blood accumulator 3 does not suck in blood by itself, in another parlance, does not have a self-shape-recovery ability. If the accumulator 3 is formed to a shape defining a certain internal cavity, the accumulator 3 will restore the original shape when blood stored therein is displaced by pumping member 4 and the compression load by the pumping member 4 is released. The restoring force then creates a suction force to provide suction of blood from the tank side. Then the accumulator has a minimum blood containment amount below which the accumulator cannot exert the pressure sensitive function mentioned above. The minimum blood containment amount associated with the self recovery force should preferably be zero although its presence is acceptable if it is negligibly small. The preferred form of the blood accumulator is a flexible bag prepared by placing a pair of sheets in close plane contact with a tube to form the blood passage port 31 interposed at the lower end, and heat sealing the sheets along the periphery to define a sealed interior except for the tube. This bag has an internal volume of substantially zero as formed. Differently stated, it is preferred that when a load is applied to the blood accumulator so as to establish a state that the internal volume is substantially zero and then released, the blood accumulator maintains the substantially zero volume state. The maximum blood containment amount (simply maximum amount or maximum displacement) of blood accumulator 3 is preferably about 20 to 500 ml, more preferably about 50 to 300 ml, further preferably about 80 to 300 ml although the exact amount varies with the maximum volume of blood reserved in the blood tank combined therewith. It is preferred that the maximum blood containment amount of the accumulator 3 is greater than the volume of the channel section 35. Consequently, when blood is displaced from the accumulator 3, the entire volume of blood contained in the channel section 35 is displaced so that the stagnation of blood in the channel section 35 may be minimized.

The blood accumulator 3 in the illustrated embodiment is entirely formed of a flexible material and thus entirely deformable so that the accumulator 3 may be compressed and deformed when the blood delivery pumping means 4 is inflated. However, the blood accumulator is not limited to the entirely flexible one. It is acceptable that a portion of blood accumulator 3, for example, a portion of the blood accumulator 3 which comes in contact with the pumping means 4 is a deformable portion formed of a flexible material.

Blood contained in the accumulator 3 is displaced by the blood delivery pumping means 4 into the channel section 35 and then discharged to an outside destination through the exit port 7. When the volume of blood reserved in the tank 2 is smaller than the predetermined value, blood is delivered in an amount proportional to the residual volume of blood in the tank 2. As the residual volume of blood in the tank 2 becomes smaller, the amount of blood delivered is automatically reduced to a level approximate to zero, but not reduced to zero. That is, the blood reservoir 10 of the invention always maintains blood delivery though in a very small amount. Thus the interruption of blood delivery never occurs, preventing blood stagnation on a side of the extracorporeal blood circulation circuit downstream of the blood reservoir 10.

Since the blood accumulator 3 is a flexible bag, it provides a very low resistance to blood inflow and sensitivity to pressure variations so that blood may be contained in an amount fully proportional to the residual volume of blood in the tank 2. Moreover, the accumulator 3 is designed such that it contains the predetermined amount of blood in the duration when the volume of blood in the tank 2 is above the predetermined level, while the amount of blood contained in accumulator 3 varies in proportion of the residual volume of blood in the tank 2 in the duration when the volume of blood in the tank 2 is below the predetermined level. The maximum containment amount is fixed and this maximum containment amount of blood is contained when the volume of blood in the tank 2 is above the predetermined level. Then the amount of blood delivered by pumping means 4 in the normal state can be readily controlled in terms of the number of compressions or pulsations per unit time of accumulator 3 by pumping means 4. A substantially constant amount of blood is delivered per pulsation. Satisfactory pulsative blood flow can be easily established.

The blood accumulator is desired to be fully flexible. One index of flexibility is compliance. The blood accumulator preferably has a compliance of above 2 ml/sec·mHg, preferably 5 to 30 ml/sec·mHg when the surface of blood in the reserve portion of the tank 2 is lower than the uppermost end of the interior of the accumulator, differently stated, when the accumulator exerts a pressure (or blood level) sensitive function. Further preferably the blood accumulator reduces its compliance to a lower value when the surface of blood in the reserve section of the tank 2 is above than the uppermost end of the interior of the accumulator. The resistance of the accumulator to blood inflow can be expressed by an inflow rate of blood into the accumulator and the accumulator preferably has a blood inflow rate of 20 to 600 ml/sec.

Examples of the flexible resin include polyvinyl chloride, vinyl chloride-vinyl acetate copolymers, vinyl chloride-ethylene copolymers, vinyl chloride-vinylidene chloride copolymers, vinyl chloride-urethane copolymers, vinyl chloride-acrylonitrile copolymers, vinyl chloride-methyl methacrylate copolymers, and flexible polyvinyl chloride modified products comprising the foregoing polymers and plasticizers, and polyurethane.

Thermoplastic polyurethanes are especially preferred. The thermoplastic polyurethanes may be either thermoplastic polyether polyurethanes or thermoplastic polyester polyurethanes, with the thermoplastic polyether polyurethanes being preferred. Especially preferred are thermoplastic polyether polyurethanes comprising soft and hard segments. The soft segment is preferably formed from polytetramethylene ether glycol, polyethylene glycol and polypropylene glycol as a main component. The hard segment is preferably formed from 1,4-butane diol as a main component. The diisocyanate includes 4,4-diphenylmethane diisocyanate, tolylene diisocyanate, and 1,6-hexamethylene diisocyanate. Most preferred polyurethane material is a thermoplastic segmented polyurethane which is formed using polytetramethylene ether glycol as a main component of the soft segment, 1,4-butane diol as a main component of the hard segment, and 4,4-diphenylmethane diisocyanate as the diisocyanate. This polyurethane is commercially available under the trade name of Pelecene 2363 from Dow Chemical Co.

The surface of the accumulator which will be wetted with blood is preferably antithrombic. The antithrombic surface may be formed by applying and fixing an antithrombin to the surface. Exemplary antithrombins are heparin, urokinase, HEMA-St-HEMA copolymers, and poly-HEMA.

Preferably, the antithrombic surface is formed by treating a substrate with ozone to form functional group-bearing oxides on the substrate surface and applying heparin to the surface so that an amino group of heparin forms a covalent bond with the functional group directly or through a coupling agent. This method permits heparin to be fixed on the blood wetting surface without the use of a solvent, minimizing a change of physical properties (e.g., flexibility, elasticity and strength) of the substrate presenting the blood wetting surface.

Through ozone treatment, oxides are formed on the substrate surface and high reactive functional groups such as aldebyde, ketone, and epoxy groups are generated in the oxides. Amino groups of heparin can directly bond with these functional groups. For the reason of steric hindrance or other, introducing a spacer or coupling agent into these functional groups prior to fixation of heparin is easy and useful from the standpoint that the surface allows heparin to develop its activity. The coupling agents may be used alone or in admixture of two or more. Compounds having at least two aldehyde or epoxy groups are preferred.

Where two or more coupling agents are used, the preferred sequence is by first bonding a coupling agent (spacer coupling agent) in the form of a compound having at least two amino groups with the functional groups previously introduced in the substrate, to thereby introduce amino acid into the substrate, and thereafter bonding heparin to the substrate with the aid of a coupling agent (heparin-fixing coupling agent) in the form of a compound having at least two aldehyde or epoxy groups. In bonding heparin, the coupling agent is preferably admitted into the reaction system at the same time as or subsequent to heparin admission.

Especially when an amino group is introduced using a spacer coupling agent, it displays substantially the same reactivity as the amino group of heparin in the reaction system so that subsequent fixation of heparin to the substrate by the heparin-fixing coupling agent may take place more effectively.

Where the functional group of a coupling agent to directly bond with heparin or the functional group introduced into the substrate is an aldehyde group, it is preferable to use heparin in which some N-sulfate groups are desulfurized into primary amino groups.

The spacer coupling agent is one that forms a bond (covalent bond) with the functional group introduced on the substrate by ozone treatment and has at least two primary amino groups. Examples of the spacer coupling agent having at least two amino groups include polyethylene imine (PEI), polyethylene glycol diamine, ethylene diamine, and tetramethylene diamine.

Aldehyde and epoxy compounds are preferable as the coupling agent used for fixing heparin to the substrate. Exemplary of the aldehyde compound are glutaraldehyde, glyoxal, and succindialdehyde. Exemplary of the epoxy compound are polyethylene glycol diglycidyl ether, 1,4-butane diol diglycidyl ether, sorbitol diglycidyl ether, and glycerol diglycidyl ether. Illustrative examples are Denacol EX-421, 521, 611, 612, 614, and 614B where the epoxy compound is sorbitol diglycidyl ether; Denacol EX-313 where the diepoxy compound is glycerol diglycidyl ether; Denacol EX-810, 811, 851, 821, 830, 832, 841, and 861 where the diepoxy compound is polyethylene glycol diglycidyl ether, all commercially available from Nagase Chemicals K.K. Denacol EX-313, 421, 512, 521, 810, 811, 821, and 851 are preferred when the difference of epoxy reactivity is considered. In the above-mentioned heparin fixation, coupling-off of heparin is minimized since the bond between polyethylene imine fixed to the substrate and glutaraldehyde and the bond between glutaraldehyde and heparin are both covalent bonds.

Figure 9:
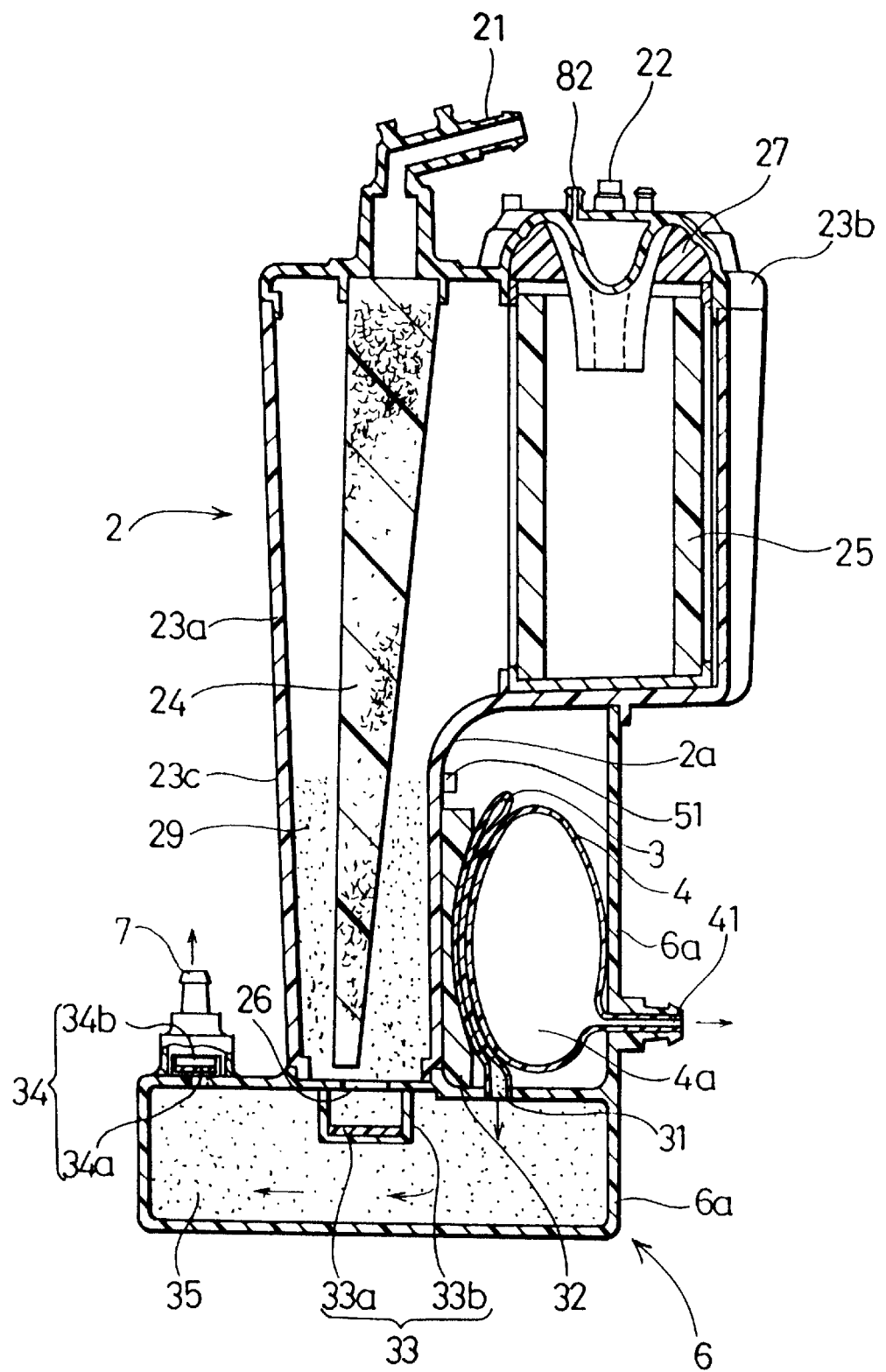
FIG. 9 is a schematic view for explaining the operation of the blood reservoir of the first embodiment.

Disposed between the accumulator 3 and a vertically extending side wall of the housing 6a of the blood delivery instrument 6 is the blood delivery pumping means 4. The pumping means 4 is preferably a flexible bag formed of a flexible resin as used in the accumulator and defining a fluid flow space 4a therein. The pumping means 4 is in fluid communication with a fluid flow port 41 in the housing side wall 6a of the blood delivery instrument 6. On use, the port 41 is connected to fluid feed unit 5 for feeding fluid for blood delivery as shown in FIG. 1. A compressor built in the fluid feeder unit 5 operates to feed or discharge an operative liquid or gas to or from the pumping bag 4 for expansion or contraction. Upon contraction, the pumping bag 4 does not contact the accumulator bag 3 as shown in FIG. 6. Upon expansion, the pumping bag 4 inflates as shown in FIG. 9 to compress the accumulator bag 3 against the backing 32 for displacing blood out of the accumulator bag 3. The containment for receiving the accumulator bag 3 (defined between the blood tank housing 23a and the blood delivery instrument housing 6a) may be sealed substantially gas-tight. In this case, the containment is under positive pressure upon inflation of the pumping bag 4, but upon contraction of the pumping bag 4, the containment is kept under negative pressure which facilitates initial inflow of blood into the accumulator bag 3. Since the blood delivery pumping means 4 is in the form of a flexible bag which is inflated or contracted by feeding fluid into and out of the bag in the illustrated embodiment, it causes little damage to the accumulator 3 when compressing accumulator 3. Since the accumulator 3 has a deformable portion formed of flexible material and upon blood delivery, the pumping means 4 acts to deform that deformable portion to displace blood out of the accumulator 3, blood can be intermittently discharged from the accumulator 3 in an amount proportional to the volume of blood reserved in the blood tank 2.

The blood delivery pumping means 4 can regulate the amount of blood displaced out of the accumulator 3 by adjusting the amount or pressure of operative fluid introduced in the pumping means 4. The amount of blood to be displaced can be readily changed by setting a fixed number of driving actions of the pumping means 4 per unit time and adjusting the amount or pressure of operative fluid introduced in the pumping means 4. When the pumping means 4 is designed so as to displace blood out of the accumulator 3 while leaving some amount of blood therein, no excessive stresses are applied to the accumulator 3 and the sheets forming the accumulator 3 are not closely joined, preventing any obstruction against blood inflow into the accumulator 3 which would otherwise be caused by close junction.

Figure 10:
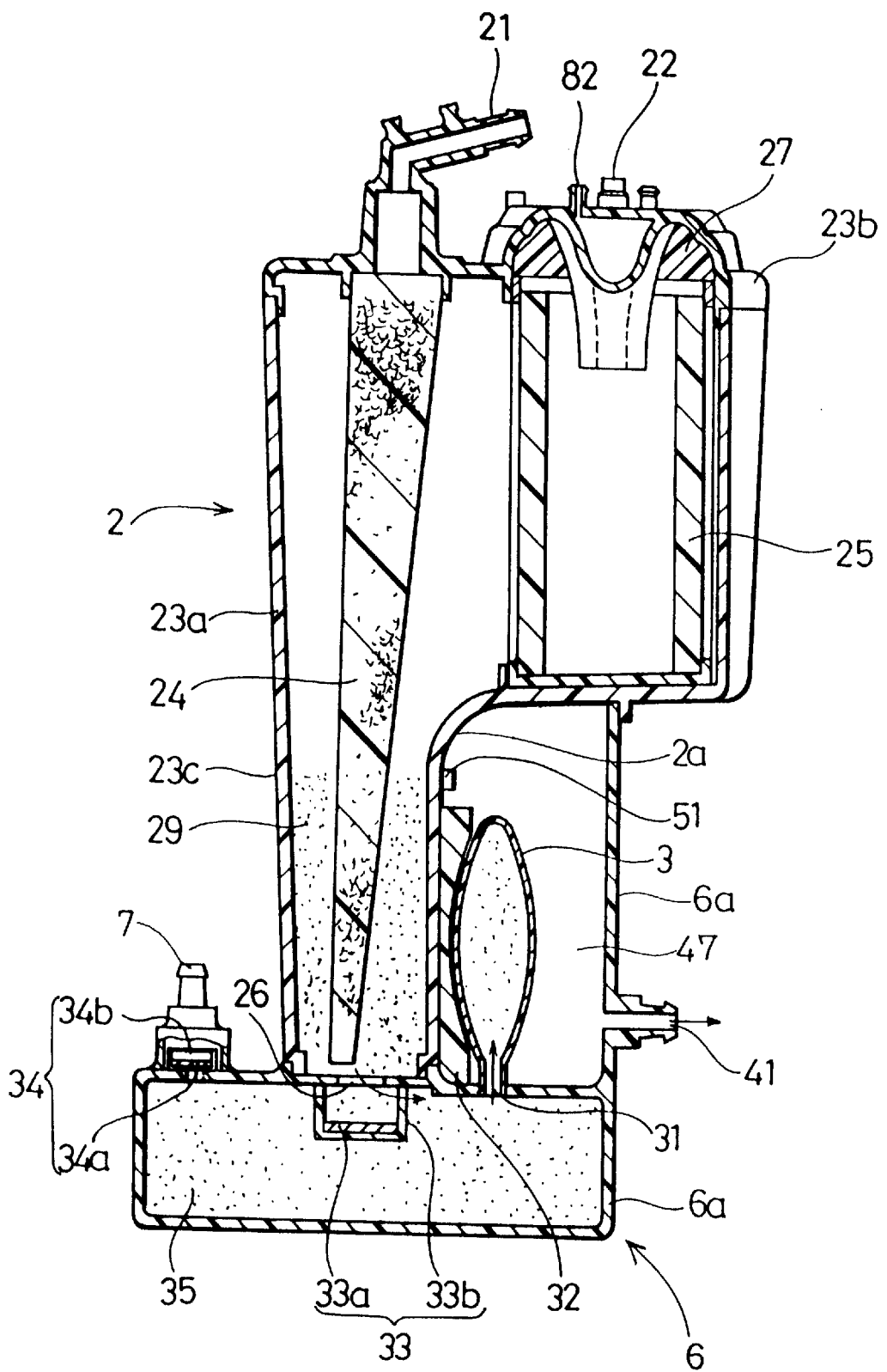
FIG. 10 is a cross-sectional view of a blood reservoir according to another embodiment of the invention.

In another embodiment, a pumping bag or member can be omitted and pumping means of a different structure is constructed as shown in FIG. 10. In this embodiment, the containment 47 defined between the blood tank housing 23a and the blood delivery instrument housing 6a for receiving the accumulator 3 is sealed substantially gas-tight. The communication port 41 is connected to a pressurizing means in the form of a blood delivery fluid feed unit. A compressor built in the fluid feed unit 5 operates to feed or discharge an operative liquid or gas to or from the containment 47 so that the accumulator 3 itself repeats expansion or restoring contraction.

Figure 11:
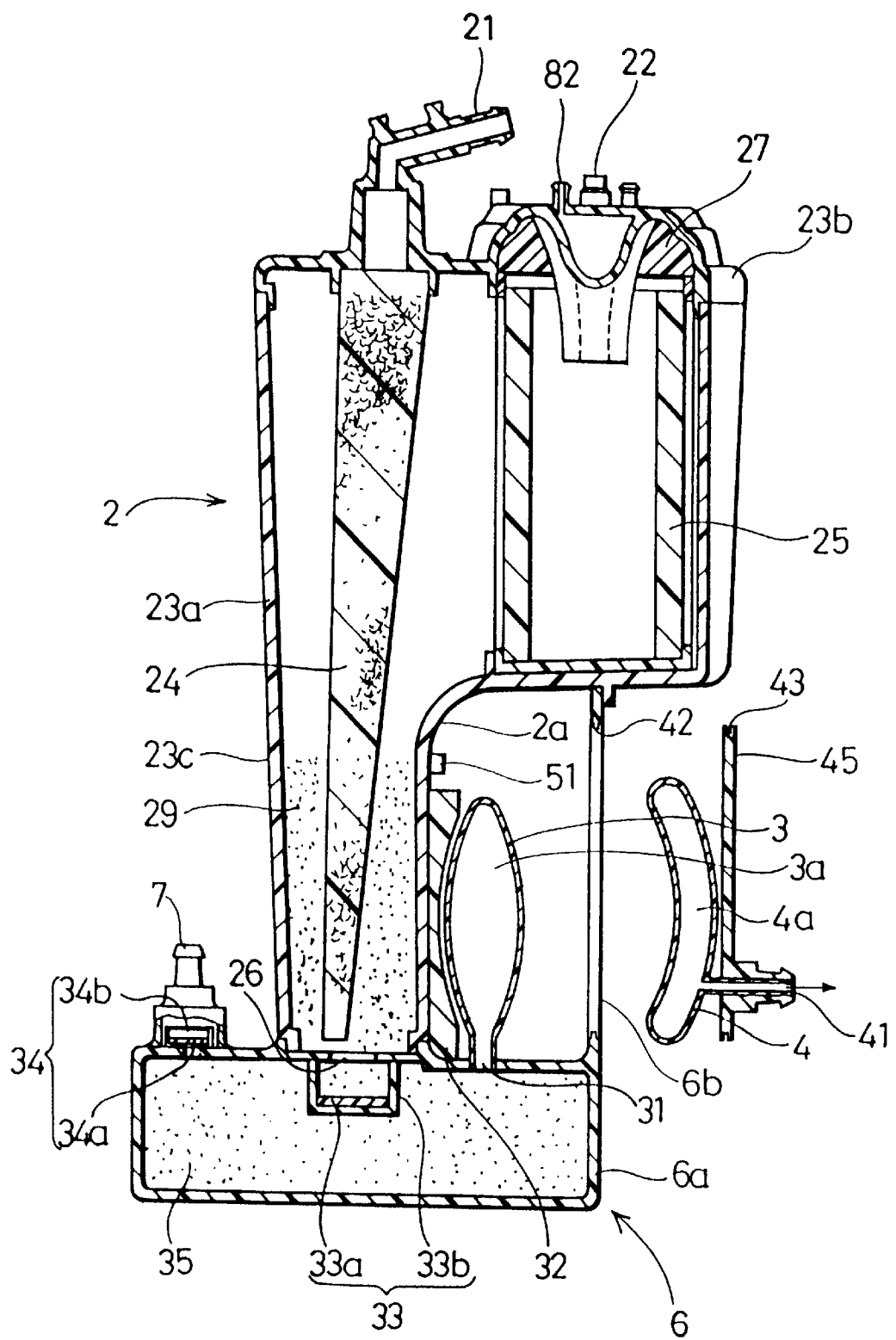
FIG. 11 is a cross-sectional view of a blood reservoir according to a further embodiment of the invention.
Figure 12:
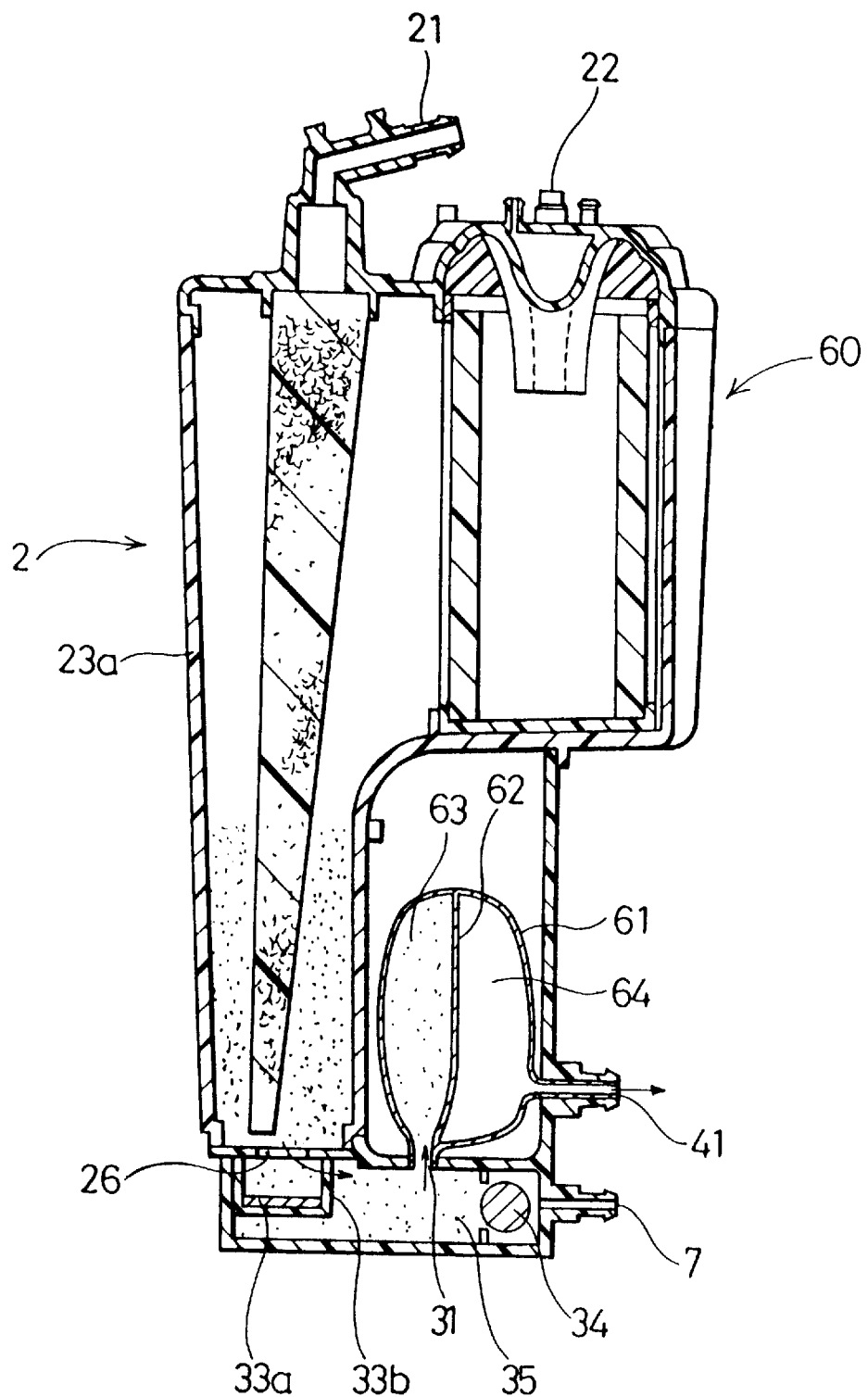
FIG. 12 is a cross-sectional view of a blood reservoir according to a still further embodiment of the invention.

In the illustrated embodiments, the blood reservoir including the pumping means 4 is disposable as a whole. The invention is not limited to these embodiments. As shown in FIG. 11, the blood delivery pumping means 4 is removable from the blood reservoir since the pumping means 4 does not contact blood. The blood reservoir 10 of this embodiment does not have the pumping means 4 and the port 41 as integral components and instead, has an attachment therefor. More particularly, a blood delivery drive assembly including a plate member 45 provided with the port 41 and the pumping means 4 is separately furnished. The plate member 45 is attached to an opening 6b in the instrument housing 6a. The plate member 45 is provided with the engagements 43 and the instrument housing 6a is provided with the engagements 42. Through these engagements, the plate member 45 (or the blood delivery drive assembly) is tightly attached to the reservoir 10 so that the assembly may not be readily removed.

Figure 5:
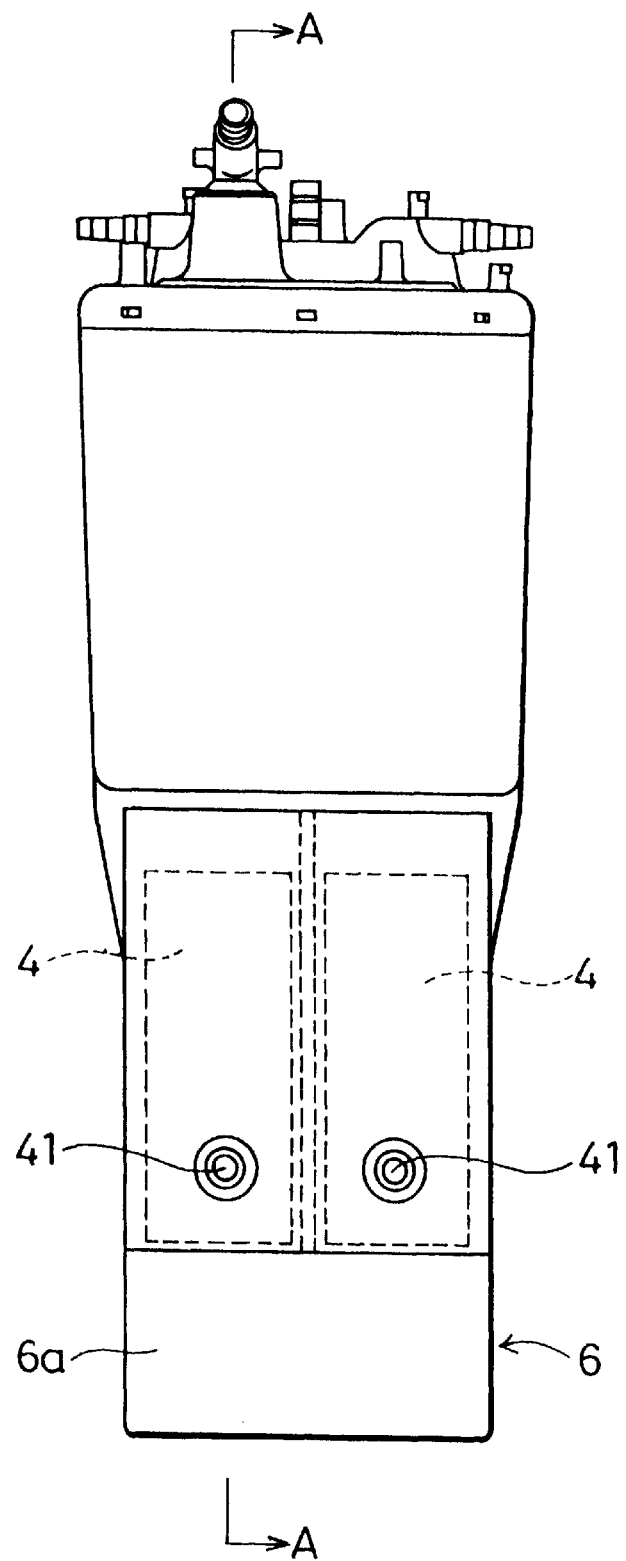
FIG. 5 is a right side view of the reservoir of FIG. 2.
Figure 7:
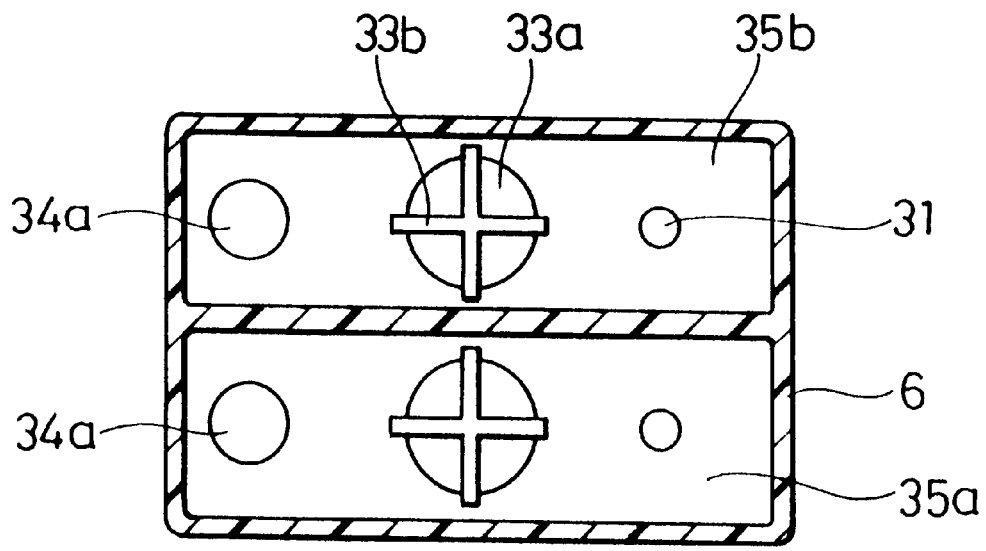
FIG. 7 is a cross-sectional view taken along lines B—B in FIG. 2.
Figure 8:
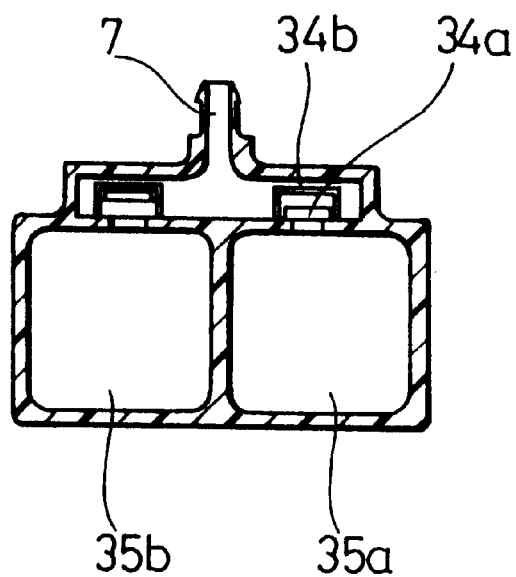
FIG. 8 is a cross-sectional view taken along lines C—C in FIG. 2.

As seen from FIG. 5, the blood reservoir 10 of the illustrated embodiment has two sets of the accumulators 3 and the pumping means 4. Then blood channel 35 is also partitioned into two blood channels 35a and 35b which are not in fluid communication with each other as shown in FIGS. 7 and 8. When two or more sets of the accumulators 3 and the pumping means 4 are provided, the volume of each the accumulator 3 and the pumping means 4 is reduced so that the response of blood inflow and outflow is improved. If expansion timing is shifted between two pumping means 4, there can be formed a better blood flow. Despite shifted expansion timing between two pumping means 4, it never happens that blood flows from one accumulator to the other accumulator since two blood channels 35a and 35b are not in fluid communication with each other and each accumulator has an independent blood channel. The invention is not limited to the illustrated embodiment. The accumulator 3 and the pumping means 4 may be provided one set or three or more sets. Although the bag adapted to undergo repetitive inflation and contraction under the action of operative fluid is used as the pumping means 4 in the illustrated embodiment, the invention is not limited thereto. For example, a mechanism including a pressure plate in contact with one side of a blood accumulator wherein the pressure plate is mechanically driven against the blood accumulator may be used as in the blood delivery apparatus shown in FIG. 14 to be described later.

In the illustrated embodiment of the blood reservoir 10 comprising two sets of accumulators 3 and pumping means 4 and a blood delivery fluid feed unit having a control ability to independently drive the pumping means 4, the form of blood flow to be delivered can be selected between a pulsative flow and a constant flow by taking into account the state of the patient and the artificial lung associated with the circulation line. Additionally the mode of blood flow to be delivered can be changed during operation. In the illustrated embodiment comprising two sets of accumulators 3 and pumping means 4, a substantially constant blood flow is obtained as a whole when the phases of blood flows delivered from the respective channels are shifted approximately 180 degrees, differently stated, when the phases of fluid flows discharged into or out of the pumping means 4 for blood delivery are shifted approximately 180 degrees. Inversely, a pulsative blood flow is obtained when the phases of blood flows delivered from the respective channels are the same or ±30 degrees, differently stated, when the phases of fluid flows discharged into or out of the pumping means 4 for blood delivery are the same or ±30 degrees. Where three or more sets of accumulators 3 and pumping means 4 are provided, a substantially constant blood flow is obtained when the phases of blood flows delivered from the respective channels are shifted an angle of 360° divided by the number of sets.

Figure 13:
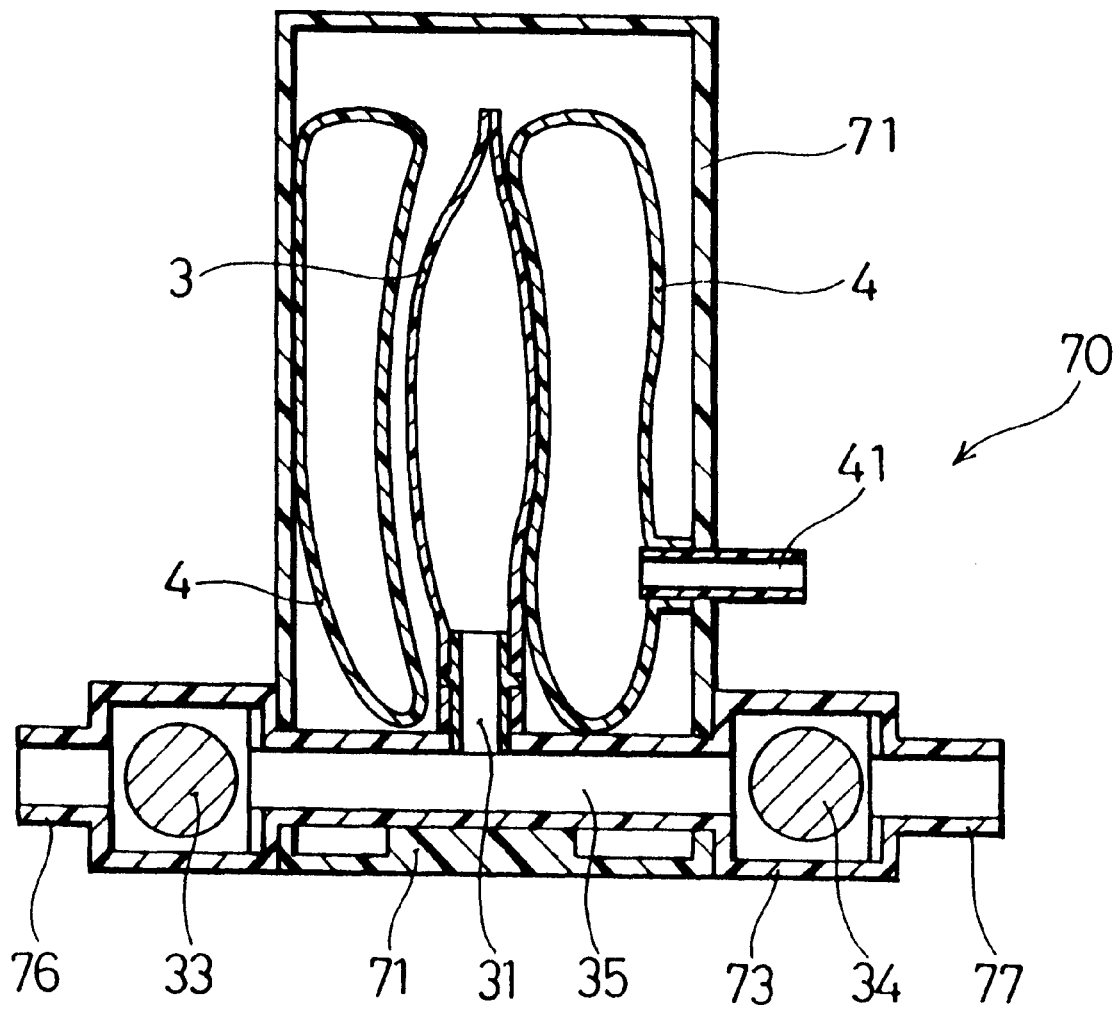
FIG. 13 is a cross-sectional view of a blood delivery instrument according to one embodiment of the invention.

FIG. 13 illustrates a blood delivery instrument 70 according to the invention.

This blood delivery instrument 70 is used in an extracorporeal blood circulation circuit having a blood tank. The blood delivery instrument 70 includes a blood accumulator 3 in communication with a blood outlet of the tank and a pumping means 4 for driving accumulator 3 to deliver blood from the accumulator 3 outward. As in the first-mentioned embodiment, the blood accumulator 3 serves to temporarily store blood in an amount proportional to the volume of blood reserved in the tank 2 when the volume of blood in the tank 2 is below a predetermined value. The pumping means 4 serves to intermittently drive the accumulator 3 so as to displace blood therefrom.

The blood delivery instrument 70 includes an accommodating housing 71 having the accumulator 3 and the pumping means 4 received therein and a channel housing 73 disposed below the housing 71 and defining a blood channel 35 therein. The channel housing 73 has at one end a blood inlet port 76 connected to the outlet of the blood tank and at another end a blood outlet port 77. The accommodating housing 71 has a bottom configured to attach the channel housing 73 thereto and defines an interior space where the accumulator 3 and the pumping means 4 are received. The accumulator 3 and pumping means 4 may be the same as in the first-mentioned embodiment.

The blood accumulator 3 is in fluid communication with the blood channel 35 defined in the housing 73 through a blood passage port 31. Disposed in proximity to the inlet port 76 of housing 73 is a first check valve 33 which permits blood flow from the blood tank side to the blood channel 35 side (and hence, to the accumulator 3), but restricts reverse blood flow. Disposed in proximity to the outlet port 77 of the housing 73 is a second check valve 34. The check valves illustrated in the figure are ball valves. The interior of the pumping means 4 is in fluid communication with a port 41 for passing a blood delivery operative fluid.

In this embodiment, pumping means 4 is configured to the contact accumulator 3 at opposite surfaces. More particularly, the pumping bag 4 is folded and the accumulator bag 3 is interposed between the folded sections. Alternatively, the pumping bag 4 is formed in doughnut shape and the accumulator bag 3 is disposed at the center. The pumping bag 4 in contact with substantially the entire surface of the accumulator bag 3 ensures effective displacement of blood from the accumulator bag 3.

Next, the blood delivery fluid feed unit 5 shown in FIG. 1 is described.

The blood delivery fluid feed unit 5 is connected to the blood reservoir 10 through a tube 57 connected to the passage port 41 in communication with the pumping means 4. The fluid feed unit 5 has a fluid pump built therein for discharging a liquid (e.g., water and physiological saline) or gas (e.g., air) into and out of the pumping means 4 to intermittently repeat inflow and outflow of the fluid. The fluid feed unit 5 has a front panel including a switch section 52 having an input switch for setting a blood flow rate per unit time (e.g., a blood flow rate per minute) and/or an input switch for setting the number of pulsations per unit time (e.g., number of pulsations per minute). A display section 54 is to display the input blood flow rate and number of pulsations. The fluid feed unit 5 has built therein a computer which when a blood flow rate is input, computes the number of pulsations per unit time by considering the maximum capacity of the accumulator 3 (the amount of blood contained in the accumulator when the residual volume of blood in the blood tank is above a predetermined value) and delivers the computed result to the display section. Since the blood reservoir of the illustrated embodiment has two sets of accumulators and pumping means, the number of pulsations per unit time for each accumulator is one-half of the computed number of pulsations. Inversely, when a number of pulsations per unit time (e.g., a number of pulsations per minute) is input, a blood flow rate per unit time is computed by considering the maximum capacity of accumulator 3 and displayed at the display section.

The blood reservoir 10 has a level sensor 51 which is electrically connected to fluid feed unit 5, especially a lamp 56 through a control circuit. The level sensor 51 is attached to the blood tank 2 at a position corresponding to or slightly above the top end of the interior of the accumulator 3. When the level sensor 51 detects that the surface of blood is below the sensor 51, the lamp 56 flickers to indicate a blood delivery amount control mode. At the same time, any flow rate indication on the display section 55 disappears.

It is understood that blood delivery fluid feed unit 5 is applicable to all the illustrated embodiments.

The blood delivery fluid feed unit is not limited to the above-mentioned one. Another exemplary blood delivery fluid feed unit is shown in FIG. 33. This unit includes a display section 161 for displaying the flow rate detected by a flow rate sensor located downstream of the blood reservoir, a knob 162 for setting the pressure of blood delivery operative fluid, a display section 163 for displaying the pressure of blood delivery operative fluid, and a mode switch 164 for selecting a blood flow mode between a constant flow and a pulsative flow. While the number of pulsations of pumping blood delivery operative fluid per unit time is fixed, a knob is manually operated to adjust the pressure of blood delivery operative fluid for thereby adjusting the flow rate of blood. That is, this blood delivery fluid feed unit is to adjust the flow rate of blood by adjusting the force of the pumping means compressing the accumulator for thereby adjusting the amount of blood displaced from the accumulator (the amount of blood discharged from the blood contained in the accumulator).

Figure 14:
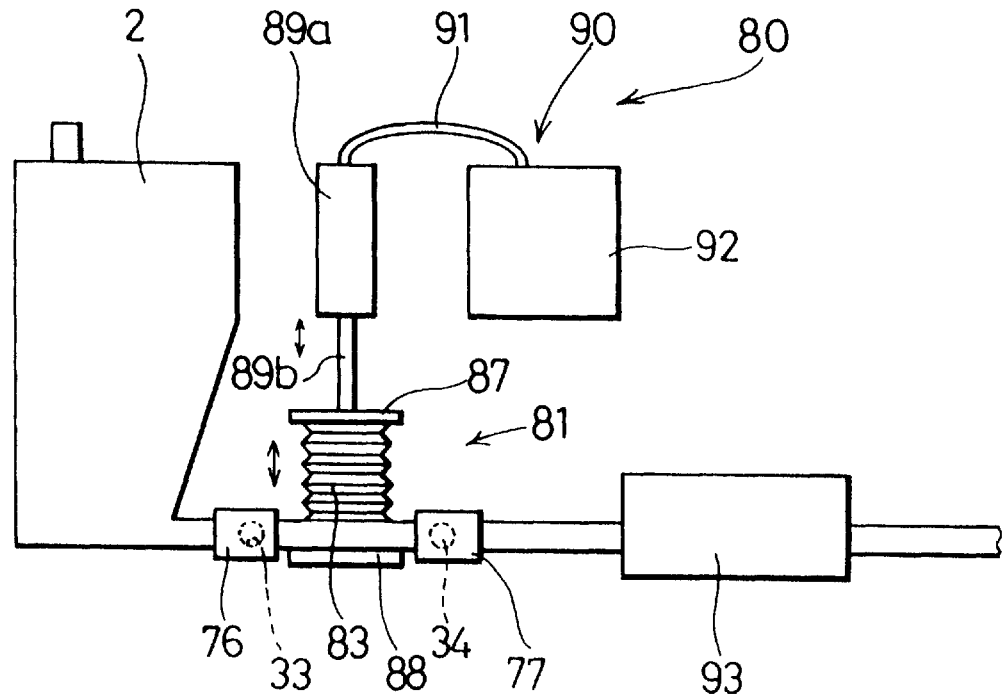
FIG. 14 is a schematic view of a blood delivery apparatus according to one embodiment of the invention.

FIG. 14 shows a blood delivery apparatus according to another embodiment of the invention.

This blood delivery apparatus 80 includes a blood delivery means 81 and a compression means 90. The blood delivery means 81 includes a blood channel having at one end a blood inlet port 76 connected to a blood outlet of a blood tank 2 and at another end a blood outlet port 77. The blood delivery means 81 further includes an accumulator 83 in fluid communication with the blood channel. The accumulator 83 is constructed as a vertically contractible bellows. The accumulator 83 in the form of a bellows is adapted to contain blood in an amount proportional to the volume of blood reserved in the blood tank when the volume of blood reserved in the blood tank is below the predetermined value. That is, when the volume of blood reserved in the blood tank is below the predetermined value, the top end of the accumulator bellows 83 lowers in accordance with the surface of blood in the blood tank.

The accumulator bellows 83 has a flat top end on which a pressure plate 87 is rested. The pressure plate 87 is fixedly secured to a piston rod 89*b* of a cylinder 89*a* to construct a blood delivery pumping means. The cylinder 89*a* is coupled to a hydraulic or pneumatic pressure generator 92 through a conduit 91 so that piston rod 89*b* is vertically moved by the operation of the generator 92. When the piston rod 89*b* is moved down, the pressure plate 87 urges the accumulator 83 downward. The accumulator bellows 83 is squeezed between the pressure plate 87 and a support plate 88 to reduce its interior volume to displace the blood therefrom to the channel and then to an artificial lung 93. Disposed in proximity to the inlet port 76 is a first check valve 33 which permits blood flow from the blood tank side to the blood channel side (and hence, to the accumulator 83), but restricts reverse blood flow. Disposed in proximity to the outlet port 77 is a second check valve 34. The check valves illustrated in the figure are ball valves.

Figure 15:
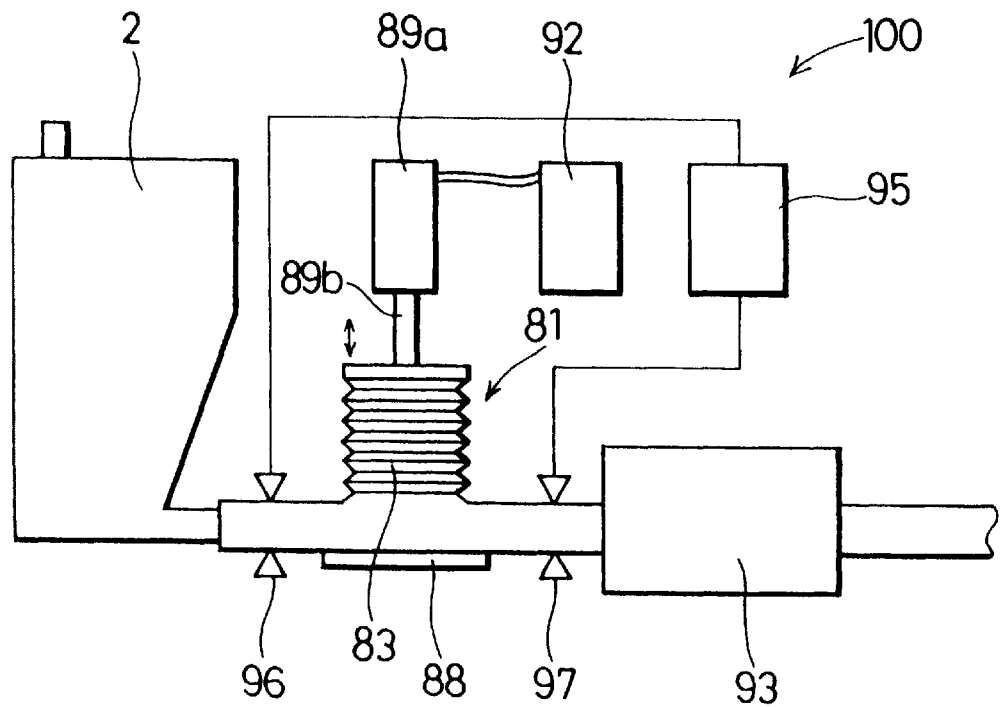
FIG. 15 is a schematic view of a blood delivery apparatus according to a further embodiment of the invention.

FIG. 15 shows a blood delivery apparatus according to a still further embodiment of the invention. The basic construction of this blood delivery apparatus 100 is the same as the foregoing apparatus 80. The difference resides in the use of flowpath control means instead of the check valves.

This blood delivery apparatus 100 includes a blood delivery means 81 and a compression means. The blood delivery means 81 includes a blood channel having at one end a blood inlet port connected to a blood outlet of a blood tank 2 and at another end a blood outlet port. The blood delivery means 81 further includes a accumulator 83 in fluid communication with the blood channel. The accumulator 83 is constructed as a vertically contractible bellows. The accumulator 83 in the form of a bellows is adapted to contain blood in an amount proportional to the volume of blood reserved in the blood tank when the volume of blood reserved in the blood tank is below the predetermined value. The accumulator bellows 83 has a flat top end on which a pressure plate is rested. The pressure plate is fixedly secured to a piston rod 89*b* of a cylinder 89*a* to construct a blood delivery pumping means. The cylinder 89*a* is coupled to a hydraulic pressure generator 92 through a conduit so that the piston rod 89*b* is vertically moved by the operation of the generator 92. When the piston rod 89*b* is moved down, the pressure plate urges the accumulator bellows 83 downward. The accumulator bellows 83 is squeezed between the pressure plate and a support plate 88 to reduce its interior volume to displace the blood therefrom to the channel and then to an artificial lung 93.

Disposed in proximity to the inlet port is a first flowpath control means 96 in the form of a clamp with an electromagnetic valve, for example. Disposed in proximity to the outlet port is a second flowpath control means 97. These flowpath control means 96 and 97 and the hydraulic pressure generator 92 are connected to a controller 95. The controller 95 controls so as to render first flowpath control means 96 operative to shut off the flowpath to establish blockage between the accumulator 3 and the blood tank 2 when the piston rod is on a downward stroke (the pressure plate is moved down). When the piston rod is on an upward stroke (the pressure plate is moved up), the controller 95 controls the second flowpath control means 97 operative to shut off the flowpath to prevent blood entry into the accumulator 3 from a downstream side.

Figure 17:
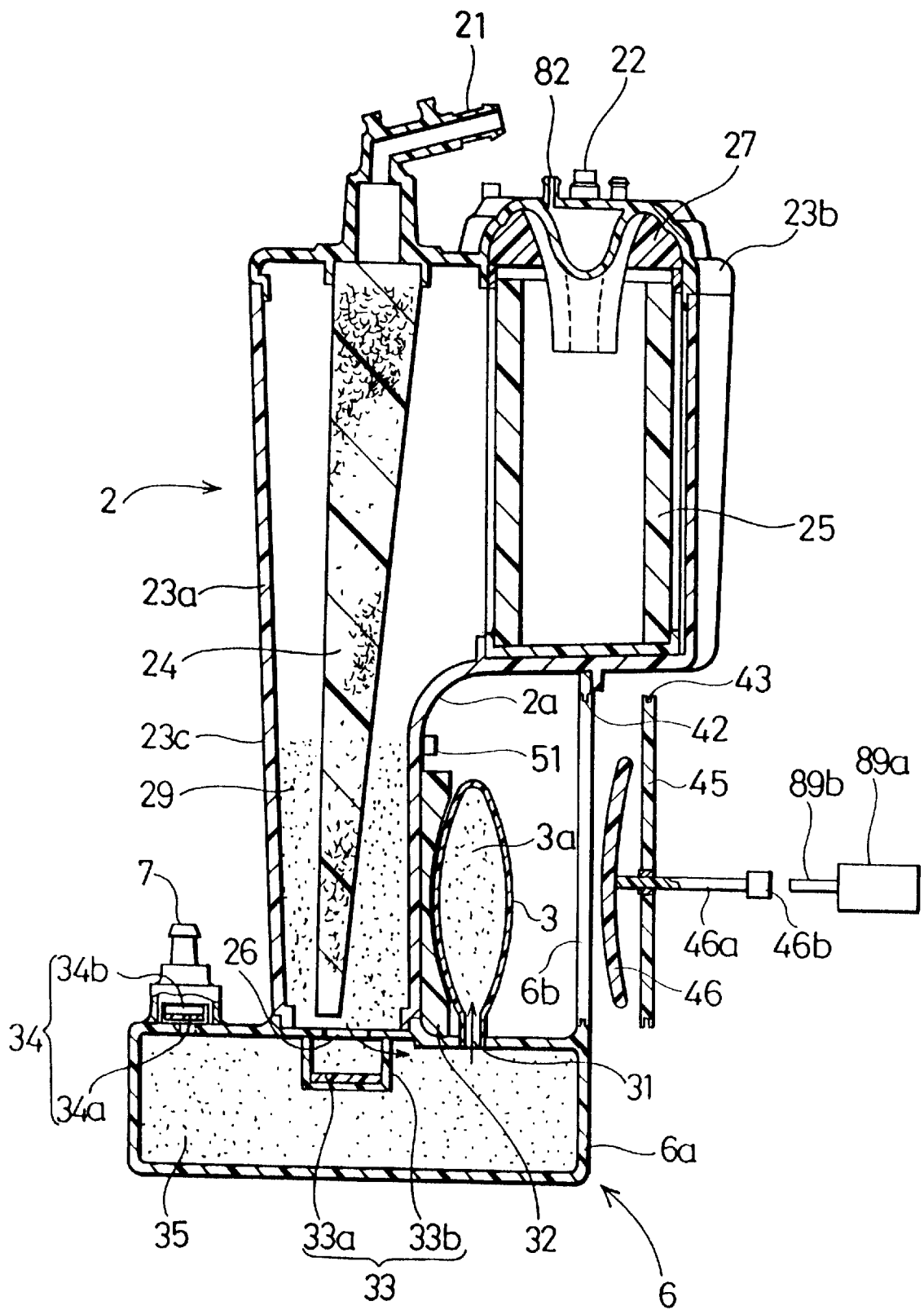
FIG. 17 is a cross-sectional view of a blood reservoir according to a still further embodiment of the invention.

FIG. 17 shows a blood delivery apparatus according to a still further embodiment of the invention.

The basic construction is the same as the apparatus shown in FIG. 11. The blood delivery pumping means is removably attached to the blood reservoir since the pumping means does not contact blood. The blood reservoir 10 of this embodiment does not have a pumping means as an integral component and instead, has an attachment therefor. More particularly, a blood delivery drive assembly including a plate member 45 and a pumping means is separately furnished. The plate member 45 is attached to an opening 6b in the channel section housing 6a. The plate member 45 is provided with the engagements 43 and the channel section housing 6a is provided with the engagements 42. Through these engagements, the plate member 45 (or the blood delivery drive assembly) is tightly attached to the reservoir 10 so that the assembly may not be readily removed. The blood delivery drive assembly includes the pumping means in the form of a curved press plate 46 which is secured to one end of a drive shaft 46a extending through the plate member 45. The drive shaft 46a at another end is provided with a piston rod connector 46b through which the drive shaft 46a is removably connected to a piston rod 89b of a cylinder 89a. When the piston rod 89b is moved to the left in FIG. 17, the pressure plate urges and collapses the accumulator bag 3 to reduce its internal volume to displace blood therefrom. The thus displaced blood flows to an artificial lung side. The cylinder 89a is coupled to a hydraulic pressure generator (not shown) for driving the piston rod.

Figure 18:
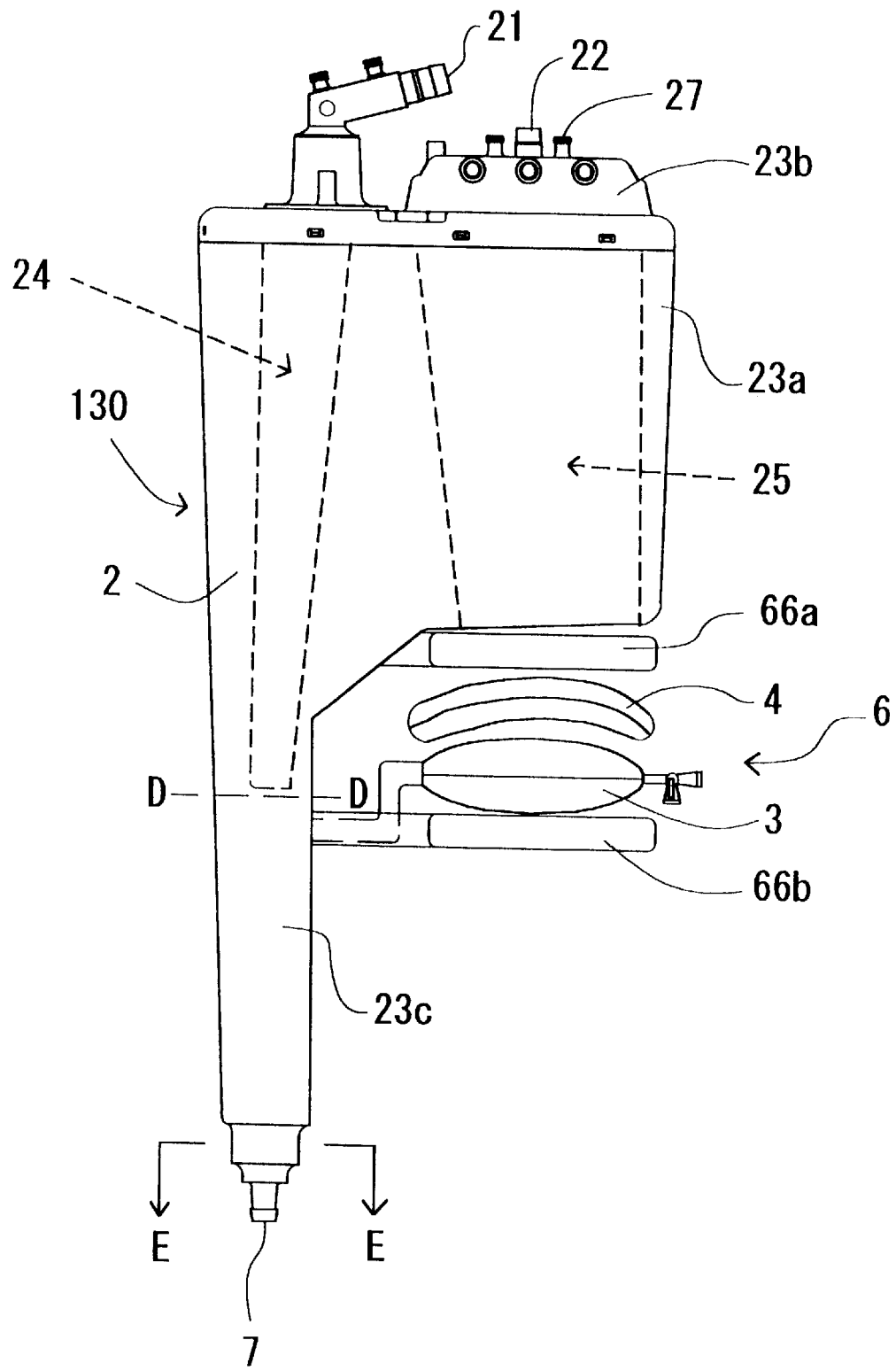
Figure 20:
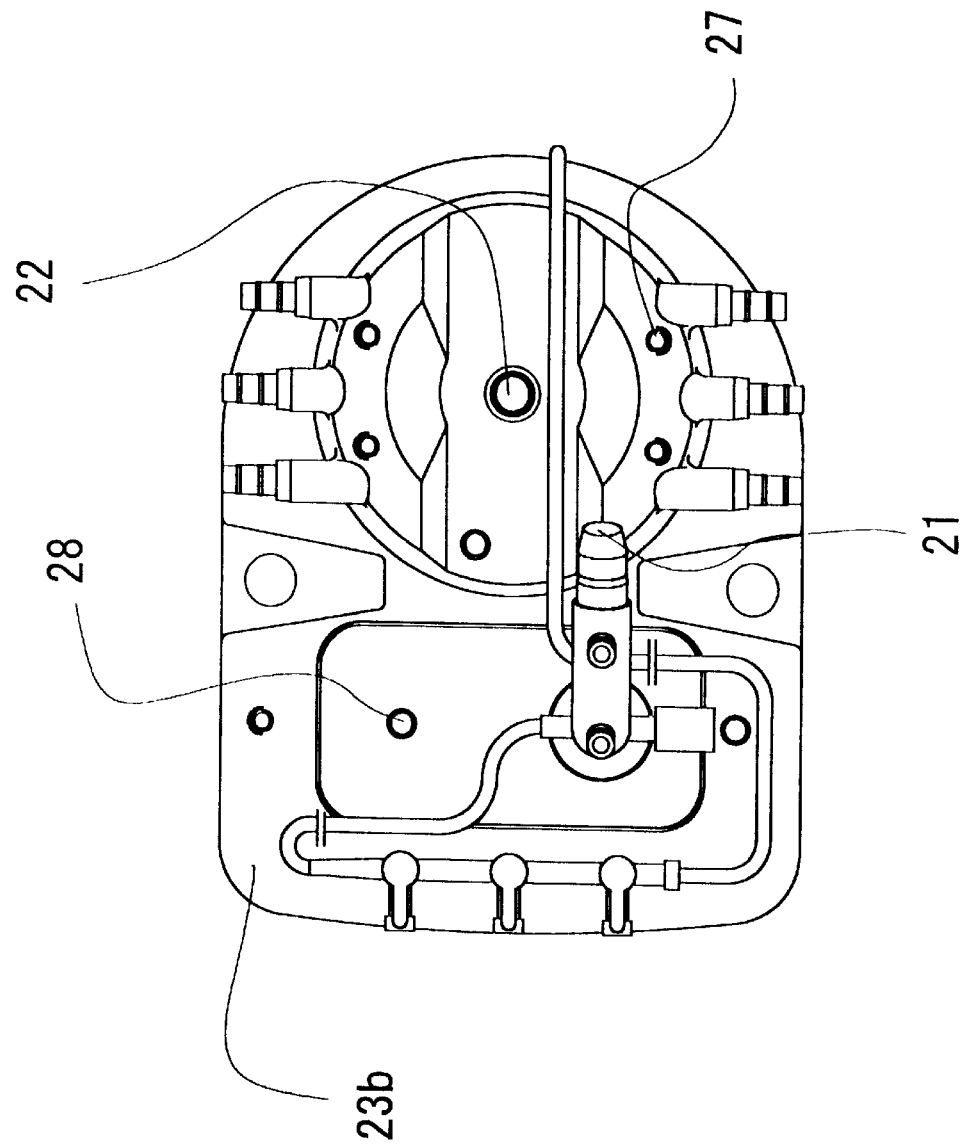
Figure 23:
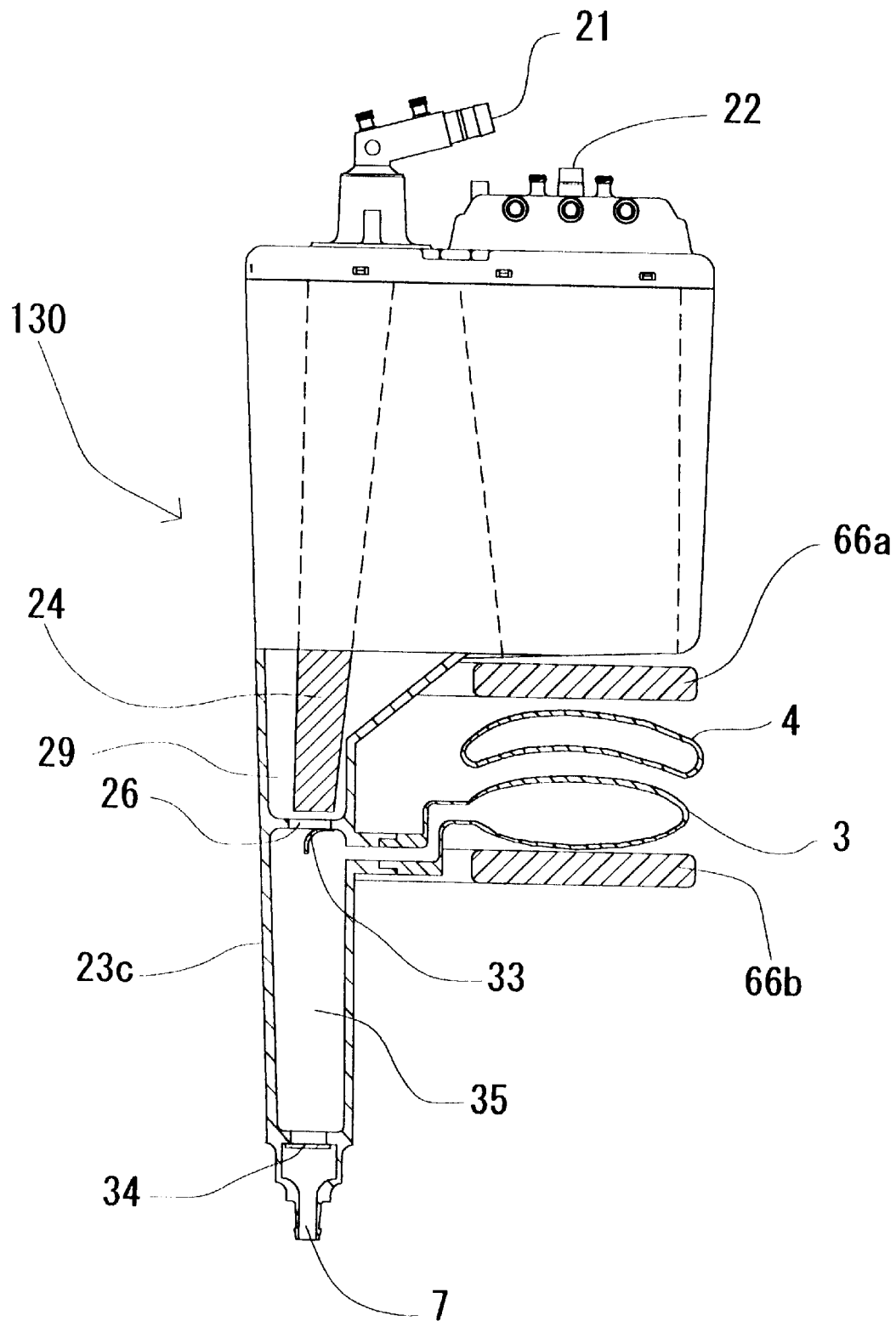
Figure 24:
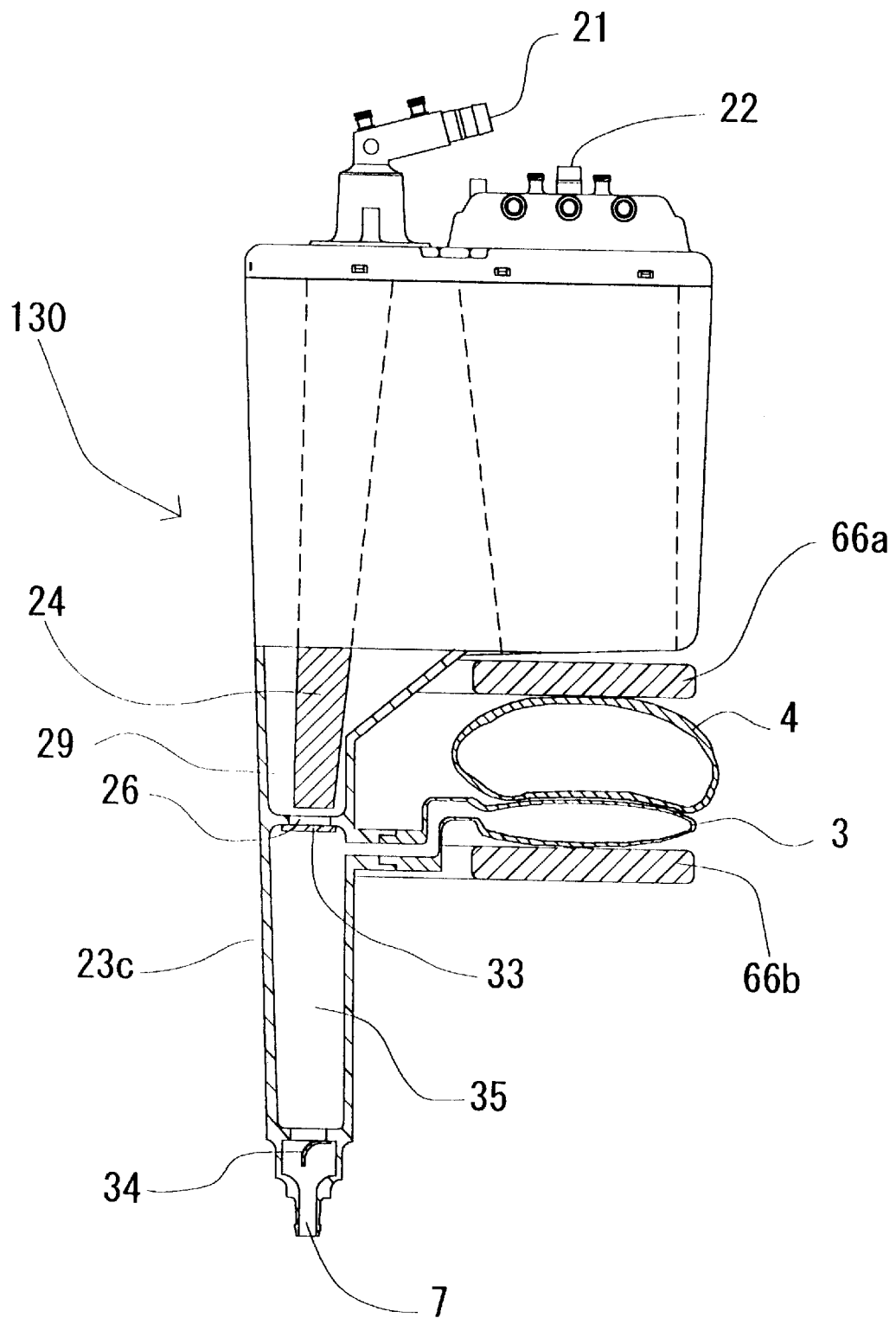

Referring to FIGS. 18 to 24, there is illustrated a blood reservoir 130 according to a further embodiment of the invention. FIG. 18 is a front elevational view of the blood reservoir, FIG. 19 is a left side view of the reservoir, FIG. 20 is a top view of the reservoir, FIG. 21 is a D—D cross section of FIG. 18, FIG. 22 is a E—E cross section of FIG. 18, FIG. 23 is a partial cross-sectional view of FIG. 18, and FIG. 24 is a schematic view for explaining the operation of the blood reservoir of FIG. 18.

The basic construction of the blood reservoir of this embodiment is the same as the reservoir of FIGS. 1 to 9. The difference is the shape and arrangement of a accumulator and blood delivery pumping means and the shape of valves.

As in the first-mentioned embodiment, a blood reservoir 130 includes a blood tank 2 and a blood delivery instrument 6 which includes a blood accumulator 3 and a pumping means 4.

The blood tank 2 includes a tank housing consisting of a main body 23a and a cover 23b both made of rigid resin. The cover 23b is fitted on the top end of housing main body 23a so as to cover the upper opening of the main body 23a as shown in FIGS. 18 and 19. The cover 23b has blood flow inlets 21 and 22 and air vents 27 and 28 as shown in FIG. 20. The blood flow inlet 22 is connected to a cardiotomy line for conveying blood from the operation area. The blood flow inlet 21 is connected to a drainage line for conveying blood from a drainage cannula inserted into the heart ascending/descending veins of the patient. Received in the housing main body 23a are a cardiotomy blood filter 25 for filtering the blood incoming from the inlet 22 and a venous blood filter 24 for filtering the blood incoming from the inlet 21.

The housing main body 23a has a downward projection 23c and a blood outlet 26 formed in the bottom of the projection 23c. Defined within the blood tank housing is a blood reserve portion 29 for temporarily reserving blood.

Attached at the bottom of the blood tank 2 is blood delivery instrument 6 which includes a pair of retainer plates 66a and 66b fixedly secured to the tank housing 23a. The blood delivery instrument 6 further includes the blood accumulator 3 and the blood delivery pumping means 4 received between retainer plates 66a and 66b.

A blood channel section 35 is defined by blood delivery instrument 6 near its bottom and provides fluid communication between the blood reserve portion or the interior 29 of the blood tank 2 and the blood accumulator 3. Disposed in proximity to blood flow outlet 26 of blood tank 2 is a first check valve 33 which permits blood passage from the tank 2 to the channel section 35 (and hence, the accumulator 3), but restrains blood passage in the opposite direction. This first check valve 33 functions as a flowpath control member for shutting off communication between the tank 2 and the accumulator 3 during operation of the pumping means 4. The blood deliver instrument 6 is provided with a blood exit port 7 in communication with the blood channel 35. Disposed in proximity to blood exit port 7 is a second check valve 34 which permits blood passage from the channel 35 (and hence, accumulator 3) to a downstream side, but restrains blood passage in the opposite direction. This second check valve 34 functions as a flowpath control member for shutting off blood flow from the downstream side into the accumulator side (and hence, blood channel side) when pumping means 4 is inoperative.

Each check valve 33, 34 has a disc-shaped movable valve body 33a, 34a a part of which is secured to the housing. Preferably the movable valve body is slightly lighter than the specific gravity of blood and a hardness of about 3 to 7 on Shore A scale. For example, the valve body is made of styrene elastomer oil gel or silicone gel and has a thickness of about 1 to 5 mm.

The blood accumulator 3 is in fluid communication with the blood channel section 35 via a blood passage port 31 which is located below or at the lower end of the accumulator 3 and formed at a position of the same height as the lower end of the blood reserve portion 29 of the blood tank 2 in a vertical direction. The blood accumulator 3 includes a tubular portion which extends a certain distance vertically upward and parallel to the projection 23c of the blood tank 2 and bends in a horizontal direction and a bag or bladder portion which is connected to the tubular portion and extends horizontally. The bag portion of the blood accumulator 3 is formed as a bag of flexible resin. When blood flows into the bag portion, it inflates in a height direction of the blood tank 2. If the surface of blood in the blood tank 2 is below the uppermost end of the interior of the blood accumulator 3, an amount proportional to the blood surface in the tank 2 of blood flows into the blood accumulator 3. Inversely, since the maximum containment amount of the blood accumulator 3 remains unchanged, even if the surface of blood in the blood tank 2 is above the uppermost end of the interior of the blood accumulator 3, this maximum containment amount of blood flows into the blood accumulator 3.

Since the uppermost end of the interior of the blood accumulator 3 shown in FIG. 18 is positioned at a lower level than the embodiment shown in FIG. 2, the range (blood surface height range) where the blood accumulator 3 is pressure sensitive (blood surface sensitive) is narrower. In the range where blood accumulator 3 is pressure sensitive, if the volume of blood in the tank 2 is above a predetermined value (that is, the surface of blood in the tank 2 is above the uppermost end of the interior of the accumulator 3 in the illustrated embodiment), the maximum containment amount of the accumulator 3 becomes preferential to the pressure exerted by the volume of blood in the tank 2 so that the accumulator 3 contains the maximum containment amount of blood. If the volume of blood in the tank 2 is below the predetermined value (that is, the surface of blood in the tank 2 is below the uppermost end of the interior of the accumulator 3 in the illustrated embodiment), the accumulator 3 exerts a pressure sensitive function to contain blood in an amount proportional to the volume of blood in the tank 2 (or the height of the blood surface in the tank 2). Thus, the accumulator 3 has the function of automatically containing blood in an amount proportional to the volume of blood in the tank 2 when the volume of blood in the tank 2 is below the predetermined value.

For the accumulator 3 and the pumping means 4, those described in the first-mentioned embodiment are useful. It is understood that in accordance with the configuration of the accumulator 3, the pumping means 4 is also configured so as to extend horizontally with respect to the blood tank 2. When an operative fluid is admitted into the pumping means 4, it is inflated to compress accumulator 3 in cooperation with the pair of retainer plates 66a, 66b, thereby displacing blood from the accumulator 3. As seen from FIG. 19, the blood reservoir of this embodiment also has two sets of accumulators 3 and pumping means 4. The blood channel 35 is also partitioned into two blood channels 35a and 35b which are not in fluid communication with each other, as shown in FIG. 21. Unlike the embodiment shown in FIG. 8, two blood channels 35a and 35b are provided with blood outflow ports 7a and 7b, respectively, as shown in FIG. 19.

Figure 25:
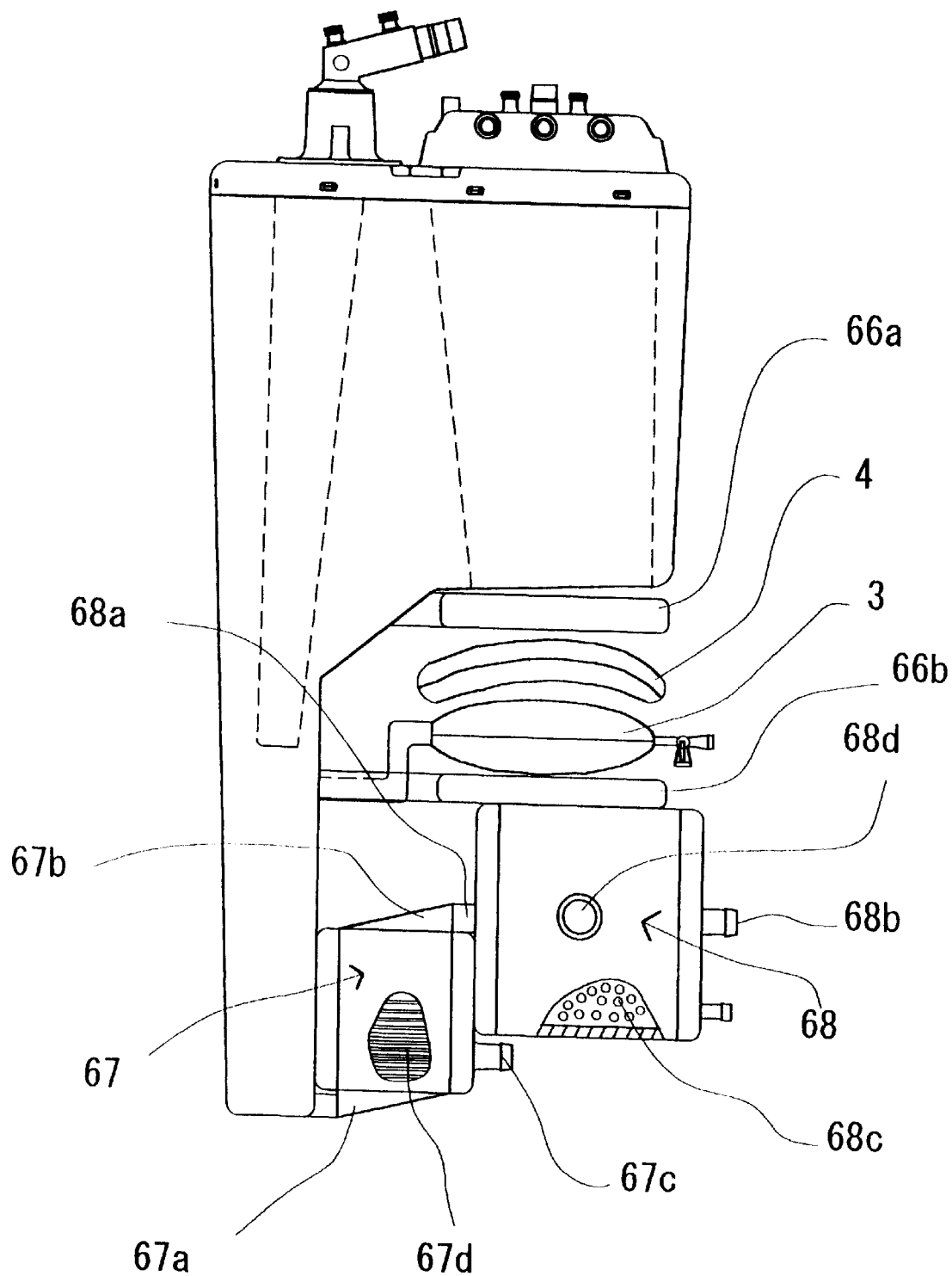
FIG. 25 is a front view of a blood reservoir having a heat exchanger and an artificial lung integrated therewith.

FIG. 25 shows a blood reservoir having a heat exchanger and an artificial lung integrated therewith. The basic construction of this blood reservoir is the same as in FIGS. 18 to 24 except that the blood channel section is vertically elongated and the blood outflow port is horizontally oriented so that a heat exchanger 67 and an artificial lung 68 may be mounted. The description of the basic construction is omitted and only the arrangement of the heat exchanger 67 and the artificial lung 68 is described.

The artificial lung 68 used herein is a heat exchanger built-in hollow membrane fiber type artificial lung as shown in FIG. 25. The heat exchanger 67 is located upstream and artificial lung 68 is located downstream.

The heat exchanger 67 includes a housing provided with two blood inlet ports 67a (only one shown) connected to two blood outlet ports of the blood reservoir and blood outlet ports 67b as well as an inlet port 67c and an outlet port (not shown) for a heating medium. A multiplicity of heat exchanging tubes 67d are received in the housing and at opposite ends tightly secured to the housing through partitions (not shown). In this heat exchanger, blood passes through the tubes and the heating medium passes outside the tubes. The tubes may be made of metals having high heat conductivity, for example, stainless steel, aluminum and copper or resins. The tubes preferably have an inner diameter of 0.1 to 10 mm, more preferably 0.5 to 5 mm. Usually about 100 to 2,000 tubes are assembled as a bundle which is received within the housing.

The heat exchanger used herein is not limited to the illustrated type wherein blood passes inside the heat exchange tubes (internal blood perfusion type). A heat exchanger of the type wherein blood passes outside the heat exchange tubes (external blood perfusion type) is also useful.

The artificial lung 68 includes a housing having a blood inlet port 68a and a blood outlet port 68b. A bundle consisting of a multiplicity of gas exchanging hollow membrane fibers 68c is received in the housing. The hollow membrane fibers 68c at opposite ends are tightly secured to the housing through partitions (not shown). The housing is provided with a first header opposed to one partition and having a gas inlet port 68d and a second header opposed to the other partition and having a gas outlet port (not shown). The hollow membrane fibers have microscopic pores in the membrane wall through which oxygen is added to blood and carbon dioxide is removed from blood. The hollow membrane fibers used herein generally have a gage of 5 to 80 $\mu$m, preferably 10 to 60 $\mu$m, a porosity of 20 to 80%, preferably 30 to 60%, a pore size of 0.01 to 5 $\mu$m, preferably 0.01 to 1 $\mu$m, and an inner diameter of 100 to 1,000 $\mu$m, preferably 100 to 300 $\mu$m.

Hydrophobic polymers are often used to form the hollow membrane fibers. Exemplary hydrophobic polymers include polypropylene, polyethylene, polytetrafluoroethylene, polysulfone, polyacrylonitrile and cellulose acetate. Preferred among others are polyolefin resins, especially polypropylene. More specifically, hollow membrane fibers of polypropylene in which micropores are formed by a drawing or solid-liquid phase separation method are desirable. Usually 10,000 to 80,000 hollow membrane fibers are distributed over the transverse cross section of the housing.

In this artificial lung, blood passes outside the hollow membrane fibers while gas passed through the hollow membrane fibers. An artificial lung of the type wherein blood passes through the hollow membrane fibers (internal blood perfusion type) is also acceptable. When the blood delivery instrument mentioned above produces a pulsative flow of blood, the use of an artificial lung of the hollow membrane fiber type is preferred because it little absorbs the pulsative flow. The use of an artificial lung comprising porous flat membranes is less desirable because the flat membranes are deformed to a large extent to dampen the pulsation.

The order of a heat exchange and an artificial lung may be reversed if desired.

Figure 27:
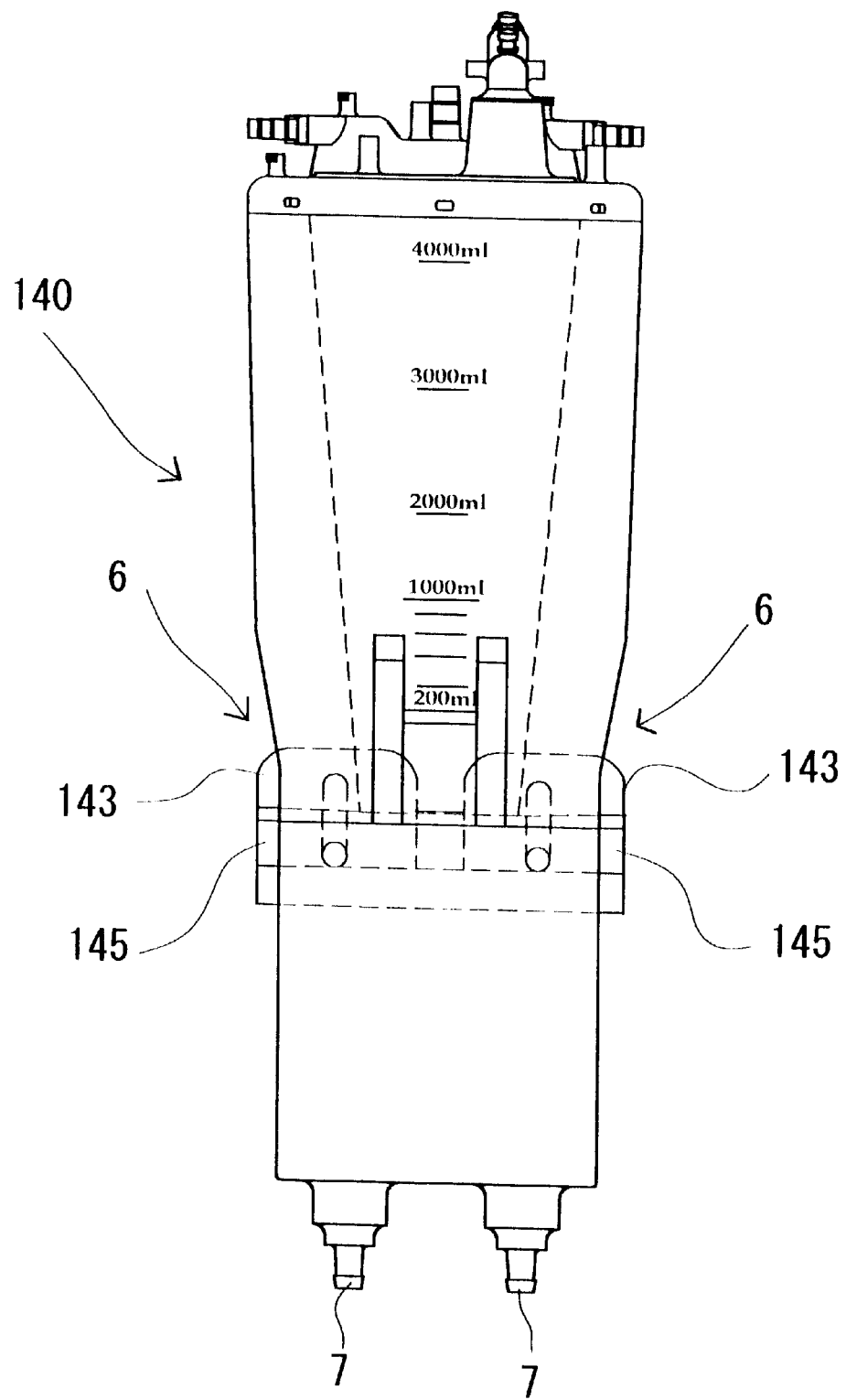
Figure 28:
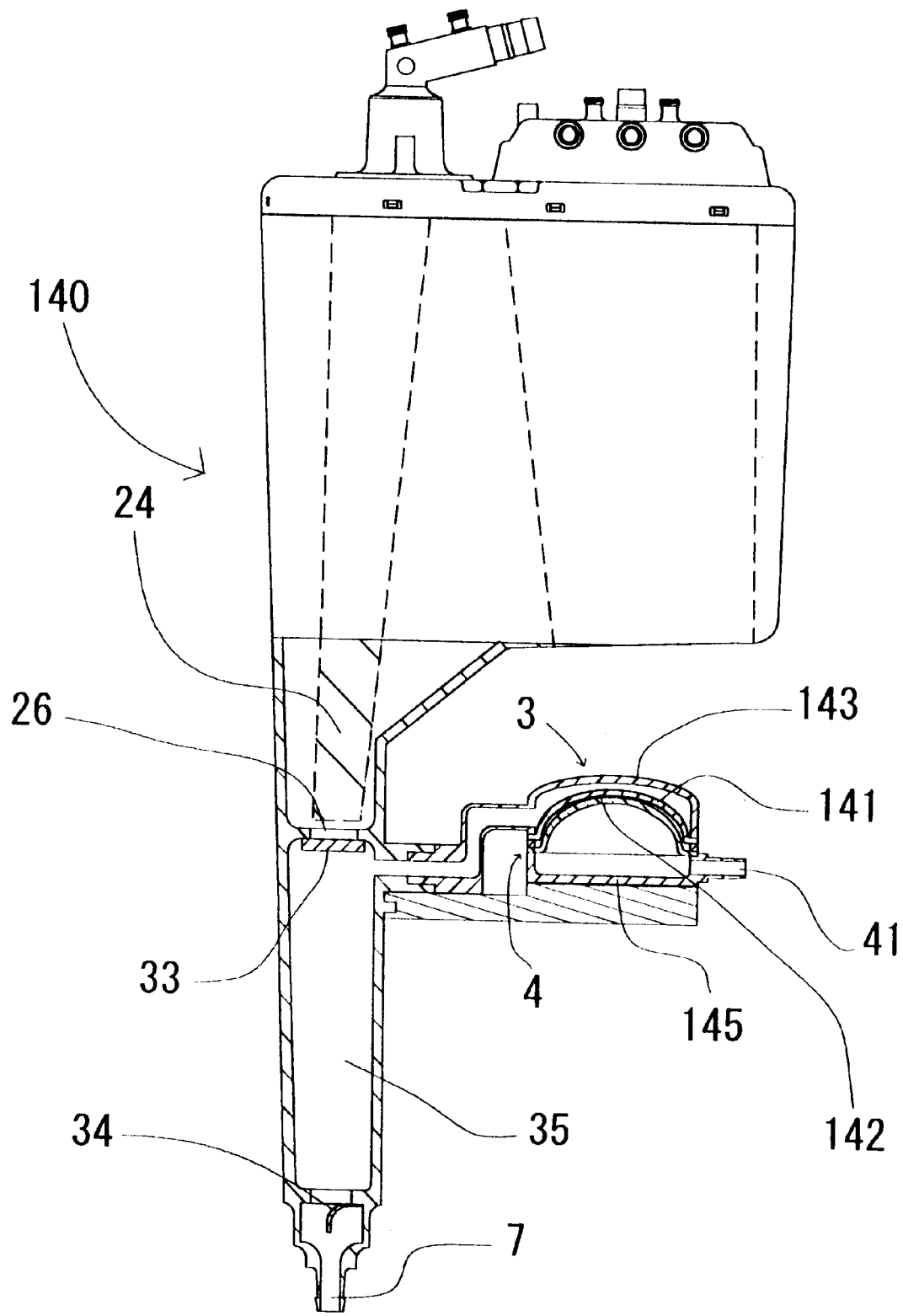

FIGS. 26 to 28 shows a blood reservoir 140 according to a still further embodiment of the invention. FIG. 26 is a front elevation of the blood reservoir; FIG. 27 is a side view of the reservoir; and FIG. 28 is a partial cross-sectional view of the reservoir of FIG. 26. Since the basic construction of this blood reservoir is the same as in FIGS. 18 to 24 except for the blood delivery mechanism, the description of common components is omitted herein.

The blood reservoir 140 of this embodiment includes a blood accumulator side housing 143 of a substantially fixed volume in communication with a blood channel section 35 and a blood accumulator side movable membrane 141 of flexible material disposed below the housing for constructing a blood accumulator 3. Also included are a pumping side housing 143 of a substantially fixed maximum volume in communication with a fluid port 41 and a blood delivery pumping side movable membrane 142 of flexible material disposed above the housing for constructing a blood delivery pumping means 4. The blood accumulator side housing 143 and the pumping side housing 145 are combined and fixedly secured such that the movable membranes associated therewith may face in contact (substantially plane contact), thereby constructing a blood delivery instrument 6. Since the movable membrane 141 on the blood accumulator side and the movable membrane 142 on the pumping means side are separate, the movable membrane on the blood accumulator side is not sucked when a negative pressure is created in the interior of the pumping means upon exhaustion of operative fluid. This prevents the accumulator itself from carrying out blood suction and thus eliminates any influence on the pressure sensitivity of the accumulator. The movable membrane on the accumulator side is one free of self-shape-recovery ability.

Figure 29:
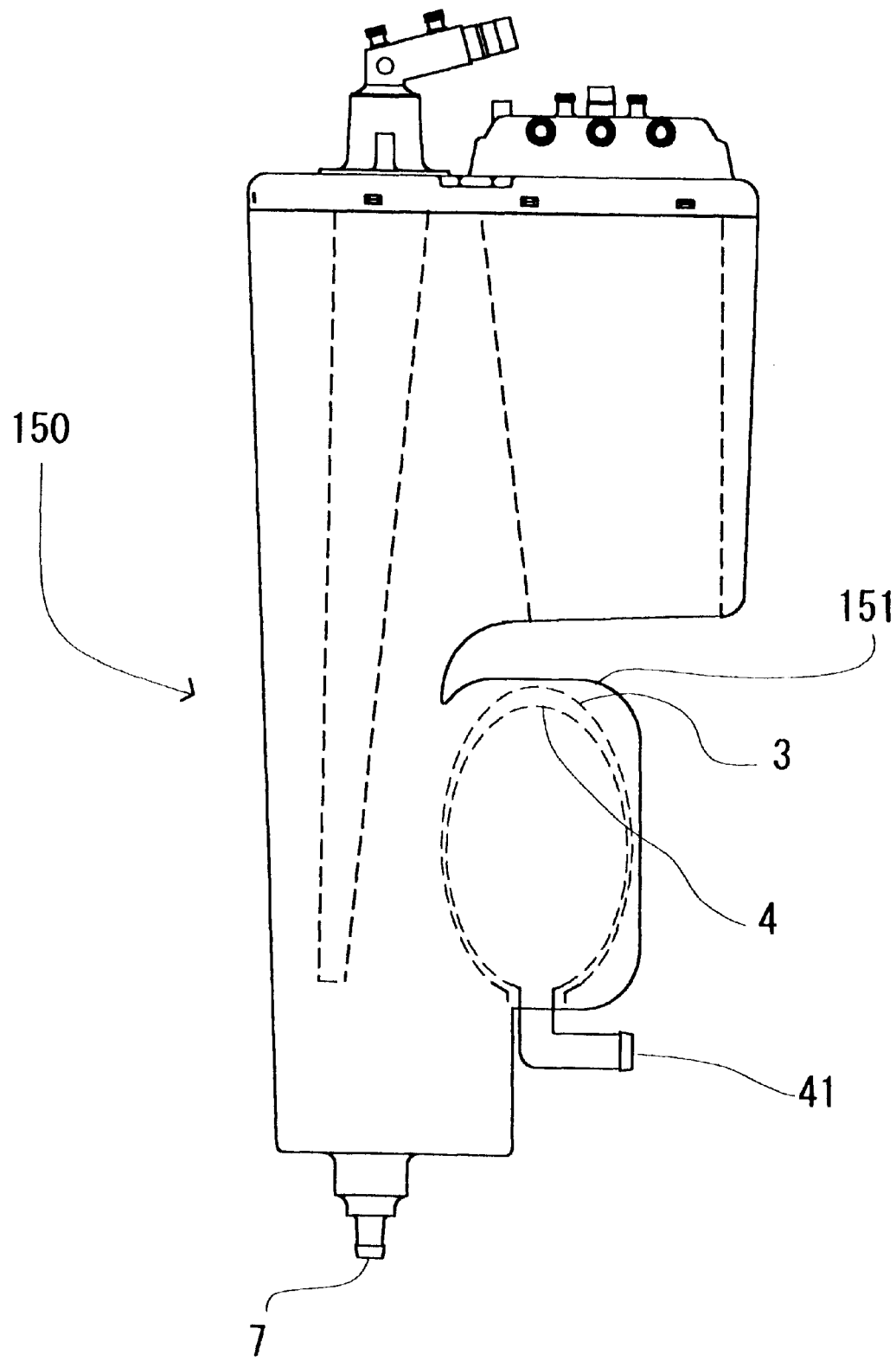
Figure 30:
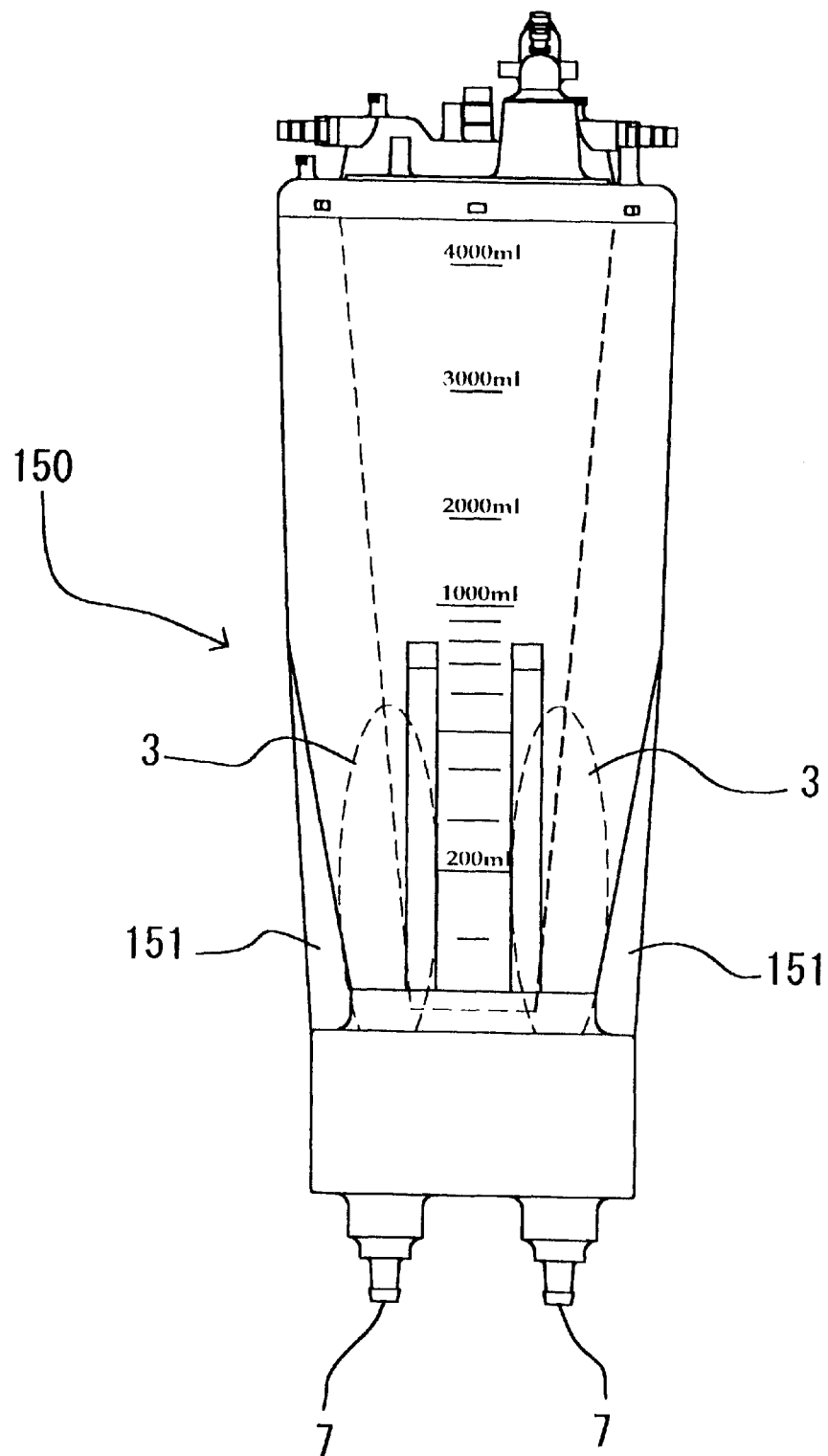
Figure 32:
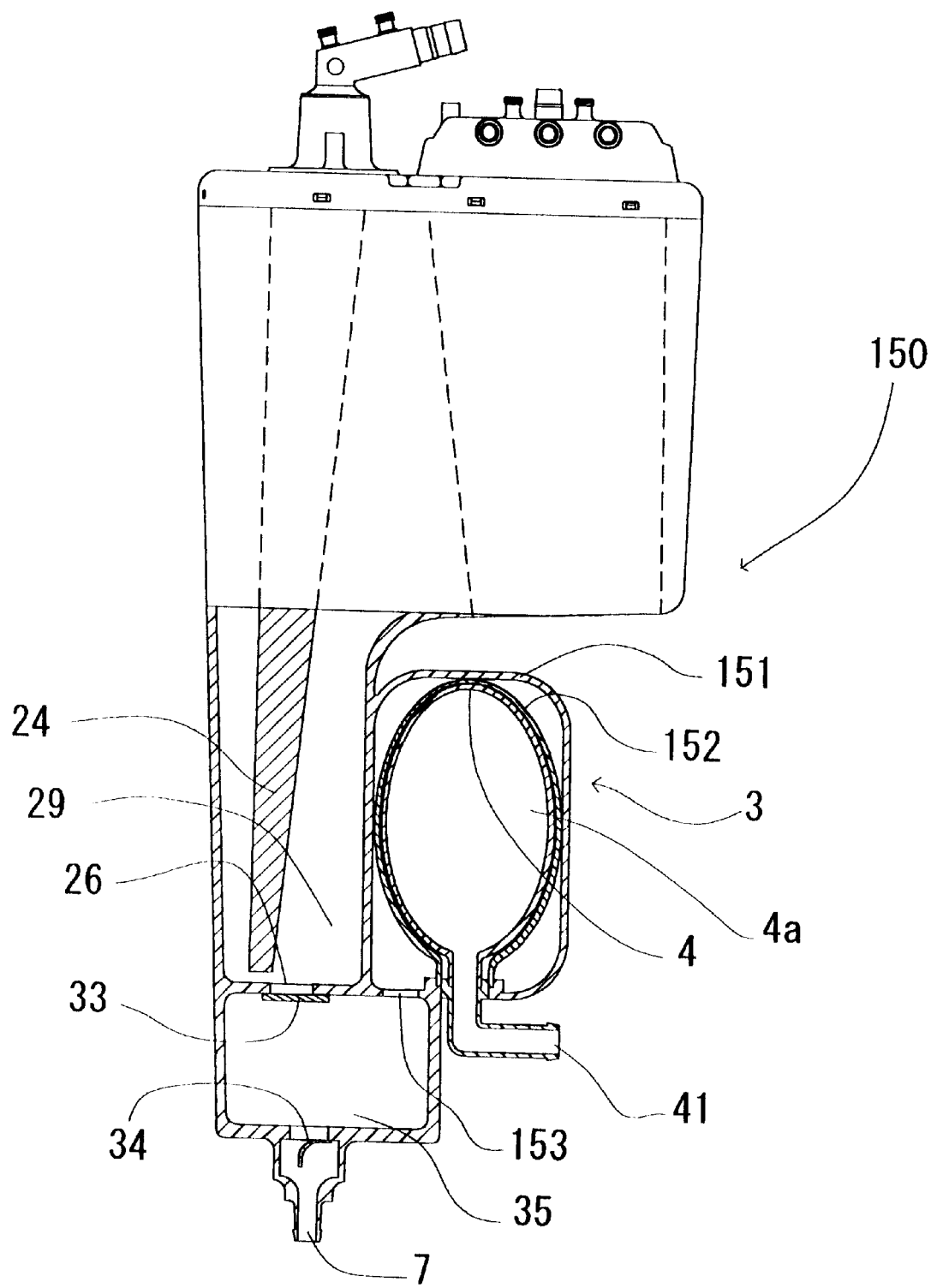

FIGS. 29 to 32 shows a blood reservoir 150 according to a still further embodiment of the invention. FIG. 29 is a front elevation of the blood reservoir; FIG. 30 is a side view of the reservoir; FIG. 31 is a partial cross-sectional view of the reservoir; and FIG. 32 is a schematic view for explaining the operation of the blood reservoir of FIG. 29. Since the basic construction of this blood reservoir is the same as in FIGS. 18 to 24 except for a blood delivery mechanism, the description of common components is omitted herein.

The blood reservoir 150 of this embodiment includes a blood accumulator side housing 151 in communication with a blood channel section 35 by a hole 153 and having a limited maximum volume and a bag-shaped flexible member 152 received in the housing 151 and in communication with the exterior for constructing a blood accumulator 3. Received within the flexible bag is a blood delivery pumping means 4. The blood delivery pumping means 4 used herein is preferably a flexible bag formed of flexible resin as used in the previously mentioned blood accumulator member and defining a space 4a therein. That is, the blood delivery instrument of this blood reservoir 150 has a dual bag structure. The space 4a defined in the blood delivery pumping means 4 is in fluid communication with a fluid passage port 41 disposed at a lower end thereof. On use, the port 41 is connected to a blood delivery fluid feed unit and a compressor built in the fluid feed unit operates to discharge a fluid (either liquid or gas) into and out of the interior space of the pumping bag 4 whereby pumping bag 4 undergoes repetitive inflation and contraction. Upon contraction, the pumping bag 4 is in contact with the accumulator bag 3, but does not force accumulator bag 3 as shown in FIG. 31. Upon inflation, pumping bag 4 inflates to exert an outward pressure against the flexible bag of the accumulator as shown in FIG. 32, reducing the volume of the accumulating bag to displace blood out of the accumulating bag.

Since the deformable portion (flexible bag) of the accumulating member and the deformable portion (flexible bag) of the pumping means are separate in this blood delivery instrument too, the movable membrane on the blood accumulator side is not sucked when a negative pressure is created in the interior of the pumping means upon exhaustion of operative fluid. This prevents the blood accumulator itself from carrying out blood suction and thus eliminates any influence on the pressure sensitivity of the blood accumulator. The movable membrane on the blood accumulator side is one free of self-shape-recovery ability.

Figure 16:
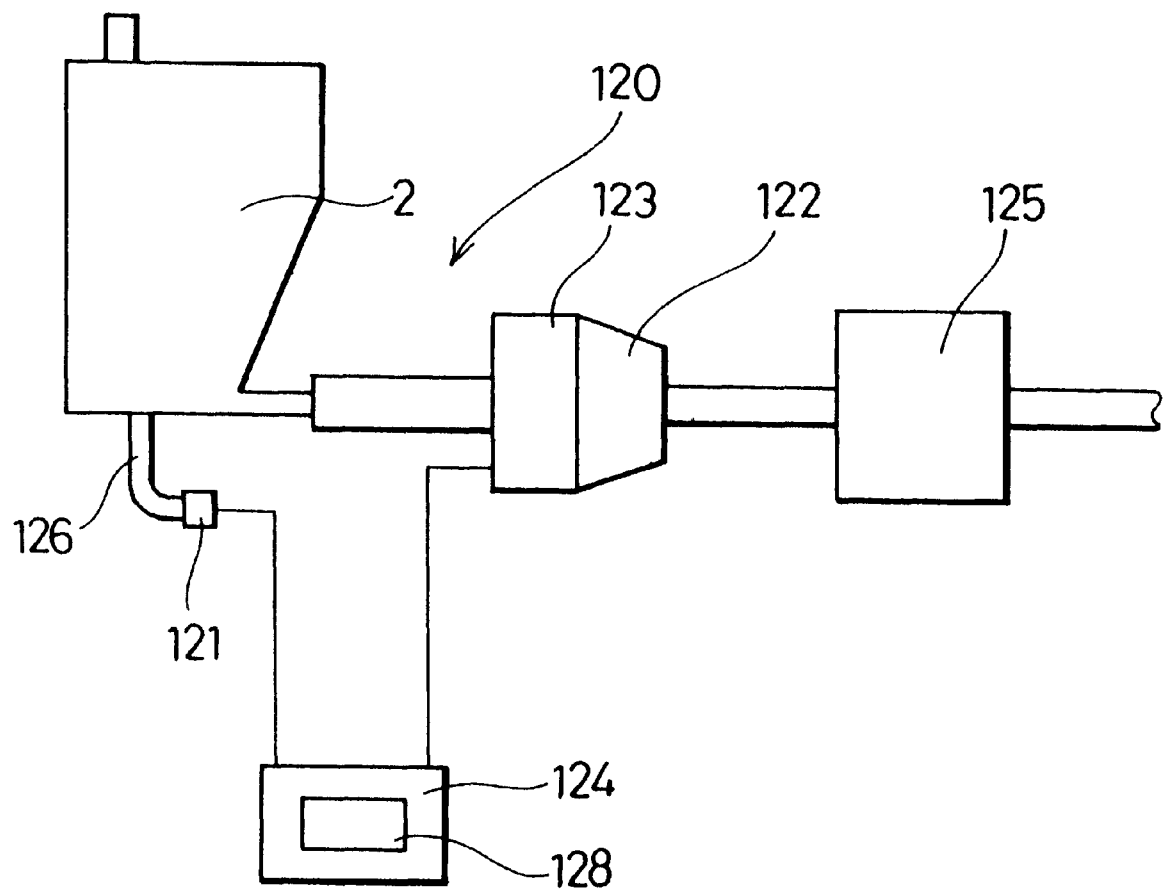
FIG. 16 is a schematic view of a blood delivery apparatus according to a further embodiment of the invention.

Next, the blood delivery apparatus shown in FIG. 16 is described.

The blood delivery apparatus 120 includes a sensor 121 attached to blood tank 2, a blood feed pump 122 connected to the outlet of the tank 2, a motor 123 associated with pump 122 for operating it, and a controller 124 electrically connected to the sensor 121 and the motor 123. The controller 124 has a blood delivery rate regulating function of delivering blood in an amount proportional to the volume of blood reserved in the blood tank 2 when the volume of blood reserved in the blood tank 2 is below a predetermined value.

The sensor 121 is attached to an end of a tube 126 connected to the bottom of the tank 2 so that the sensor is in fluid communication with the tank. A pressure transducer is preferred as the sensor used herein. It is also acceptable to use a load cell to directly measure the weight of the blood tank.

The blood feed pump 122 may be a constant pressure pump, roller pump or peristaltic pump, with the constant pressure pump being preferred. In the illustrated embodiment, a constant pressure pump is used as the blood feed pump. The constant pressure pump includes a centrifugal pump, turbine pump and screw pump.

The sensor 121 detects the pressure at the bottom of the tank 2 and delivers detection signals at suitable time intervals (for example, of about 10 seconds) to the controller 124. It is understood that the pressure at the bottom of the tank 2 is in proportion to the volume of blood reserved in the tank 2. The controller 124 includes a switch panel 128 which includes a flow rate input switch and a switch for inputting a residual blood volume for switching to a flow rate regulating mode. The controller 124 has a residual blood volume computing function of converting a signal from the sensor 121 into a value X corresponding to the residual volume of blood in the blood tank 2. The controller 124 also has a function of comparing a residual blood volume value A (liter) input from the residual blood volume input switch with the actual residual blood volume value X (liter). It maintains the normal blood delivery mode if A<X, but switches into a blood delivery rate regulating mode to the control feed pump 122 in that mode if A>X. That is, the flow rate of blood to be delivered is regulated after the actual volume X of blood in the blood tank 2 is below the preset residual blood volume value A. Specifically, provided that the flow rate input switch inputs a flow rate of B liter/min., the control is made so as to provide a flow rate of blood delivered Y=B/A×X. The invention is not limited to this method of controlling the blood flow rate in a linear proportional manner. For example, control is made such that the blood flow rate changes in a curvilinear proportion as given by $Y=B/A^2 \times X^2$. If A<X is resumed, transition from the blood delivery rate regulating mode to the normal blood delivery mode occurs to resume blood delivery in the preset flow rate C.

There has been described a blood reservoir comprising a blood tank, a blood accumulator connected in fluid communication with an outlet of the tank for receiving blood from the tank, and a pumping means for driving the accumulator to displace blood out of the accumulator for blood delivery purpose. The accumulator is adapted to store blood in an amount proportional to the volume of blood in the tank when the volume of blood in the tank is reduced below a predetermined value. The pumping means operates to intermittently displace blood out of the accumulator. The pumping means is able to regulate the amount of blood displaced out of the accumulator. Therefore, when the volume of blood in the tank is reduced below the predetermined value by an octopus which the blood inflow volume to the tank decreases, the blood is delivered in an amount proportional to the residual blood volume in the tank. In other words, it becomes that the blood delivery volume from the tank is substantially same the blood inflow volume to the tank after the volume of blood in the tank is reduced below the predetermined value.

As the residual blood volume is reduced, the amount of blood delivered is reduced and approaches to zero, but does not equal zero. Blood delivery is maintained even in a very small amount. Since no interruption of blood delivery occurs, no blood stagnation occurs in the extracorporeal blood circulation circuit on a side downstream of the blood reservoir.

Also there has been described a blood reservoir comprising a blood tank, a blood accumulator connected in fluid communication with an outlet of the tank for receiving blood from the tank, a first check valve disposed between the tank and the accumulator for restraining blood passage to the tank side, a second check valve disposed downstream of the accumulator for restraining blood passage from a side downstream of the accumulator, and a pumping means for driving the accumulator for delivering blood out of the accumulator.

The accumulator is adapted to store blood in an amount proportional to the volume of blood in the tank when the volume of blood in the tank is reduced below a predetermined value. Since two check valves are included, a satisfactory blood flow can be formed so that the accumulator may exert its function more effectively.

Also there has been described a blood delivery instrument for use in an extracorporeal circulation circuit including a blood tank, comprising a coupling connected to the tank, a blood accumulator connected to the coupling for receiving blood from the tank, and a pumping means for driving the accumulator to deliver blood from the accumulator to a destination. The accumulator is adapted to store blood in an amount proportional to the volume of blood in the tank when the volume of blood in the tank is reduced below a predetermined value. The pumping means operates to intermittently displace blood out of the accumulator. Therefore, when the volume of blood in the tank is reduced below the predetermined value by an octopus which the blood inflow volume to the tank decreases, the blood is delivered in an amount proportional to the residual blood volume in the tank. In other words, it becomes that the blood delivery volume from the tank is substantially same the blood inflow volume to the tank after the volume of blood in the tank is reduced below the predetermined value.

As the residual blood volume is reduced, the amount of blood delivered is reduced and approaches to zero, but does not equal zero. Blood delivery is maintained even in a very small amount. Since no interruption of blood delivery occurs, no blood stagnation occurs in the extracorporeal blood circulation circuit on a side downstream of the blood delivery instrument.

Also there has been described a blood delivery instrument for use in an extracorporeal circulation circuit including a blood tank, comprising a coupling connected to the tank, a blood accumulator connected to the coupling for receiving blood from the tank, a first check valve disposed in proximity to the coupling for restraining blood passage from the accumulator to the tank side, a second check valve disposed downstream of the accumulator for restraining blood passage from a side downstream of the accumulator, and a pumping means for driving the accumulator to deliver blood from the accumulator to a destination. The accumulator is adapted to store blood in an amount proportional to the volume of blood in the tank when the volume of blood in the tank is reduced below a predetermined value. Since two check valves are included, a satisfactory blood flow can be formed so that the accumulator may exert its function more effectively.

Also there has been described a blood delivery apparatus for use in an extracorporeal circulation circuit including a blood tank, comprising a blood delivery amount regulating means for regulating the amount of blood delivered so as to be in proportion to the volume of blood in the tank when the volume of blood in the tank is reduced below a predetermined value. Therefore, when the volume of blood in the tank is reduced below the predetermined value by an octopus which the blood inflow volume to the tank decreases, the blood is delivered in an amount proportional to the residual blood volume in the tank. In other words, it becomes that the blood delivery volume from the tank is substantially same the blood inflow volume to the tank after the volume of blood in the tank is reduced below the predetermined value. As the residual blood volume is reduced, the amount of blood delivered is reduced and approaches to zero, but does not equal zero. Blood delivery is maintained even in a very small amount. Since no interruption of blood delivery occurs, no blood stagnation occurs in the extracorporeal blood circulation circuit on a side downstream of the blood delivery apparatus.

Preferred embodiments of the delivery blood storing member-equipped blood reservoir tank and the blood delivery mechanism of the present invention will be described in detail hereinafter with reference to the accompanying drawings.

Referring first to FIGS. 34 through 37, a delivery blood storing member-equipped blood reservoir tank 201 according to a preferred embodiment of the invention has a blood reservoir tank portion 202, and delivery blood storing members 203*a*, 203*b* that communicate with a blood outlet formed in the blood reservoir tank portion 202. Each of the delivery blood storing members (blood accumulators) 203*a*, 203*b* allows blood to flow out of an interior thereof when pressed from outside. The delivery blood storing members 203*a*, 203*b* reserve an amount of blood in accordance with a height of liquid surface in the blood reservoir tank portion 202 if the amount of blood in the blood reservoir tank portion 202 becomes equal to or less than a predetermined value. Each of the delivery blood storing members 203*a*, 203*b* includes a body part 241 of the delivery blood storing member which body part is formed from a hard material, and a flexible diaphragm 242 whose peripheral end is fixed to the delivery blood storing member body part 241. The diaphragms 242 are formed so as to produce substantially no self-restoring force against deformation.

The delivery blood storing members 203*a*, 203*b* reserve amounts of blood proportional to the amount of blood stored in the blood reservoir tank portion 202 when the amount of blood in the blood reservoir tank portion 202 becomes equal to or less than the predetermined value. By pressing the diaphragm 242 side of each delivery blood storing member 203*a*, 203*b* from outside, blood can be intermittently forced out of the interior of the delivery blood storing member 203*a*, 203*b*. That is, when the amount of blood in the blood reservoir tank portion 202 becomes equal to or less than the predetermined value, the delivery blood storing members 203*a*, 203*b* reserve amounts of blood proportional to the amount of blood stored in the blood reservoir tank portion 202, and blood is intermittently forced out of the delivery blood storing members 203*a*, 203*b* by pressing the diaphragms 242 thereof from outside. Therefore, if the amount of blood in the blood reservoir tank portion 202 becomes small, blood is delivered in proportionally small amounts. Thus, if the amount of blood remaining becomes small, blood delivery is maintained in small amounts. Consequently, the need to interrupt blood delivery due to a reduction in the amount of blood remaining is eliminated, so that stagnation of blood in the extracorporeal blood circulation circuit can be avoided. Furthermore, since the diaphragms 242 produce substantially no self-restoring force against deformation, the diaphragms 242 sensitively respond to changes in the amount of blood in the blood reservoir tank portion 202, thereby further ensuring reservation of amounts of blood proportional to the amount of blood remaining in the blood reservoir tank portion 202.

As described above, the delivery blood storing member-equipped blood reservoir tank 201 of this embodiment is provided with the blood reservoir tank portion 202, and the delivery blood storing members 203*a*, 203*b* that communicate with the blood outlet formed in the blood reservoir tank portion 202. Each of the delivery blood storing members 203*a*, 203*b* allows blood to flow out of an interior thereof when pressed from outside. The delivery blood storing members 203*a*, 203*b* reserve an amount of blood in accordance with a height of liquid surface in the blood reservoir tank portion 202 if the amount of blood in the blood reservoir tank portion 202 becomes equal to or less than a predetermined value. Each of the delivery blood storing members 203a, 203b includes the body part 241 of the delivery blood storing member which body part is formed from a hard material, and the flexible diaphragm 242 whose peripheral end is fixed to the delivery blood storing member body part 241. Each delivery blood storing member 203a, 203b may further has a reinforcement which covers the diaphragm 242 and whose peripheral end is fixed to the delivery blood storing member body part 241.

This construction operates similarly to the above-described construction. That is, when the amount of blood in the blood reservoir tank portion 202 becomes equal to or less than the predetermined value, the delivery blood storing members 203a, 203b reserve amounts of blood proportional to the amount of blood stored in the blood reservoir tank portion 202, and blood is intermittently forced out of the delivery blood storing members 203a, 203b by pressing the diaphragms 242 thereof from outside. Therefore, if the amount of blood in the blood reservoir tank portion 202 becomes small, blood is delivered in proportionally small amounts. Thus, if the amount of blood remaining becomes small, blood delivery is maintained in small amounts. Consequently, the need to interrupt blood delivery due to a reduction in the amount of blood remaining is eliminated, so that stagnation of blood in the extracorporeal blood circulation circuit can be avoided. Furthermore, provision of the reinforcements prevents the corresponding diaphragms 242 from being damaged during operation.

In addition to the blood reservoir tank portion 202 and the two delivery blood storing members 203a, 203b, the delivery blood storing member-equipped blood reservoir tank 201 further has blood flow passage portions 235a, 235b that connect in fluid communication between the blood reservoir tank portion 202 and the delivery blood storing members 203a, 203b, respectively. Provided outside each delivery blood storing member 203a, 203b is a drive member for directly or indirectly pressing the diaphragm 242 of the delivery blood storing member when necessary.

Figure 34:
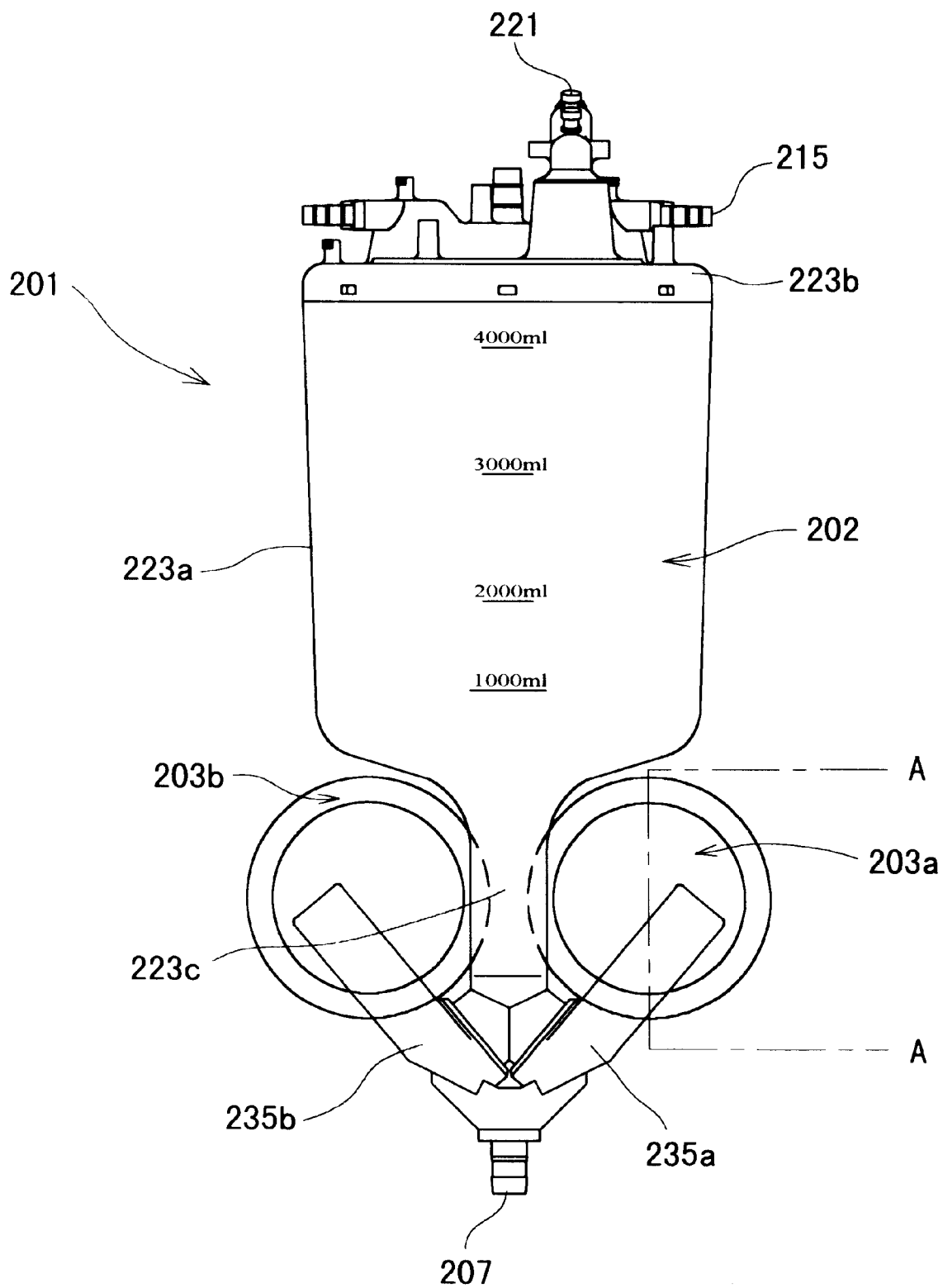
FIG. 34 is a front elevation of a delivery blood storing member-equipped blood reservoir tank according to the present invention.
Figure 36:
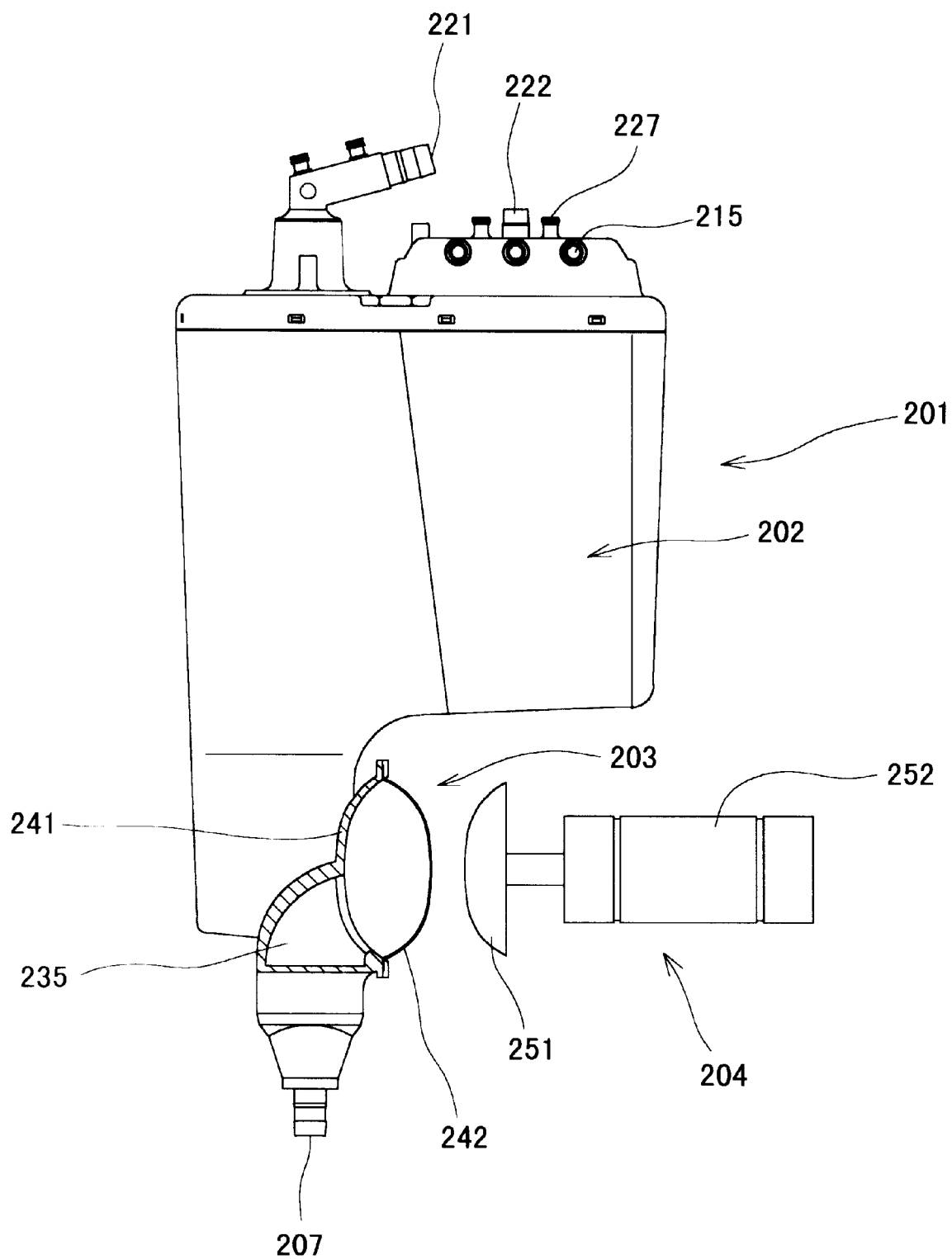
FIG. 36 is a side view of the delivery blood storing member-equipped blood reservoir tank with a fragmentary sectional view taken on line A—A of FIG. 34, together with a side view of the blood delivering drive unit.

The blood reservoir tank portion 202 has a housing, as shown in FIGS. 34–37, which is composed of a blood reservoir tank portion housing main body 223a and a lid body 223b that are formed from a hard resin. The lid body 223b is fitted to an upper end of the housing main body 223a so as to cover an upper opening of the housing body 223a. The lid body 223b has blood inlets 221, 222 and an air discharge opening 227 as shown in FIGS. 34 and 35. The blood inlet 222 is connected to a cardiotomy line for conveying blood from an operation field. The blood inlet 221 is connected to a blood drainage line for conveying blood from a drainage cannula inserted into the heart ascending/descending veins of the patient. Disposed in the housing main body 223a are a cardiotomy blood filter 225 for filtering blood incoming from the blood inlet 222 and a venous blood filter (not shown) for filtering blood incoming from the blood inlet 221.

The housing main body 223a has a downward projected portion 223c, and two blood outlets 226a, 226b formed in a lower portion (lower end) of the projected portion 223c.

The housing main body 223a and the lid body 223b may suitably be formed from, for example, polycarbonate, acrylic resin, polyethylene terephthalate, polyethylene, polypropylene, polystyrene, polyvinyl chloride, acryl-styrene copolymers, and acryl-butadiene-styrene copolymers, and the like. Particularly preferred materials are polycarbonate, acrylic resin, polystyrene, and polyvinyl chloride.

Figure 37:
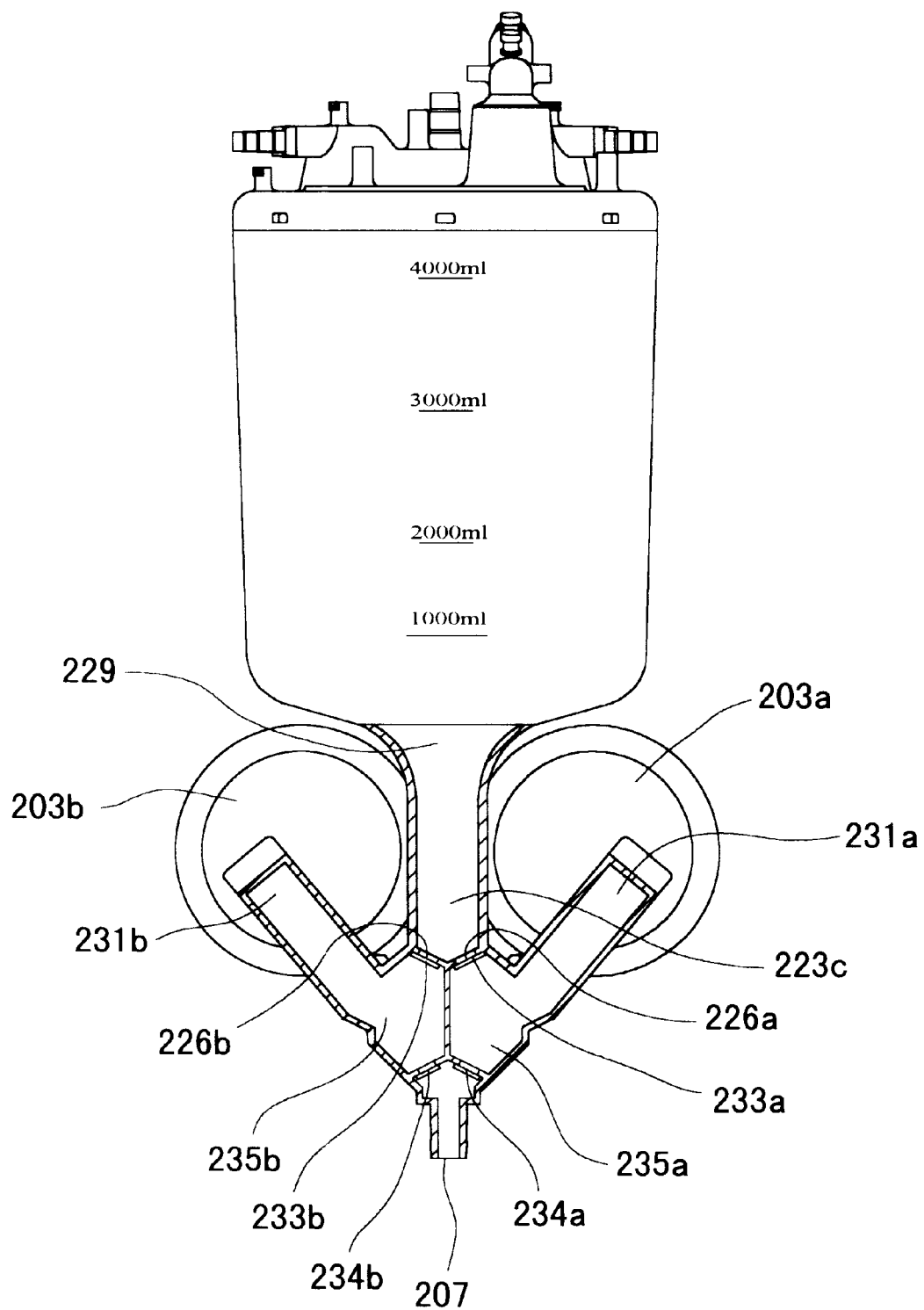
FIG. 37 is a partially cut-away front elevation of the delivery blood storing member-equipped blood reservoir tank with a fragmentary sectional view taken on line B—B of FIG. 36.

Formed in the blood reservoir tank portion housing is a blood keeping portion 229 for temporarily reserving blood as shown in FIG. 37. The blood keeping portion 229 may have any desired capacity. Normally, the capacity of the blood keeping portion 229 is about 3,000 to 5,000 ml for adults and about 1,000 to 2,500 ml for children. The housing main body 223a is preferably substantially transparent or semi-transparent so that the amount and conditions of blood reserved therein may be readily observed. The downward projected portion 223c is a narrow portion with a reduced sectional area, whereby when the amount of blood reserved decreases, the amount of blood reserved or a change in the blood amount can be correctly and readily read. The blood reservoir tank portion 202 may be a soft type blood reservoir tank portion formed from a soft resin. Then the blood reservoir tank portion 202 becomes a closed-type blood reservoir tank portion.

The blood flow passage portions 235a, 235b connecting between the blood reservoir tank portion 202 and the two delivery blood storing members 203a, 203b are formed below the blood reservoir tank portion 202. A blood flow passage portion 235a of the two separate blood flow passage portions 235a, 235b communicates only with a first delivery blood storing member 203a, and the other blood flow passage portion 235b communicates only with the other delivery blood storing member 203b. Disposed near the blood outlets 226 of the blood reservoir tank portion 202, that is, at boundary sites between the blood reservoir tank portion 202 and the blood flow passage portions 235a, 235b, are first check valves 233a, 233b that allow flow of blood from the blood reservoir tank portion 202 toward the blood flow passage portions 235a, 235b (that is, toward the delivery blood storing members 203a, 203b) and restricts (prevents) the reverse flow of blood. The first check valves 233a, 233b function as passage control members for blocking the communication between the blood reservoir tank portion 202 and the delivery blood storing members 203a, 203b during the operation of the blood delivering drive units 204 as described below. A delivery blood storing member-equipped blood reservoir tank 201 has a blood discharge opening 207 that communicates with the blood flow passage portions 235a, 235b. Provided near the blood discharge opening 207 are second check valves 234a, 234b that allow blood flow toward a side downstream from the blood flow passage portions 235a, 235b (that is, downstream from the delivery blood storing members 203a, 203b) and restricts the reverse flow of blood. The second check valves 234a, 234b function as passage control members for blocking reverse blood flow from the downstream side toward the delivery blood storing members 203a, 203b (that is, into the blood flow passage portions 235a, 235b) when the blood delivering drive unit 204 is not operated.

Each check valve 233, 234 has a disc-shaped movable valve body a portion of which is secured to the housing. Preferably, the movable valve body of each check valve has a slightly less specific gravity than blood, and a hardness of about 3 to 7 on Shore A scale. The valve bodies are preferably formed from, for example, styrene-based elastomer oil gel, silicone gel or the like, to a thickness of about 0.5 to 5 mm.

Each of the delivery blood storing members 203a, 203b includes the delivery blood storing member body part 241 formed from a hard material and the diaphragm 242 fixed at its peripheral end to the delivery blood storing member body part 241. The delivery blood storing member body part 241 has a curved inner surface, more specifically, a generally semi-spherical inner surface. The diaphragm 242 has a shape corresponding to the shape of the inner surface of the delivery blood storing member body part 241.

It is preferred that the pressure needed to deform the diaphragm 242 be equal to or less than 100 mmH$_2$O. This preferred limitation achieves sensitive response of the diaphragm 242 to changes in the amount of blood stored in the blood reservoir tank portion 202, and ensures reservation of amounts of blood proportional to the amount of blood stored in the blood reservoir tank portion 202. The pressure needed to deform the diaphragm 242 is more preferably equal to or less than 50 mmH$_2$O.

Figure 38:
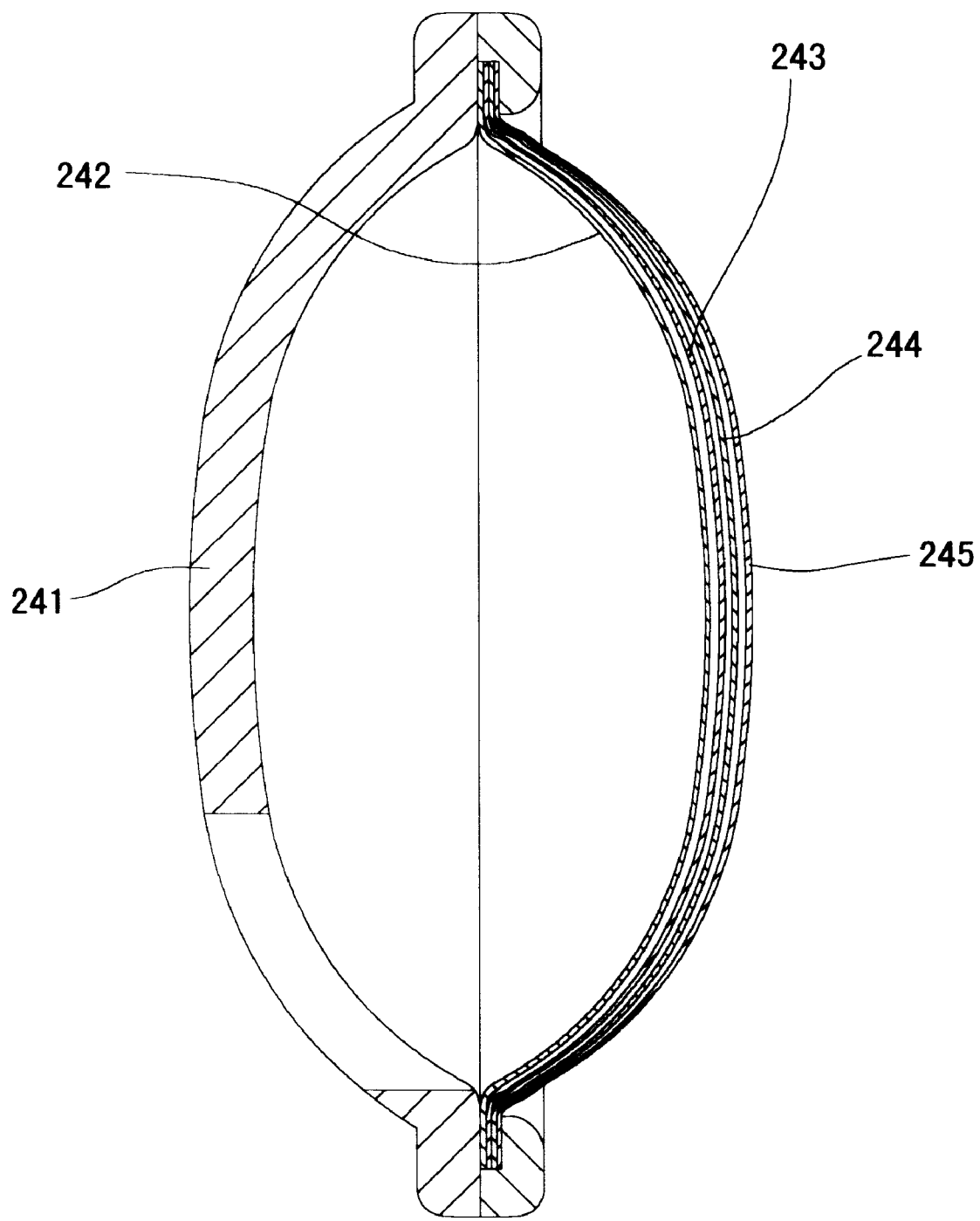
FIG. 38 is an enlarged sectional view of a delivery blood storing member.

Each of the delivery blood storing members 203a, 203b employed in this embodiment is provided with a reinforcement 243 covering the diaphragm 242 and fixed at its peripheral end to the delivery blood storing member body part 241. Preferably, the diaphragm 242 and the reinforcement 243 combined have the following properties: the pressure needed to deform the diaphragm 242 is equal to or less than 100 mmH$_2$O; the rupture strength is equal to or greater than 5 kg/cm$^2$; and the diaphragm 242 itself produces substantially no self-restoring force against deformation. Producing substantially no self-restoring force against deformation means that substantially no blood is drawn into the blood storing chamber by a self-restoring force of the diaphragm when the blood storing chamber is expanded. Each of the delivery blood storing members 203a, 203b in this embodiment is provided with the reinforcement 243 (first reinforcement), as shown in FIG. 38, for reliably preventing damages to the diaphragm 242 (first diaphragm) and ensuring blood delivery even if the diaphragm 242 should be damaged. The reinforcement 243 covers the diaphragm 242 and is fixed at its peripheral end to the delivery blood storing member body part 241. Furthermore, each delivery blood storing member 203a, 203b has a second diaphragm 244 which covers the reinforcement 243 (first reinforcement) and whose peripheral end is fixed to the delivery blood storing member body part 241, and a second reinforcement 245 that covers the second diaphragm 244 and whose peripheral end is fixed to the delivery blood storing member body part 241. The reinforcement disposed between the first diaphragm 242 and the second diaphragm 244 may be omitted.

It is preferred that the diaphragm 242 or 244 and the reinforcement 243 or 245 of each delivery blood storing member 203a, 203b be not adhered to each other at all or except at the peripheral end portions thereof. The diaphragm 242 or 244 and the reinforcement 243 or 245 of each delivery blood storing member 203a, 203b may also be adhered to each other at all, if little change of the compliance of the diaphragm adhered to the reinforcement occurs. If the reinforcement between the first diaphragm 242 and the second diaphragm 244 is omitted, it is preferred that the first diaphragm 242 and the second diaphragm 244 be not adhered to each other at all or except at the peripheral end portions thereof. Furthermore, it is preferred that the reinforcement be not in close contact with the diaphragm. The diaphragm and the reinforcement may also be united into a single member.

The delivery blood storing members 203a, 203b are connected in fluid communication to the blood flow passage portions 235a, 235b, respectively, by blood flow openings 231a, 231b which are positioned at lower portions of the delivery blood storing members 203a, 203b (at lower ends thereof) and which are formed at substantially the same height in the vertical direction as a lower end of the blood keeping portion 29 of the blood reservoir tank portion 202. The blood reservoir tank portion 202 includes the blood keeping portion 229 and the blood outlets 226a, 226b formed in lower end of the blood keeping portion 229. The delivery blood storing members 203a, 203b are positioned above the blood outlets 226a, 226b. The delivery blood storing members 203a, 203b extend substantially parallelly to the projected portion 223c of the blood reservoir tank portion 202 and substantially vertically upward. If the blood surface in the blood reservoir tank portion 202 is below the uppermost end of the inner space of each delivery blood storing member 203a, 203b, amounts of blood proportional to the blood surface in the blood reservoir tank portion 202 flow into the delivery blood storing members 203a, 203b. If the blood surface in the blood reservoir tank portion 202 is above the uppermost end of the inner space of each delivery blood storing member 203a, 203b, the maximum amount of blood flows into the delivery blood storing members 203a, 203b since the maximum capacity of the delivery blood storing members 203a, 203b is fixed.

More specifically, the delivery blood storing members 203a, 203b receive pressure proportional to the amount of blood stored in the blood reservoir tank portion 202, thus forming pressure-sensitive containers. If the amount of blood (liquid surface) in the blood reservoir tank portion 202 is equal to or greater than a predetermined amount (in this embodiment, the blood surface in the blood reservoir tank portion 202 is above the uppermost end of the inner space of each delivery blood storing member 203a, 203b), the amount of blood reserved in the delivery blood storing members 203a, 203b is determined by the maximum capacity thereof, not by the pressure corresponding to the amount of blood stored in the blood reservoir tank portion 202. That is, the delivery blood storing members 203a, 203b reserve the maximum amount of blood. If the amount of blood stored in the blood reservoir tank portion 202 is equal to or less than the predetermined amount (in this embodiment, the blood surface in the blood reservoir tank portion 202 is below the uppermost end of the inner space of each delivery blood storing member 203a, 203b), the pressure sensitivity of the delivery blood storing members 203a, 203b becomes effective so that the delivery blood storing members 203a, 203b reserve amounts of blood proportional to the amount of blood stored in the blood reservoir tank portion 202 (that is, the height of the blood surface in the blood reservoir tank portion 202). In short, the delivery blood storing members 203a, 203b function to automatically reserve amounts of blood proportional to the amount of blood stored in the blood reservoir tank portion 202 when the amount of blood in the blood reservoir tank portion 202 is equal to or less than the predetermined value.

The delivery blood storing members 203a, 203b do not spontaneously draw in blood, that is, do not substantially have self-shape-restoring characteristic. If the delivery blood storing members 203a, 203b were formed so that the members have a preset shape and self-shape-restoring characteristic, the delivery blood storing members 203a, 203b would restore their preset shape when the load from the drive members for forcing blood out of the members 203a, 203b is removed after blood is thereby forced out. Then the self-restoring force of the delivery blood storing members 203a, 203b would cause a suction force, whereby blood would be drawn back into the delivery blood storing members 203a, 203b from the side of the blood reservoir tank portion 202. In short, the delivery blood storing members 203a, 203b would retain a certain minimum level of blood, below which the pressure sensitivity could not be effective.

The maximum amount of blood that can be reserved by the delivery blood storing members 203*a*, 203*b* (the maximum amount that can be contained therein, that is, the capacity thereof) varies depending on the capacity of the blood reservoir tank portion 202 used. However, the capacity of the delivery blood storing members 203*a*, 203*b* is preferably about 20–500 mL and, particularly, about 50–500 mL. More preferably, the capacity thereof is about 50–300 mL and, particularly, about 80–300 mL.

The blood reserved in the delivery blood storing members 203*a*, 203*b* is forced out therefrom by the blood delivering drive units described below. The forced-out blood flows into the blood flow passage portions 235*a*, 235*b*, and then flows out through the blood discharge opening 207. Therefore, if the amount of blood stored in the blood reservoir tank portion 202 of the delivery blood storing member-equipped blood reservoir tank 201 decreases below a predetermined value, blood is delivered in amount proportional to the amount of blood remaining in storage. That is, as the amount of blood remaining in storage decreases, the amount of blood delivered automatically decreases. The amount of blood delivered may become very close to zero but never becomes zero. That is, blood delivery is maintained even in very small amounts. Therefore, there is no interruption of blood delivery, so that blood stagnation does not occur in a side of the extracorporeal blood circulation circuit downstream from the delivery blood storing member-equipped blood reservoir tank 201.

The delivery blood storing member body part 241 may be formed from, for example, polycarbonate, acrylic resin, polyethylene terephthalate, polyethylene, polypropylene, polystyrene, polyvinyl chloride, acryl-styrene copolymers, acryl-butadiene-styrene copolymers and the like. Polycarbonate, acrylic resin, polystyrene, and polyvinyl chloride are especially preferred.

The diaphragms 242, 244 may be suitably formed from, for example, polyurethane, silicon-based polymers, polyvinyl chloride, and the like. Particularly preferred materials are polyurethane and silicon-based polymers, which are presently widely used for members that contact blood. The reinforcements 243, 245 may be provided in the form of a woven fabric, a non-woven fabric, a knitted fabric, a sheet material or the like. In view of strength, the form of a woven or knitted fabric is preferred. As for examples of the material of the reinforcements, polyethylene terephthalate, nylon 6, nylon 66, regenerated cellulose, polypropylene, fiber-reinforced plastics (FRP, with aramid fiber or the like), stainless steel, aluminum or the like may be suitably used. Particularly preferred are polyethylene terephthalate, nylon 6, nylon 66, regenerated cellulose and polypropylene.

It is preferred that the diaphragms 242, 244 be sufficiently soft. As an index of softness, compliance may be employed. The diaphragms 242, 244 of the delivery blood storing members 203*a*, 203*b* have a compliance of, preferably, 2 ml/sec·mmHg or higher and, more preferably, within the range of 5–30 ml/sec·mmHg, when the blood surface in the blood keeping portion 229 of the blood reservoir tank portion 202 is lower than the uppermost portion of the inner space of each of the delivery blood storing members 203*a*, 203*b*, that is, when the pressure sensitivity (liquid surface sensitivity) of the delivery blood storing members 203*a*, 203*b* is effective. It is further preferred that the diaphragms of the delivery blood storing members 203*a*, 203*b* have a compliance that is lower than the aforementioned value, when the blood surface in the blood keeping portion of the blood reservoir tank portion 202 is higher than the uppermost portion of the inner space of each of the delivery blood storing members 203*a*, 203*b*. The resistance against blood inflow into the delivery blood storing members 203*a*, 203*b* can be expressed by rate of blood inflow to the delivery blood storing members 203*a*, 203*b*. The rate of blood inflow to the delivery blood storing members 203*a*, 203*b* is preferably 20–600 ml/sec.

It is also preferred that the blood contacting surfaces of the delivery blood storing members 203*a*, 203*b* of the delivery blood storing member-equipped blood reservoir tank 201 and of a blood delivery instrument 280 for an extracorporeal blood circulation circuit (shown in FIG. 41) be non-thrombogenic surfaces, which will be described below.

The blood delivering drive unit 204 is disposed outward of each delivery blood storing member 203*a*, 203*b*, that is, outward of the diaphragm 242 thereof. The blood delivering drive unit 204 has a pressurizing portion 251 capable of pressurizing the diaphragm side so as to forcing the diaphragm to closely contact the delivery blood storing member body part 241. In this embodiment, the pressurizing portion 251 is equipped with a cylinder 252 that is driven by an external drive device. By operation of the blood delivering drive units 204, blood is intermittently discharged out of the delivery blood storing members 203*a*, 203*b*.

The delivery blood storing member-equipped blood reservoir tank 201 of this embodiment is equipped with two sets of the delivery blood storing member 203 and the blood delivering drive unit 204. Accordingly, two separate blood flow passage portions 235 (235*a*, 235*b*) are provided without communication therebetween, as shown in FIG. 37. By providing two or more sets thereof in this manner, the capacity of each delivery blood storing member 203 and each blood delivering drive unit 204 can be reduced, so that the blood inflow and discharge response improves. However, the construction of the invention is not limited by this embodiment. The number of sets of the delivery blood storing member 203 and the blood delivering drive unit 204 may also be one, or three or more.

If two sets of the delivery blood storing member 203 and the blood delivering drive unit 204 are provided as in the delivery blood storing member-equipped blood reservoir tank 201 and, furthermore, the individual blood delivering drive units can be separately controlled by a fluid supply machine for blood delivery, it becomes possible to select the form of blood flow for delivery, more specifically, select a pulse flow or a constant flow, considering the conditions of a patient, the type of the artificial lung used or the like. It becomes also possible to change the form of delivery blood flow while in use. If two sets of the delivery blood storing member and the blood delivering drive unit are provided as in the embodiment, a substantially constant blood flow can be achieved by shifting the phases of the blood flow out of the individual delivery blood storing members by substantially 180° from each other, that is, by shifting the phases of fluid flowing into and out of the blood delivering drive units by substantially 180° from each other and setting the proportion of pulse outflow to at least half the period. A good pulse flow can be achieved by setting the phases of blood flow out of the individual delivery blood storing members to substantially the same phase or within ±30°, that is, by setting the phases of fluid flowing into and out of the blood delivering drive units to substantially the same phase or within ±30°. If three or more sets of the delivery blood storing member and the blood delivering drive unit are provided, the form of blood flow will become a substantially constant flow by shifting the phases of blood flow out of the individual delivery blood storing members by an angle obtained by dividing 360° by the number of the sets provided.

Figure 39:
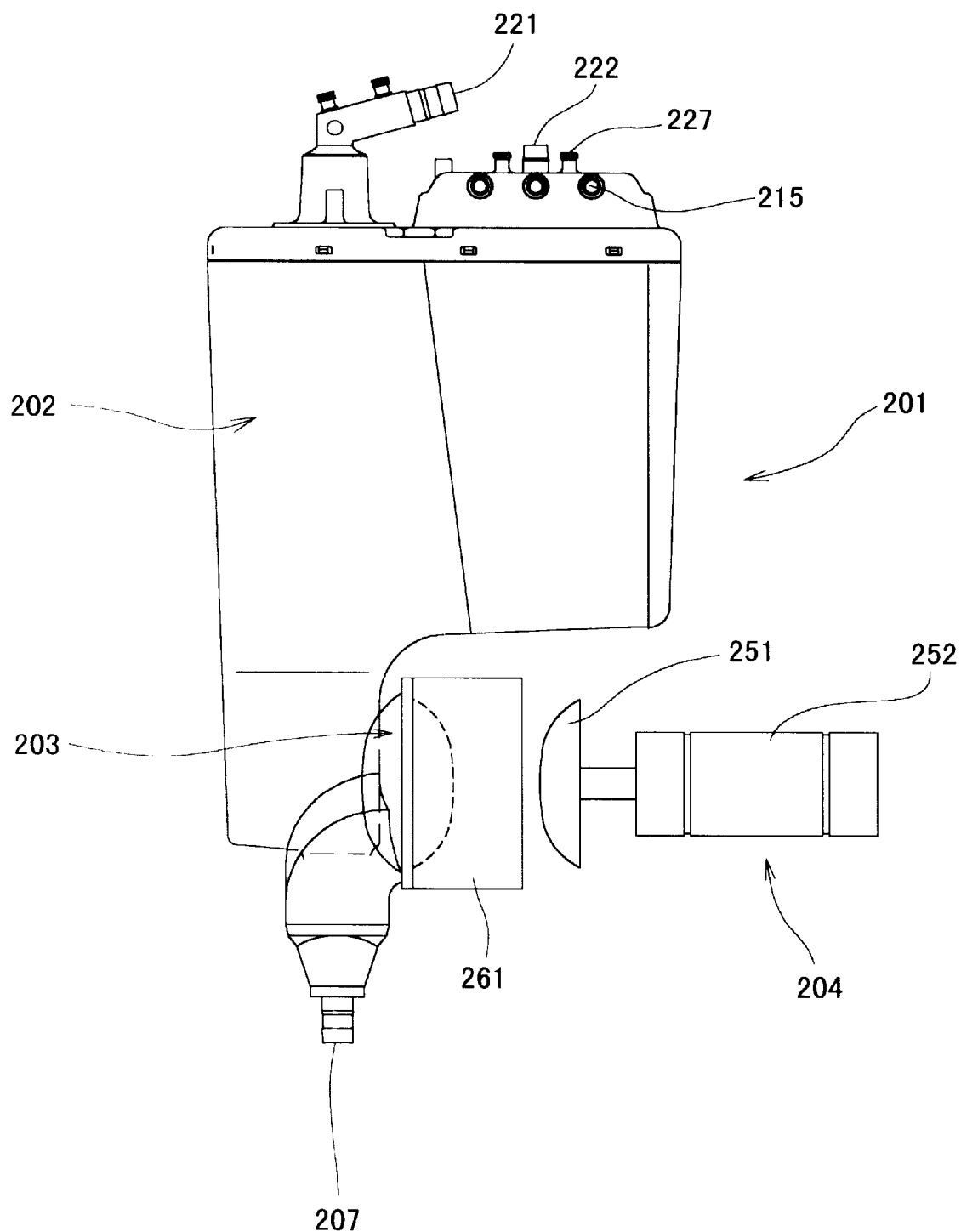
FIG. 39 is a side view of a delivery blood storing member-equipped blood reservoir tank and a blood delivering drive unit according another embodiment of the present invention.

Optionally, a tubular protective cover 261 may be provided, as shown in FIG. 39, for protecting at least the diaphragm 242 of the delivery blood storing member 203. The protective cover 261 has an opening through which the pressurizing portion 251 of the blood delivering drive unit 204 can penetrate. By providing such a cover, the incidence of damages or breakage of the diaphragm or the like due to external factors can be reduced. The protective cover is a hard cover, and may be suitably formed from any of the materials indicated above as a material of the blood reservoir tank portion housing. The protective cover may cover the entire delivery blood storing member, instead of covering only the diagram 242.

Figure 40:
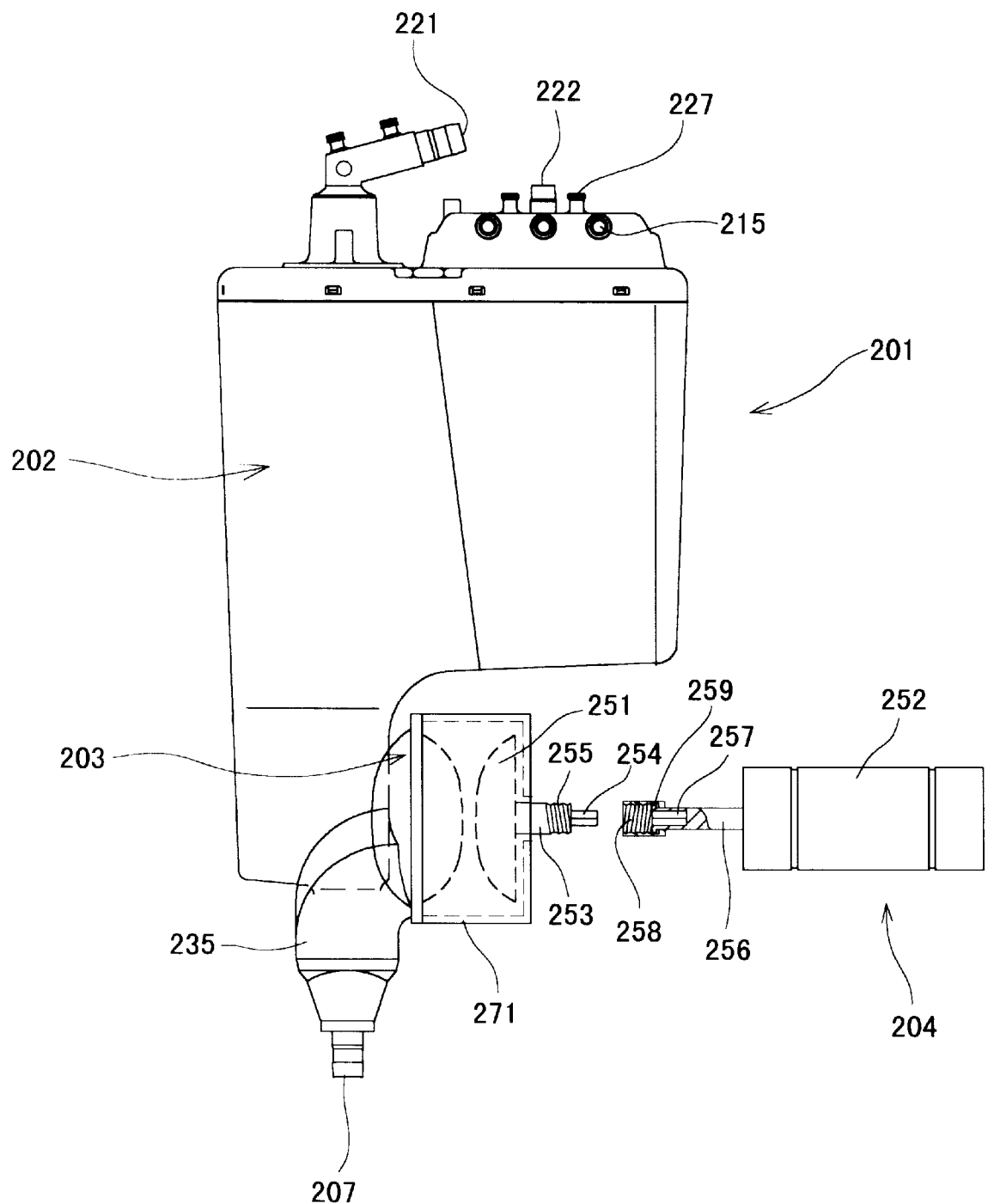
FIG. 40 is a side view of a delivery blood storing member-equipped blood reservoir tank according to still another embodiment of the present invention.

Such a protective cover may also be provided as a protective cover 271, as shown in FIG. 40, for protecting at least the diaphragm 242 and for housing a diaphragm pressurizing member 251 in such a manner that the diaphragm pressurizing member 251 can be moved but cannot be detached. With this construction, the diaphragm pressurizing member 251 is detachably connectable to a pressurizing portion drive device 252. This construction prevents entrance of foreign matter into a space between the diaphragm 242 and the diaphragm pressurizing member 251 during operation and, therefore, more reliably prevents damages to the diaphragm. The diaphragm pressurizing member 251 is provided with a shaft 253 extending outward from a rear end surface the diaphragm pressurizing member 251. The shaft 253 has a protrusion 254 for connecting to a further outward extending rod 256 of the pressurizing portion drive device (cylinder) 252. The protrusion 254 has a sectional shape of a polygon or the like such that the protrusion 254 restricts rotation relative to the cylinder rod 256 when connected to the cylinder rod 256. A rearward end portion of the shaft 253 of the diaphragm pressurizing member 251 has a screw portion (male thread) 255. Formed in a distal end portion of the rod 256 of the pressurizing portion drive device (cylinder) 252 is a recess 257 extending in the direction of the axis of the rod 256 and having such a shape as to receive the protrusion 254 of the shaft 253 of the diaphragm pressurizing member 251. A fitting member is rotatably attached to the distal end of the rod 256 of the pressurizing portion drive device 252. The fitting member has an inner screw portion (female thread) 258 that can be screwed to the screw portion 255 formed on the shaft 253 of the diaphragm pressurizing member 251. The diaphragm pressurizing member 251 is thereby detachably connectable to the rod 256 of the pressurizing portion drive device (cylinder) 252.

Next described will be blood delivery instrument for an extracorporeal blood circulation circuit according to the invention.

Figure 41:
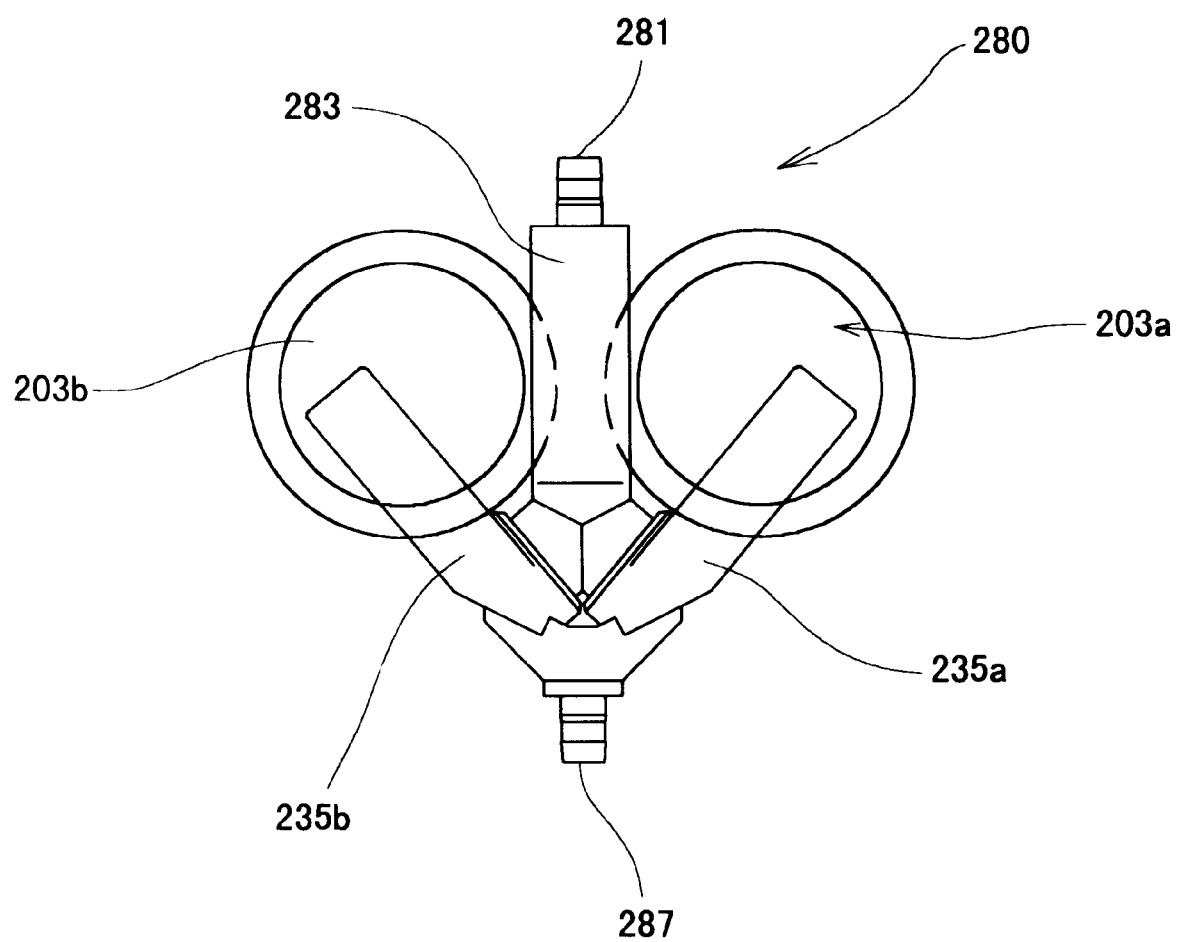
FIG. 41 is a front elevation of a blood delivery instrument for an extracorporeal blood circulation circuit according to yet another embodiment of the present invention.
Figure 42:
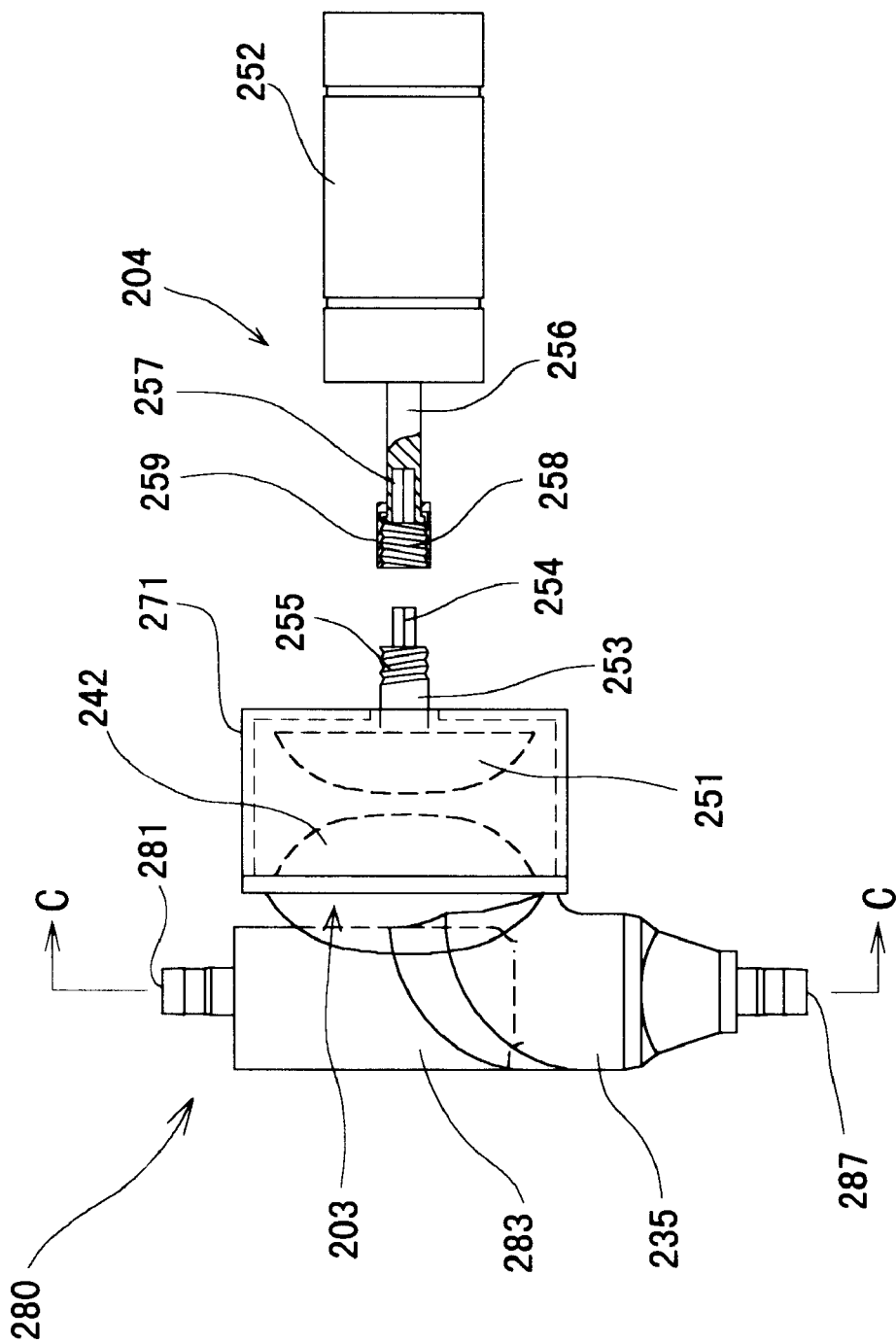
FIG. 42 is a side view of the blood delivery instrument for an extracorporeal blood circulation circuit.
Figure 43:
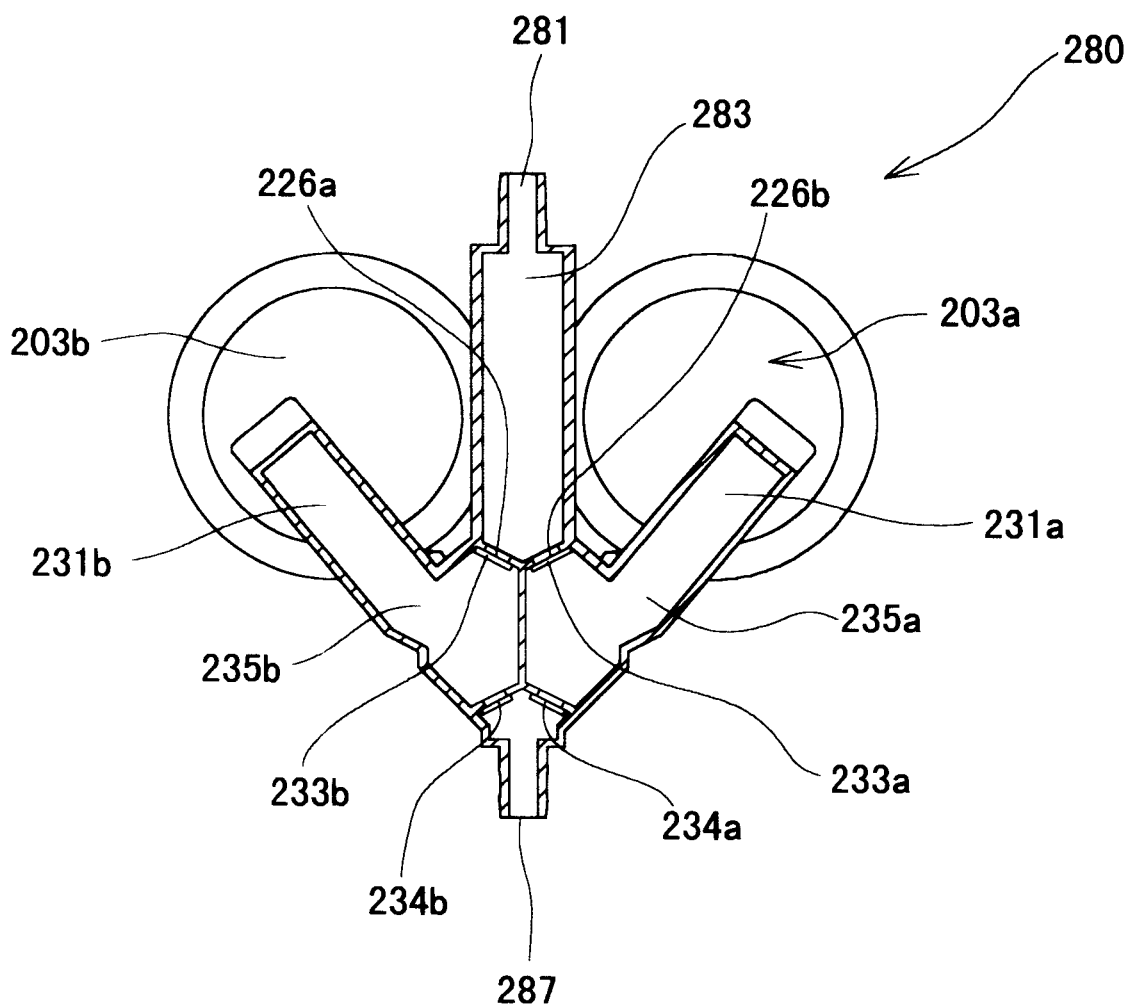
FIG. 43 is a sectional view taken on line C—C of FIG. 42.

FIG. 41 is a front elevation of a blood delivery instrument for an extracorporeal blood circulation circuit according to an embodiment of the invention. FIG. 42 is a side view of the blood delivery instrument for an extracorporeal blood circulation circuit. FIG. 43 is a sectional view taken on line C—C of FIG. 42.

A blood delivery instrument 280 according to an embodiment of the invention is for use in an extracorporeal blood circulation circuit. The blood delivery instrument 280 includes a connecting portion 281 to the extracorporeal blood circulation circuit, and delivery blood storing members 203a, 203b that allow blood to flow from inside thereof when pressed from outside. The delivery blood storing members 203a, 203b reserve amounts of blood in accordance with the height of liquid surface in a blood reservoir tank provided in the extracorporeal blood circulation circuit or the height of liquid surface in an upstream portion of the blood delivery instrument upstream from the delivery blood storing members, if the amount of blood present in the blood reservoir tank or the amount of blood present in the upstream portion of the blood delivery instrument becomes equal to or less than a predetermined value. Each of the delivery blood storing members 203a, 203b includes a delivery blood storing member body part 241 formed from a hard material, and a flexible diaphragm 242 whose peripheral end is fixed to the delivery blood storing member body part 241. The diaphragm 242 produces substantially no self-restoring force against deformation.

A blood delivery instrument 280 for use in an extracorporeal blood circulation circuit according to another embodiment of the invention includes a connecting portion 281 to the extracorporeal blood circulation circuit, and delivery blood storing members 203a, 203b that allow blood to flow from inside thereof when pressed from outside. The delivery blood storing members 203a, 203b reserve amounts of blood in accordance with the height of liquid surface in a blood reservoir tank provided in the extracorporeal blood circulation circuit or the height of liquid surface in an upstream portion of the blood delivery instrument upstream from the delivery blood storing members, if the amount of blood present in the blood reservoir tank or the amount of blood present in the upstream portion of the blood delivery instrument becomes equal to or less than a predetermined value. Each of the delivery blood storing members 203a, 203b includes a delivery blood storing member body part 241 formed from a hard material, a flexible diaphragm 242 whose peripheral end is fixed to the delivery blood storing member body part 241, and a reinforcement which covers the diaphragm 242 and whose peripheral end is fixed to the delivery blood storing member body part 241.

With this construction, the blood delivery instrument 280 achieves substantially the same advantages as achieved by the delivery blood storing member-equipped blood reservoir tank 201 described above.

The connecting portion 281 to a blood reservoir tank is provided for connection to a blood outlet port of the blood reservoir tank, for example, using a short tube. The construction of the delivery blood storing members 203a, 203b is substantially the same as the that of the delivery blood storing members 203a, 203b of the delivery blood storing member-equipped blood reservoir tank 201 described above. A difference therebetween is that the delivery blood storing members 203a, 203b of the blood delivery instrument 280 are not provided integrally with the blood reservoir tank portion 202, but provided with the connecting portion 281 to the blood reservoir tank.

In addition to the connecting portion 281 to a blood reservoir tank and the two delivery blood storing members 203a, 203b, the blood delivery instrument 280 has blood flow passage portions 235a, 235b that connect in fluid communication between the connecting portion 281 and the delivery blood storing members 203a, 203b, respectively. Provided outside each delivery blood storing member 203a, 203b is a drive member for directly or indirectly pressing the diaphragm 242 of the delivery blood storing member when necessary.

The connecting portion 281 to a blood reservoir tank has a downward extending blood reserving portion 283 for reserving a predetermined amount (for example, 5–100 ml) of blood, and two blood outlets 226a, 226b formed in a lower portion (lower end) of the blood reserving portion 283, in addition to the aforementioned blood inlet port formed in an upper end thereof.

The blood flow passage portions 235a, 235b connecting between the blood reserving portion 283 and the two delivery blood storing members 203a, 203b are formed below the blood reserving portion 283 as shown in FIG. 41. A blood flow passage portion 235a of the two separate blood flow passage portions 235a, 235b communicates only with a first delivery blood storing member 203a, and the other blood flow passage portion 235b communicates only with the other delivery blood storing member 203b. Disposed near the blood outlets 226a, 226b of the blood reserving portion 283, that is, at boundary sites between the blood reserving portion 283 and the blood flow passage portions 235a, 235b, are first check valves 233a, 233b that allow flow of blood from the blood reserving portion 283 toward the blood flow passage portions 235a, 235b (that is, toward the delivery blood storing members 203a, 203b) and restricts (prevents) the reverse flow of blood. The first check valves 233a, 233b function as passage control members for blocking the communication between the blood reserving portion 283 and the delivery blood storing members 203a, 203b during the operation of the blood delivering drive unit 204 as described below. The blood delivery instrument 280 has a blood discharge opening 287 that communicates with the blood flow passage portions 235a, 235b. Provided near the blood discharge opening 287 are second check valves 234a, 234b that allow blood flow toward a side downstream from the blood flow passage portions 235a, 235b (that is, downstream from the delivery blood storing members 203a, 203b) and restricts the reverse flow of blood. The second check valves 234a, 234b function as passage control members for blocking reverse blood flow from the downstream side toward the delivery blood storing members 203a, 203b (that is, into the blood flow passage portions 235a, 235b) when the blood delivering drive unit 204 is not operated.

Each check valve 233, 234 has a disc-shaped movable valve body a portion of which is secured to the housing of the blood delivery instrument 280. Preferably, the movable valve body of each check valve has a slightly less specific gravity than blood, and a hardness of about 3 to 7 on Shore A scale. The valve bodies are preferably formed from, for example, styrene-based elastomer oil gel, silicone gel or the like, to a thickness of about 0.5 to 5 mm.

Each of the delivery blood storing members 203a, 203b, as in those shown in FIG. 38, includes the delivery blood storing member body part 241 formed from a hard material and the diaphragm 242 fixed at its peripheral end to the delivery blood storing member body part 241. The delivery blood storing member body part 241 has a curved inner surface, more specifically, a generally semi-spherical inner surface. The diaphragm 242 has a shape corresponding to the shape of the inner surface of the delivery blood storing member body part 241.

Each diaphragm 242 produces substantially no self-restoring force against deformation. Each of the delivery blood storing members 203a, 203b in this embodiment further includes the reinforcement covering the diaphragm and fixed at its peripheral end to the delivery blood storing member body part 241. Preferably, the diaphragm 242 and the reinforcement 243 combined have the following properties: the pressure needed to deform the diaphragm 242 is equal to or less than 100 mmH$_2$O; the rupture strength is equal to or greater than 5 kg/cm$^2$; and the diaphragm 242 itself produces substantially no self-restoring force against deformation. Each of the delivery blood storing members 203a, 203b in this embodiment is provided with the reinforcement 243 (first reinforcement), as shown in FIG. 38, for reliably preventing damages to the diaphragm 242 (first diaphragm) and ensuring blood delivery even if the diaphragm 242 should be damaged. The reinforcement 243 covers the diaphragm 242 and is fixed at its peripheral end to the delivery blood storing member body part 241. Furthermore, each delivery blood storing member 203a, 203b has a second diaphragm 244 which covers the reinforcement 243 (first reinforcement) and whose peripheral end is fixed to the delivery blood storing member body part 241, and a second reinforcement 245 that covers the second diaphragm 244 and whose peripheral end is fixed to the delivery blood storing member body part 241. The reinforcement disposed between the first diaphragm 242 and the second diaphragm 244 may be omitted.

It is preferred that the diaphragm 242 or 244 and the reinforcement 243 or 245 of each delivery blood storing member 203a, 203b be not adhered to each other at all or except at the peripheral end portions thereof. If the reinforcement between the first diaphragm 242 and the second diaphragm 244 is omitted, it is preferred that the first diaphragm 242 and the second diaphragm 244 be not adhered to each other at all or except at the peripheral end portions thereof. Furthermore, it is preferred that the reinforcement be not in close contact with the diaphragm. The diaphragm and the reinforcement may also be united into a single member.

The delivery blood storing members 203a, 203b are connected in fluid communication to the blood flow passage portions 235a, 235b, respectively, by blood flow openings 231a, 231b which are positioned at lower portions of the delivery blood storing members 203a, 203b (at lower ends thereof) and which are formed at substantially the same height in the vertical direction as a lower end of a blood keeping portion 229 of the blood reserving portion 283. The blood reserving portion 283 includes the blood keeping portion 229 and the blood outlets 226a, 226b formed in lower end of the blood keeping portion 229. The delivery blood storing members 203a, 203b are positioned above the blood outlets 226a, 226b. The delivery blood storing members 203a, 203b extend substantially parallelly to a projected portion 223c of the blood reserving portion 283 and substantially vertically upward. If the blood surface in the blood reserving portion 283 is below the uppermost end of the inner space of each delivery blood storing member 203a, 203b, amounts of blood proportional to the blood surface in the blood reserving portion 283 flow into the delivery blood storing members 203a, 203b. If the blood surface in the blood reserving portion 283 is above the uppermost end of the inner space of each delivery blood storing member 203a, 203b, the maximum amount of blood flows into the delivery blood storing members 203a, 203b since the maximum capacity of the delivery blood storing members 203a, 203b is fixed.

More specifically, the delivery blood storing members 203a, 203b receive pressure proportional to the amount of blood stored in the blood reserving portion 283, thus forming pressure-sensitive containers. If the amount of blood in the blood reserving portion 283 is equal to or greater than a predetermined amount (in this embodiment, the blood surface in the blood reserving portion 283 is above the uppermost end of the inner space of each delivery blood storing member 203a, 203b), the amount of blood reserved in the delivery blood storing members 203a, 203b is determined by the maximum capacity thereof, not by the pressure corresponding to the amount of blood stored in the blood reserving portion 283. That is, the delivery blood storing members 203a, 203b reserve the maximum amount of blood. If the amount of blood stored in the blood reserving portion 283 is equal to or less than the predetermined amount (in this embodiment, the blood surface in the blood reserving portion 283 is below the uppermost end of the inner space of each delivery blood storing member 203a, 203b), the pressure sensitivity of the delivery blood storing members 203a, 203b becomes effective so that the delivery blood storing members 203a, 203b reserve amounts of blood proportional to the amount of blood stored in the blood reserving portion 283 (that is, proportional to the height of the blood surface in the blood reserving portion 283). In short, the delivery blood storing members 203a, 203b function to automatically reserve amounts of blood proportional to the amount of blood stored in the blood reserving portion 283 when the amount of blood in the blood reserving portion 283 is equal to or less than the predetermined value.

The delivery blood storing members 203a, 203b do not spontaneously draw in blood, that is, do not substantially have self-shape-restoring characteristic. If the delivery blood storing members 203a, 203b were formed so that the members have a preset shape and self-shape-restoring characteristic, the delivery blood storing members 203a, 203b would restore their preset shape when the load from the drive members for forcing blood out of the members 203a, 203b is removed after blood is thereby forced out. Then the self-restoring force of the delivery blood storing members 203a, 203b would cause a suction force, whereby blood would be drawn back into the delivery blood storing members 203a, 203b from the side of the blood reserving portion 283. In short, the delivery blood storing members 203a, 203b would retain a certain minimum level of blood, below which the pressure sensitivity could not be effective.

The maximum amount of blood that can be reserved by the delivery blood storing members 203a, 203b (the maximum amount that can be contained therein, that is, the capacity thereof) varies depending on the capacity of the blood reserving portion 283 used. However, the capacity of the delivery blood storing members 203a, 203b is preferably about 20–500 mL and, particularly, about 50–500 mL. More preferably, the capacity thereof is about 50–300 mL and, particularly, about 80–300 mL.

The blood reserved in the delivery blood storing members 203a, 203b is forced out therefrom by the blood delivering drive units described below. The forced-out blood flows into the blood flow passage portions 235a, 235b, and then flows out through the blood discharge opening 287. Therefore, if the amount of blood stored in the blood reserving portion 283 of the blood delivery instrument 280 for an extracorporeal blood circulation circuit decreases below a predetermined value, blood is delivered in amount proportional to the amount of blood remaining in storage. That is, as the amount of blood remaining in storage decreases, the amount of blood delivered automatically decreases. The amount of blood delivered may become very close to zero but never becomes zero. That is, blood delivery is maintained even in very small amounts. Therefore, there is no interruption of blood delivery, so that blood stagnation does not occur in a side of the extracorporeal blood circulation circuit downstream from the blood delivery instrument 280.

The delivery blood storing member body part 241, the diaphragms 242, 244 and the reinforcements 243, 245 may suitably be formed from any of the materials indicated above.

It is preferred that the diaphragms 242, 244 be sufficiently soft. As an index of softness, compliance may be employed. The diaphragms 242, 244 of the delivery blood storing members 203a, 203b have a compliance of, preferably, 2 ml/sec.mmHg or higher and, more preferably, within the range of 5–30 ml/sec.mmHg, when the blood surface in the blood keeping portion 229 of the blood reserving portion 283 is lower than the uppermost portion of the inner space of each of the delivery blood storing members 203a, 203bthat is, when the pressure sensitivity (liquid surface sensitivity) of the delivery blood storing members 203a, 203b is effective. It is further preferred that the diaphragms of the delivery blood storing members 203a, 203b have a compliance that is lower than the aforementioned value, when the blood surface in the blood keeping portion 229 of the blood reserving portion 283 is higher than the uppermost portion of the inner space of each of the delivery blood storing members 203a, 203b. The resistance against blood inflow into the delivery blood storing members 203a, 203b can be expressed by rate of blood inflow to the delivery blood storing members 203a, 203b. The rate of blood inflow to the delivery blood storing members 203a, 203b is preferably 20–600 ml/sec.

It is also preferred that the blood contacting surfaces of the delivery blood storing members 203a, 203b be non-thrombogenic surfaces. The non-thrombogenic surfaces can be suitably formed by a method described above.

The blood delivering drive unit 204 is disposed outward of each delivery blood storing member 203a, 203b that is, outward of the diaphragm 242 thereof. The blood delivering drive unit 204 has a pressurizing portion capable of pressurizing the diaphragm side so as to forcing the diaphragm to closely contact the delivery blood storing member body part 241. In this embodiment, the pressurizing portion is equipped with a cylinder that is driven by an external drive device. By operation of the blood delivering drive units 204, blood is intermittently discharged out of the delivery blood storing members 203a, 203b.

The blood delivery instrument 280 for an extracorporeal blood circulation circuit of this embodiment is equipped with two sets of the delivery blood storing member 203 and the blood delivering drive unit 204. Accordingly, two separate blood flow passage portions 235 (235a, 235b) are provided without communication therebetween, as shown in FIG. 43. By providing two or more sets thereof in this manner, the capacity of each delivery blood storing member 203 and each blood delivering drive unit 204 can be reduced, so that the blood inflow and discharge response improves. However, the construction of the invention is not limited by this embodiment. The number of sets of the delivery blood storing member 203 and the blood delivering drive unit 204 may also be one, or three or more.

If two sets of the delivery blood storing member 203 and the blood delivering drive unit 204 are provided as in the blood delivery instrument 280 for an extracorporeal blood circulation circuit and, furthermore, the individual blood delivering drive units can be separately controlled by a fluid supply machine for blood delivery, it becomes possible to select the form of blood flow for delivery, more specifically, select a pulse flow or a constant flow, considering the conditions of a patient, the type of the artificial lung used or the like. It becomes also possible to change the form of delivery blood flow while in use.

The blood delivery instrument 280 for an extracorporeal blood circulation circuit has a protective cover 271, as shown in FIG. 42, for protecting at least the diaphragm 242 and for housing a diaphragm pressurizing member 251 in such a manner that the diaphragm pressurizing member 251 can be moved but cannot be detached. With this construction, the diaphragm pressurizing member 251 is detachably connectable to a pressurizing portion drive device 252. This construction prevents entrance of foreign matter into a space between the diaphragm 242 and the diaphragm pressurizing member 251 during operation and, therefore, more reliably prevents damages to the diaphragm. The diaphragm pressurizing member 251 is provided with a shaft 253 extending outward from a rear end surface the diaphragm pressurizing member 251. The shaft 253 has a protrusion 254 for connecting to a further outward extending rod 256 of the pressurizing portion drive device (cylinder) 252. The protrusion 254 has a sectional shape of a polygon or the like such that the protrusion 254 restricts rotation relative to the cylinder rod 256 when connected to the cylinder rod 256. A rearward end portion of the shaft 253 of the diaphragm pressurizing member 251 has a screw portion (male thread) 255. Formed in a distal end portion of the rod 256 of the pressurizing portion drive device (cylinder) 252 is a recess 257 extending in the direction of the axis of the rod 256 and having such a shape as to receive the protrusion 254 of the shaft 253 of the diaphragm pressurizing member 251. A fitting member is rotatably attached to the distal end of the rod 256 of the pressurizing portion drive device 252. The fitting member has an inner screw portion (female thread) 258 that can be screwed to the screw portion 255 formed on the shaft 253 of the diaphragm pressurizing member 251. The diaphragm pressurizing member 251 is thereby detachably connectable to the rod 256 of the pressurizing portion drive device (cylinder) 252.

The protective cover may also be provided in the form of the protective cover 261 shown in FIG. 39.

Next described will be specific examples of the delivery blood storing member of the delivery blood storing member-equipped blood reservoir tank and the blood delivery instrument for an extracorporeal blood circulation circuit according to the invention.

A polyurethane sheet having a thickness of 0.2 mm was mounted, as a diaphragm, on a delivery blood storing member body part having a shape as shown in FIG. 38. The delivery blood storing member body part and the diaphragm were adhered to each other only at an outer peripheral flange portion of the delivery blood storing member body part. The pressure needed to deform the diaphragm was 10 mmH$_2$O. The diaphragm elastically deformed when loaded with a pressure of 0.65 kg/cm$^2$ or higher. The diaphragm ruptured at 2 kg/cm$^2$.

A polyurethane sheet having a thickness of 0.7 mm was mounted, as a diaphragm, on a delivery blood storing member body part having a shape as shown in FIG. 38. A PET woven fabric was mounted, as a reinforcement, outside the diaphragm. The delivery blood storing member body part, the diaphragm and the reinforcement were adhered to one another only at an outer peripheral flange portion of the delivery blood storing member body part. The diaphragm and the reinforcement were not in close contact. The pressure needed to deform the diaphragm was 100 mmH$_2$O. The diaphragm underwent substantially no elastic deformation by pressurization, and ruptured at 5.3 kg/cm$^2$.

A polyurethane sheet having a thickness of 0.2 mm was mounted, as a diaphragm, on a delivery blood storing member body part having a shape as shown in FIG. 38. A PET woven fabric was mounted, as a reinforcement, outside the diaphragm. The delivery blood storing member body part, the diaphragm and the reinforcement were adhered to one another only at an outer peripheral flange portion of the delivery blood storing member body part. The diaphragm and the reinforcement were not in close contact. The pressure needed to deform the diaphragm was 20 mmH$_2$O. The diaphragm underwent substantially no elastic deformation by pressurization, and ruptured at 5.1 kg/cm$^2$.

A polyurethane sheet having a thickness of 0.2 mm was mounted, as a diaphragm, on a delivery blood storing member body part having a shape as shown in FIG. 38. A second diaphragm formed of the same material as the first diaphragm was mounted outside the first diaphragm. The delivery blood storing member body part and the first and second diaphragms were adhered to one another only at an outer peripheral flange portion of the delivery blood storing member body part. The first and second diaphragms were not in close contact with each other. The pressure needed to deform the diaphragms was 20 mmH$_2$O. The diaphragms elastically deformed when loaded with a pressure of 0.65 kg/cm$^2$ or higher, and ruptured at 2.1 kg/cm$^2$.

A polyurethane sheet having a thickness of 0.2 mm was mounted, as a diaphragm, on a delivery blood storing member body part having a shape as shown in FIG. 38. A PET woven fabric was mounted, as a reinforcement, outside the diaphragm. A second diaphragm and a second reinforcement formed of the same materials as the first diaphragm and the first reinforcement, respectively, were mounted outside. The delivery blood storing member body part, the first and second diaphragms and the first and second reinforcements were adhered only at an outer peripheral flange portion of the delivery blood storing member body part. The diaphragms and the reinforcements were not in close contact with each other. The pressure needed to deform the diaphragms was 40 mmH$_2$O. The diaphragms underwent substantially no elastic deformation by pressurization, and ruptured at 5.3 kg/cm$^2$.

A polyurethane sheet having a thickness of 0.2 mm was mounted, as a diaphragm, on a delivery blood storing member body part having a shape as shown in FIG. 38. A PET woven fabric was mounted, as a reinforcement, outside the diaphragm. A second diaphragm formed of a 0.3 mm-thick polyurethane sheet and a second reinforcement formed of the same material as the first reinforcement were mounted outside. The delivery blood storing member body part, the first and second diaphragms and the first and second reinforcements were adhered only at outer peripheral flange portions. The diaphragms and the reinforcements were not in close contact with each other. The pressure needed to deform the diaphragms was 50 mmH$_2$O. The diaphragms underwent substantially no elastic deformation by pressurization, and ruptured at 5.3 kg/cm$^2$.

In a delivery blood storing member-equipped blood reservoir tank according to the invention, the diagram produces substantially no self-restoring force against deformation.

Therefore, the delivery blood storing member reserves amounts of blood proportional to the amount of blood stored in the blood reservoir tank portion when the amount of blood in the blood reservoir tank portion becomes equal to or less than a predetermined value. By pressing the diaphragm side of the delivery blood storing member from outside, blood can be intermittently forced out of the interior of the delivery blood storing member. That is, when the amount of blood in the blood reservoir tank portion becomes equal to or less than the predetermined value, the delivery blood storing member reserves amounts of blood proportional to the amount of blood stored in the blood reservoir tank portion, and blood is intermittently forced out of the delivery blood storing member by pressing the diaphragm side thereof from outside. Therefore, if the amount of blood in the blood reservoir tank portion becomes small, blood is delivered in proportionally small amounts. Thus, even if the amount of blood remaining in the blood reservoir tank portion becomes small, blood delivery is maintained in small amounts. Consequently, the need to interrupt blood delivery due to a reduction in the amount of blood remaining is eliminated, so that stagnation of blood in the extracorporeal blood circulation circuit can be avoided. Furthermore, since the diaphragm produces substantially no self-restoring force against deformation, the diaphragm sensitively responds to changes in the amount of blood in the blood reservoir tank portion, thereby further ensuring reservation of amounts of blood proportional to the amount of blood remaining in the blood reservoir tank portion.

A delivery blood storing member-equipped blood reservoir tank according to the invention includes a reinforcement covering the diaphragm and fixed at its peripheral end to the delivery blood storing member body part.

Therefore, when the amount of blood in the blood reservoir tank portion becomes equal to or less than a predetermined value, the delivery blood storing member reserves amounts of blood proportional to the amount of blood stored in the blood reservoir tank portion, and blood is intermittently forced out of the delivery blood storing member by pressing the diaphragm side thereof from outside. Therefore, if the amount of blood in the blood reservoir tank portion becomes small, blood is delivered in proportionally small amounts. Thus, even if the amount of blood remaining in the blood reservoir tank portion becomes small, blood delivery is maintained in small amounts. Consequently, the need to interrupt blood delivery due to a reduction in the amount of blood remaining is eliminated, so that stagnation of blood in the extracorporeal blood circulation circuit can be avoided. Furthermore, provision of the reinforcement prevents the diaphragm from being damaged during operation.

In a blood delivery instrument for an extracorporeal blood circulation circuit according to the invention, the diagram produces substantially no self-restoring force against deformation.

Therefore, the delivery blood storing member reserves amounts of blood proportional to the amount of blood stored in the blood reservoir tank portion when the amount of blood in the blood reservoir tank connecting to the delivery blood storing member becomes equal to or less than a predetermined value. By pressing the diaphragm side of the delivery blood storing member from outside, blood can be intermittently forced out of the interior of the delivery blood storing member. That is, when the amount of blood in the blood reservoir tank portion becomes equal to or less than the predetermined value, the delivery blood storing member reserves amounts of blood proportional to the amount of blood stored in the blood reservoir tank portion, and blood is intermittently forced out of the delivery blood storing member by pressing the diaphragm side thereof from outside. Therefore, if the amount of blood in the blood reservoir tank portion becomes small, blood is delivered in proportionally small amounts. Thus, even if the amount of blood remaining in the blood reservoir tank portion becomes small, blood delivery is maintained in small amounts. Consequently, the need to interrupt blood delivery due to a reduction in the amount of blood remaining is eliminated, so that stagnation of blood in the extracorporeal blood circulation circuit can be avoided. Furthermore, since the diaphragm produces substantially no self-restoring force against deformation, the diaphragm sensitively responds to changes in the amount of blood in the blood reservoir tank portion, thereby further ensuring reservation of amounts of blood proportional to the amount of blood remaining in the blood reservoir tank portion.

A blood delivery instrument for an extracorporeal blood circulation circuit according to the invention includes a reinforcement covering the diaphragm and fixed at its peripheral end to the delivery blood storing member body part.

Therefore, when the amount of blood in the blood reservoir tank portion becomes equal to or less than a predetermined value, the delivery blood storing member reserves amounts of blood proportional to the amount of blood stored in the blood reservoir tank portion, and blood is intermittently forced out of the delivery blood storing member by pressing the diaphragm side thereof from outside. Therefore, if the amount of blood in the blood reservoir tank portion becomes small, blood is delivered in proportionally small amounts. Thus, even if the amount of blood remaining in the blood reservoir tank portion becomes small, blood delivery is maintained in small amounts. Consequently, the need to interrupt blood delivery due to a reduction in the amount of blood remaining is eliminated, so that stagnation of blood in the extracorporeal blood circulation circuit can be avoided. Furthermore, provision of the reinforcement prevents the diaphragm from being damaged during operation.

Further embodiments of the blood delivery mechanism member-equipped blood reservoir tank of the invention will be described in detail with reference to the drawings.

Figure 45:
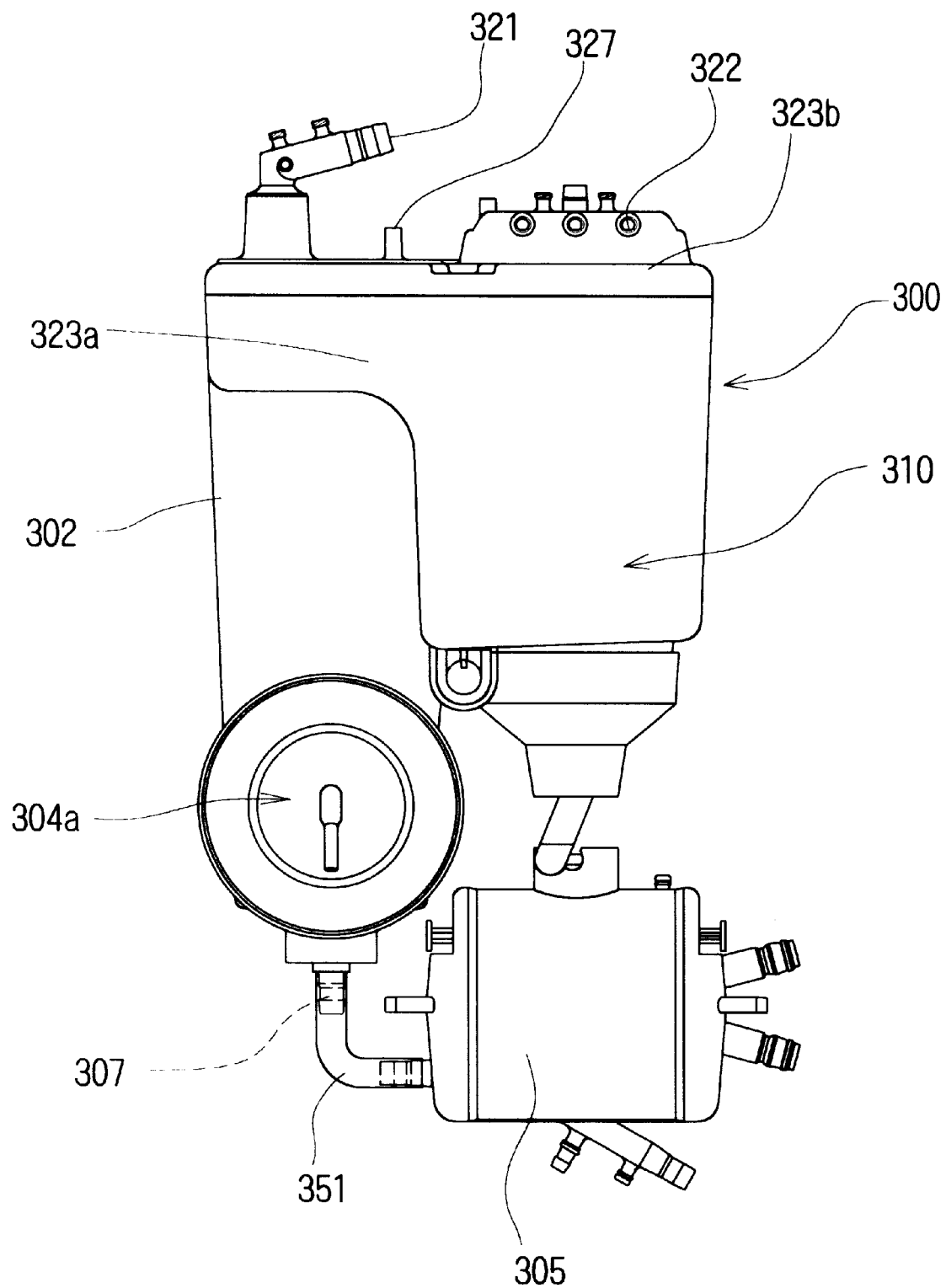
FIG. 45 is a side view of the blood delivery mechanism-equipped blood reservoir tank, with an artificial lung connected.
Figure 46:
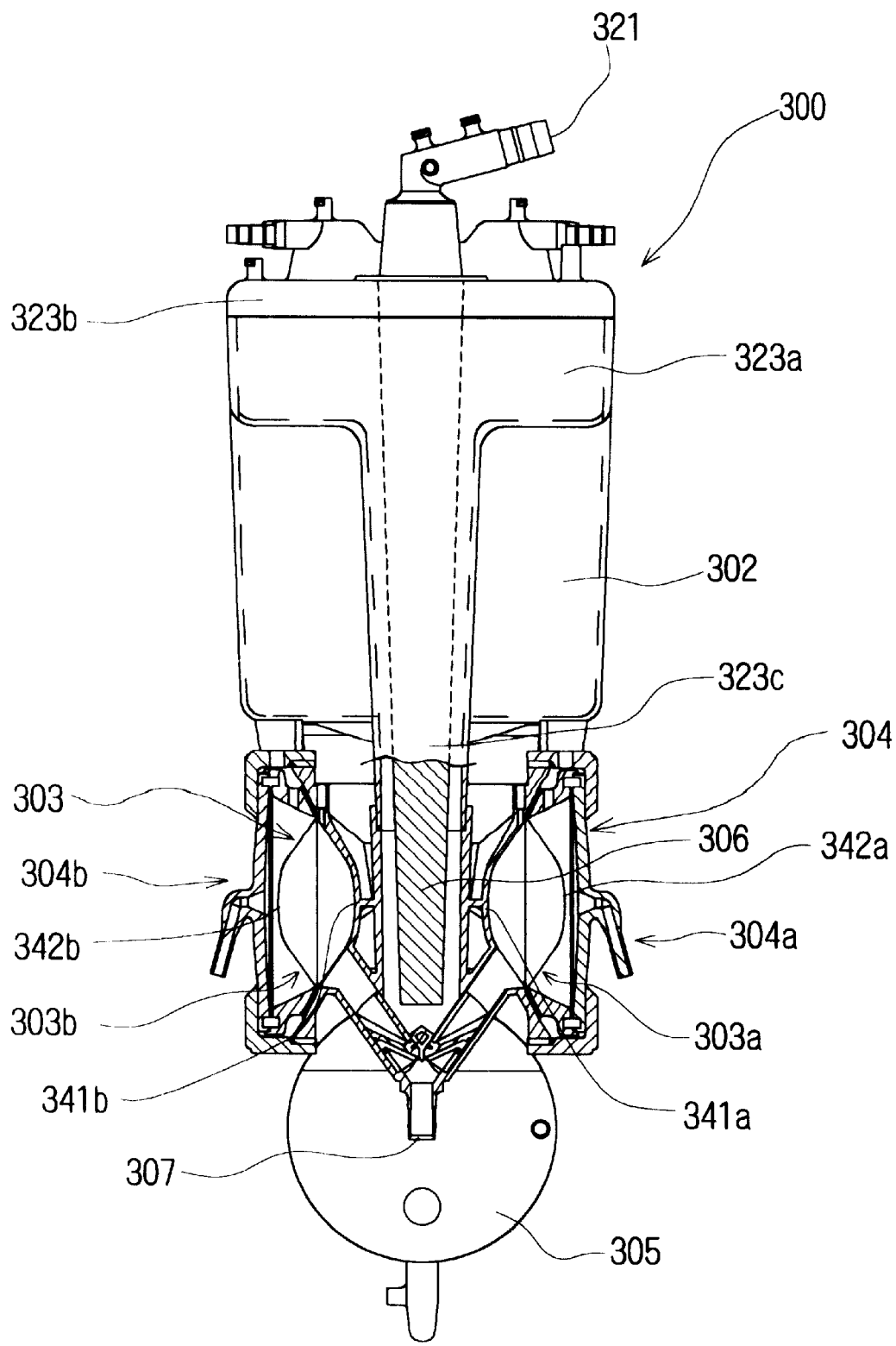
FIG. 46 is a front elevation of the blood delivery mechanism-equipped blood reservoir tank shown in FIG. 44, with a fragmentary sectional view of a blood delivery mechanism and a lower portion of a blood storing portion and their surroundings.
Figure 47:
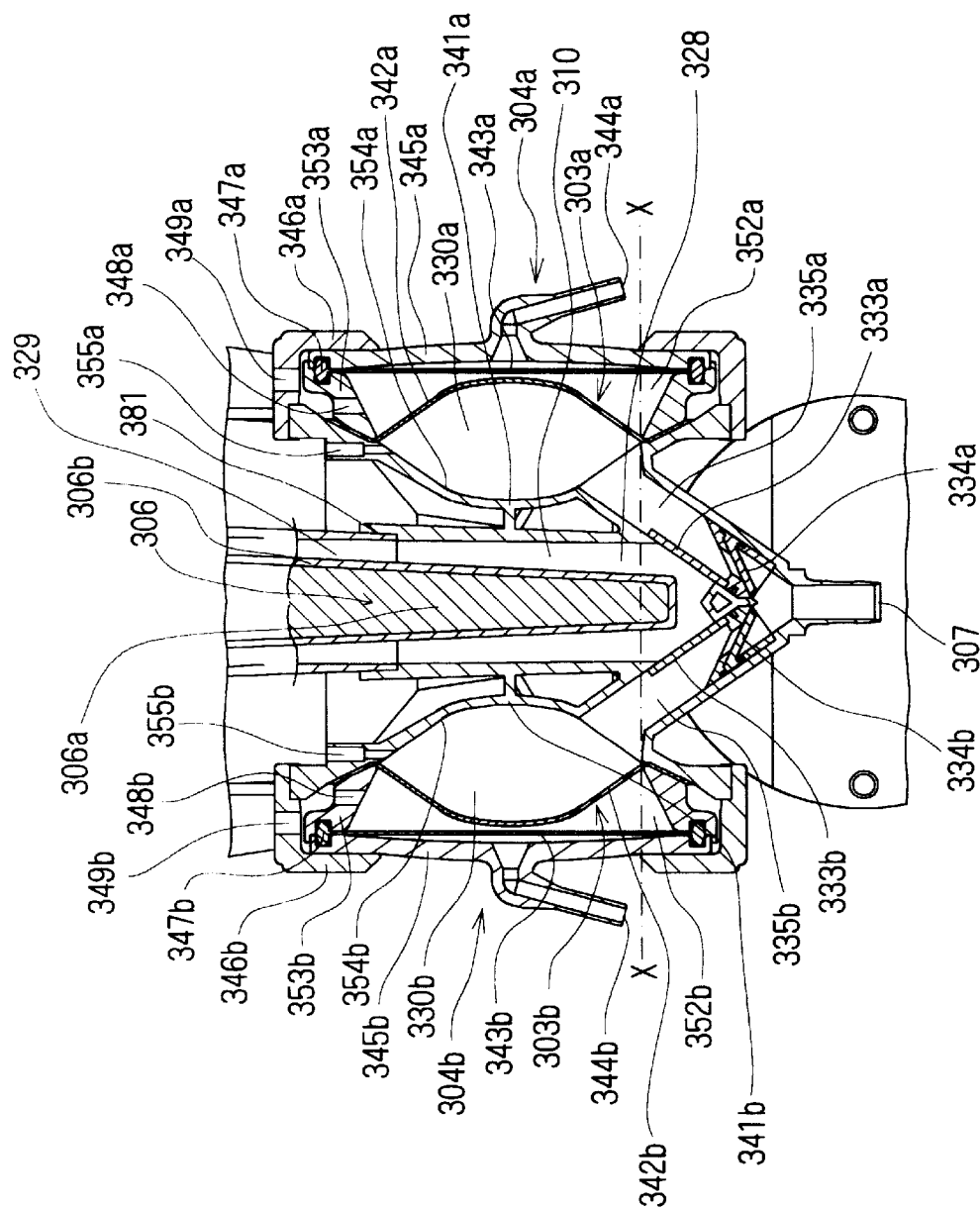
FIG. 47 is an enlarged sectional view of a blood delivery mechanism and a lower portion of the blood storing portion and their surroundings in the blood delivery mechanism-equipped blood reservoir tank shown in FIG. 44.
Figure 48:
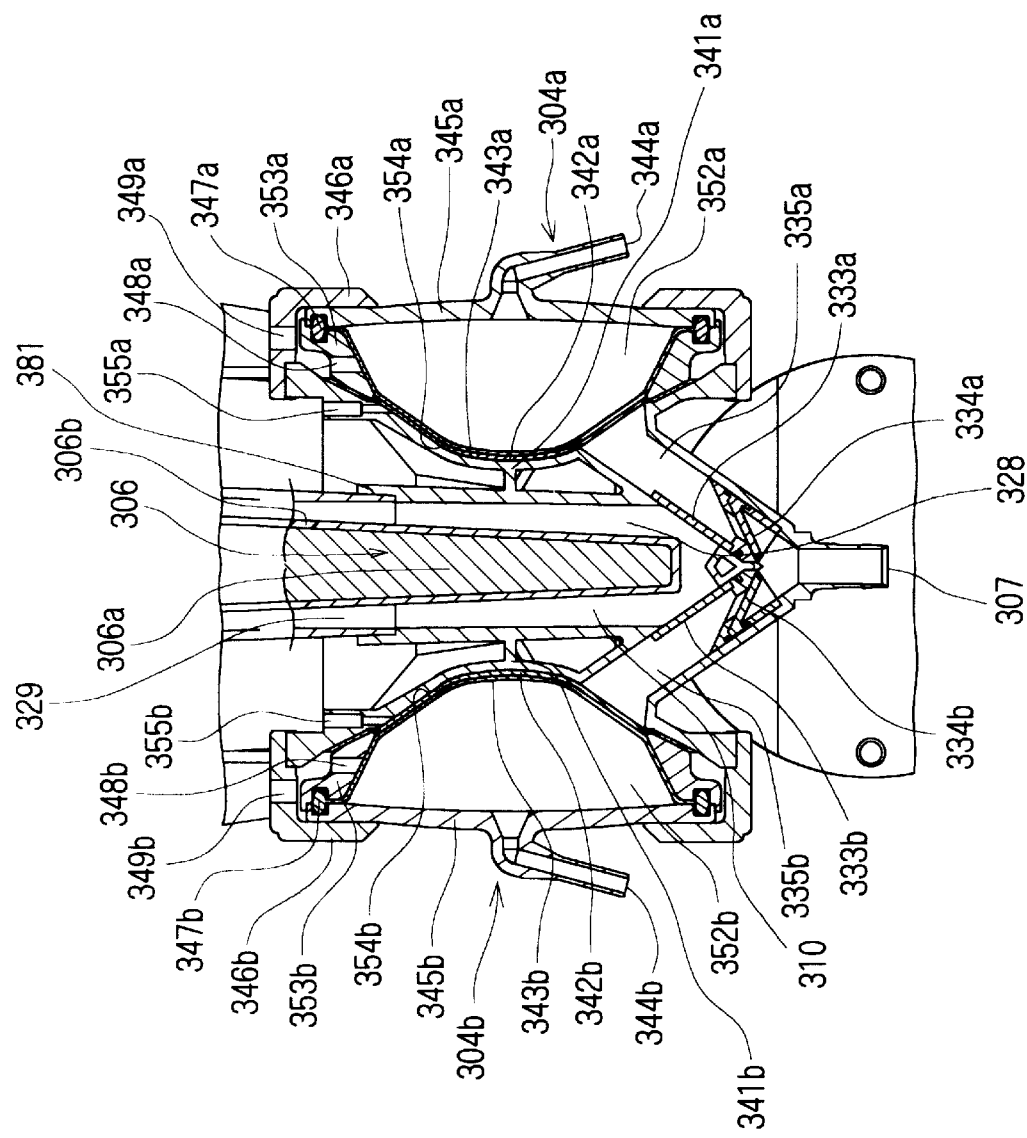
FIG. 48 is an enlarged sectional view of the blood delivery mechanism and a lower portion of the blood storing portion and their surroundings in the blood delivery mechanism-equipped blood reservoir tank shown in FIG. 44, at the time of blood delivery.
Figure 49:
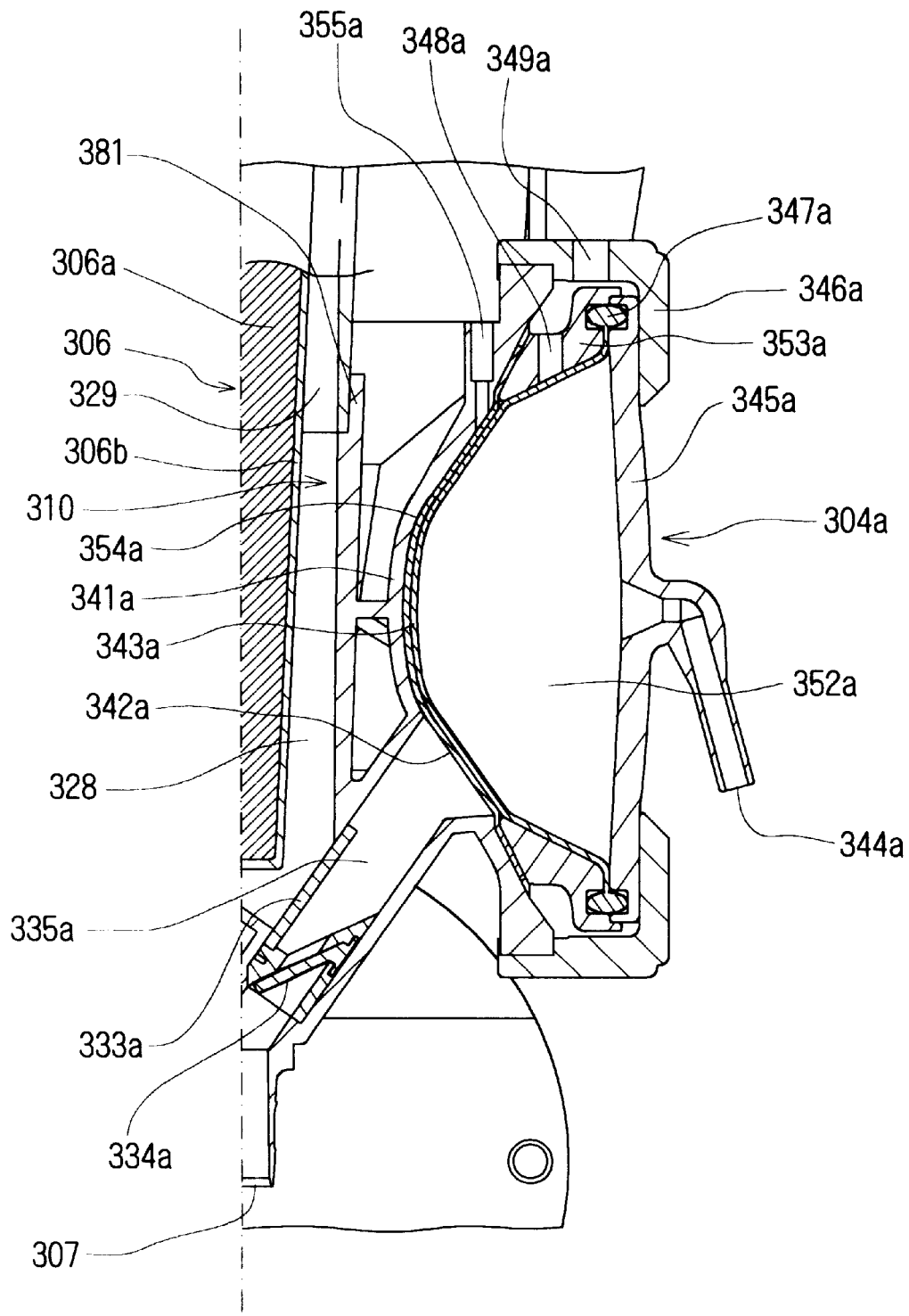
FIG. 49 is an enlarged sectional view of the blood delivery mechanism in the blood delivery mechanism-equipped blood reservoir tank shown in FIG. 44, at the time of blood delivery.

FIG. 44 is a front elevation of an embodiment of the blood delivery mechanism-equipped blood reservoir tank of the present invention, with an artificial lung connected. FIG. 45 is a side view of the blood delivery mechanism-equipped blood reservoir tank, with an artificial lung connected. FIG. 46 is a front elevation of the blood delivery mechanism-equipped blood reservoir tank shown in FIG. 44, with a fragmentary sectional view of a blood delivery mechanism and a lower portion of a blood storing portion and their surroundings. FIG. 47 is an enlarged sectional view of a blood delivery mechanism and a lower portion of the blood storing portion and their surroundings in the blood delivery mechanism-equipped blood reservoir tank shown in FIG. 44. FIG. 48 is an enlarged sectional view of the blood delivery mechanism and a lower portion of the blood storing portion and their surroundings in the blood delivery mechanism-equipped blood reservoir tank shown in FIG. 44, at the time of blood delivery. FIG. 49 is an enlarged sectional view of the blood delivery mechanism in the blood delivery mechanism-equipped blood reservoir tank shown in FIG. 44, at the time of blood delivery.

A blood delivery mechanism-equipped blood reservoir tank 300 according to an embodiment of the invention includes a blood storing portion 310, and blood reserving members 303a, 303b including blood reserving portions 330a, 330b that communicate with the blood storing portion 310. The blood reserving portions 330a, 330b reserve amounts of blood proportional to the amount of blood stored in the blood storing portion 310 when the amount of blood stored in the blood storing portion 310 becomes equal to or less than a predetermined value. The blood reserving portions 330a, 330b allow blood to flow out of the interiors thereof when pressed from outside. The blood delivery mechanism-equipped blood reservoir tank 300 further includes a bubble eliminating member 306 or a bubble removing member that is positioned inside the blood storing portion 310. A lower end of the bubble eliminating member 306 or the bubble removing member is positioned below lower ends of the blood reserving portions 330a, 330b of the blood reserving members 303a, 303b, that is, below an imaginary horizontal line X (FIG. 47) extending from the lower ends of the blood reserving portions 330a, 330b.

In other words, the bubble eliminating member 306 or the bubble removing member in the blood delivery mechanism-equipped blood reservoir tank 300 is provided so that the lower end of the bubble eliminating member 306 or the bubble removing member remains below the blood surface (on or below the blood surface) in the blood storing portion 310 even if the blood surface therein becomes the same height as the lower ends of the blood reserving portions 330a, 330b of the blood reserving members 303a, 303b.

In a further embodiment, the blood delivery mechanism-equipped blood reservoir tank 300 is equipped with a blood delivery mechanism that includes a blood storing portion 310, and blood reserving members 303a, 303b including blood reserving portions 330a, 330b that communicate with the blood storing portion 310. The blood reserving portions 330a, 330b reserve amounts of blood proportional to the amount of blood stored in the blood storing portion 310 when the amount of blood stored in the blood storing portion 310 becomes equal to or less than a predetermined value. The blood reserving portions 330a, 330b allow blood to flow out of interiors thereof when pressed from outside. The blood delivery mechanism further includes blood delivering drive units 304a, 304b that operate when blood is to be sent out of the interiors of the blood reserving members 303a, 303b. Each blood reserving member 303a, 303b includes a blood reserving member body portion 341a, 341b that is provided with an inwardly concavity surface portion 354a, 354b formed from a hard material into the shape of a bowl, and a flexible diaphragm 342a, 342b whose peripheral end portion is retained to a peripheral end portion of the concavity surface portion 354a, 354b of the blood reserving member body portion 341a, 341b in such a manner that the peripheral end portion of the flexible diaphragm 342a, 342b is inclined toward a central portion of the concavity surface portion 354a, 354b. The blood delivering drive unit 304a, 304b includes a blood reserving member-pressurizing portion 343a, 343b formed from an expandable sheet material, and a blood delivering fluid flow port 344a, 344b for expanding and contracting the blood reserving member-pressurizing portion 343a, 343b. The flexible diaphragm 342a, 342b is pressed against the concavity surface portion 354a, 354b of the blood reserving member body portion 341a, 341b, without forming any substantial bent point, when the blood reserving member-pressurizing portion 343a, 343b is expanded.

In a still further embodiment, In a further embodiment, the blood delivery mechanism-equipped blood reservoir tank 300 is equipped with a blood delivery mechanism that includes a blood storing portion 310, and blood reserving members 303a, 303b including blood reserving portions 330a, 330b that communicate with the blood storing portion 310. The blood reserving portions 330a, 330b reserve amounts of blood proportional to the amount of blood stored in the blood storing portion 310 when the amount of blood stored in the blood storing portion 310 becomes equal to or less than a predetermined value. The blood reserving portions 330a, 330b allow blood to flow out of interiors thereof when pressed from outside. The blood delivery mechanism further includes blood delivering drive units 304a, 304b that operate when blood is to be sent out of the interiors of the blood reserving members 303a, 303b. Each blood reserving member 303a, 303b includes a blood reserving member body portion 341a, 341b formed from a hard material, and a flexible diaphragm 342a, 342b whose peripheral end portion is retained to the blood reserving member body portion 341a, 341b. The blood delivering drive unit 304a, 304b includes a blood reserving member-pressurizing portion 343a, 343b formed from an expandable sheet material, and a blood delivering fluid flow port 344a, 344b for expanding and contracting (stretching) the blood reserving member-pressurizing portion 343a, 343b. The blood delivery mechanism-equipped blood reservoir tank 300 further includes a communication passage that connects a space 352a, 352b formed between the diaphragm 342a, 342b and the blood reserving member-pressurizing portion 343a, 343b to the outside.

In addition to the two blood reserving members 303a, 303b, the blood delivery mechanism-equipped blood reservoir tank 300 includes a blood reservoir tank portion 302 and blood flow passage portions 335a, 335b that connect between the blood reservoir tank portion 302 and the blood reserving members 303a, 303b, respectively. A heat exchanger-equipped artificial lung 305 is connected to a bottom surface of the blood reservoir tank portion 302 as in a hanging manner. A blood inlet of the heat exchanger-equipped artificial lung 305 is connected to a blood discharge opening 307 of the blood delivery mechanism-equipped blood reservoir tank 300 by a tube 351. In FIGS. 44 and 46, the tube 351 is removed. Provided outward of the diaphragms 342a, 342b are the blood delivering drive units 304a, 304b that press the diaphragms 342a, 342b directly or indirectly when operated.

The blood storing portion 310 is a space formed by a blood keeping portion 329 of the blood reservoir tank portion 302 and a blood keeping portion 328 of the blood delivery instrument 303. In the blood delivery mechanism-equipped blood reservoir tank 300, the upper ends of the diaphragms 342a, 342b are substantially at the same height as a joint portion 381 between the blood reservoir tank portion 302 and the blood delivery instrument 303, so that when the blood surface in the blood storing portion 310 lowers approximately below a lower end of the blood keeping portion 329 of the blood reservoir tank portion 302 (that is, when the amount of blood in the blood storing portion 310 becomes equal to or less than a predetermined value), the blood reserving members 303a, 303b reserve amounts of blood proportional to the amount of blood stored in the blood storing portion 310, and blood can be intermittently forced out of the delivery blood reserving members 303a, 303b by pressing the diaphragms 342 thereof from outside. Therefore, if the amount of blood in the blood storing portion 310 becomes small, blood is delivered in proportionally small amounts. Thus, if the amount of blood remaining becomes small, blood delivery is maintained in small amounts. Consequently, the need to interrupt blood delivery due to a reduction in the amount of blood remaining is eliminated, so that stagnation of blood in the extracorporeal blood circulation circuit can be avoided.

The blood reservoir tank portion 302 has a housing, as shown in FIGS. 44–46, which is composed of a blood reservoir tank portion housing main body 323a and a lid body 323b that are formed from a hard resin. The lid body 323b is fitted to an upper end of the housing main body 323a so as to cover an upper opening of the housing body 323a. The lid body 323b has blood inlets 321, 322 and an air discharge opening 327 as shown in FIGS. 44 and 45. The blood inlet 322 is connected to a cardiotomy line for conveying blood from an operation field. The blood inlet 321 is connected to a blood drainage line for conveying blood from a drainage cannula inserted into the heart ascending/descending veins of the patient.

The housing main body 323a and the lid body 323b may suitably be formed from, for example, polycarbonate, acrylic resin, polyethylene terephthalate, polyethylene, polypropylene, polystyrene, polyvinyl chloride, acryl-styrene copolymers, and acryl-butadiene-styrene copolymers, and the like. Particularly preferred among these are polycarbonate, acrylic resin, polystyrene, and polyvinyl chloride.

Disposed in the housing main body 323a are a blood filter (venous blood filter) 306 that is a combination of a bubble eliminating member and a bubble removing member for filtering blood incoming from the blood inlet port 321, and a cardiotomy blood filter (not shown) for filtering blood incoming from the blood inlet port 322. A lower end of the blood inlet port 321 extends into the blood storing portion 310, and is disposed inside the interior of the blood filter 306, so that the entire blood incoming from the blood inlet port 321 passes through the blood filter 306 and then flows into the blood storing portion 310. Therefore, a construction is made such that the dripping of blood incoming from the blood inlet port 321 directly onto the blood surface in the blood storing portion 310 is prevented. More specifically, the blood filter 306 is fixed to the inner surface of the lid body 323b and extends toward a lower portion of the blood storing portion 310 so that the blood filter 306 encloses the lower end portion of the blood inlet port 321 protruding into the blood storing portion 310.

The housing main body 323a has a downward projected portion 323c. The lower end portion of the blood filter 306 extends further downward of the projected portion 323c.

The interior of the blood filter 306 is filled with a bubble eliminating member 306a or a bubble removing member for eliminating air bubbles that may be contained in incoming blood. To form the bubble eliminating member 306a or the bubble removing member, various porous materials may suitably be used, including, but not limited to, foamed materials such as foamed polyurethane, foamed polyethylene, foamed polypropylene, foamed polystyrene and the like, mesh, woven fabrics, non-woven fabrics, porous ceramics, sintered materials of resin and the like. Materials having relatively small air passage resistance (pressure loss) are particularly preferred. If a material having less air passage resistance, for example, a foamed material such as foamed polyurethane or the like or other porous material, is used, the pore size is preferably approximately within the range of 20 µm to 10 mm and, more preferably, approximately within the range of 50 µm to 5 mm.

It is preferred that the bubble eliminating member 306a carries thereon a bubble eliminating agent that destroys bubbles when contacting them. A preferred bubble eliminating agent is silicone (silica-compounded type, oil type or the like). Examples of the method for causing to the bubble eliminating member 306a to support a bubble eliminating agent include, but are not limited to, a method wherein a bubble eliminating member is dipped in a liquid containing a bubble eliminating agent, and a method wherein a liquid containing a bubble eliminating agent is applied or sprayed to a bubble eliminating member, and then dried (for example, at 30° C. for 180 minutes).

The exterior of the bubble eliminating member 306a is covered with a filter member 306b. The filter member 306b removes foreign matter or air bubbles from blood. A preferred material for the filter member 306b is a porous material having a sufficiently high blood permeability. Examples of the porous material include mesh (net) materials, woven fabrics, non-woven fabrics and the like. Such materials may be used alone or in any desired combination (particularly, in the form of a laminate). It is preferred to use one or a combination of two or more of macromolecular materials that include polyesters such as PET, PBT or the like, polyolefins such as polyethylene, polypropylene, rayon, Tetron®, nylon (polyamide), and the like. It is also possible to use metallic materials such as aluminum, stainless steel or the like. Particularly preferred are polyesters, polypropylene, polyethylene and stainless steel. The opening size of a mesh used for the filter member 306b is preferably about 15–300 µm and, more preferably, about 20–200 µm. It is also preferred to subject the filter member 306b to a plasma treatment or a hydrophilic treatment such as coating with a hydrophilic macromolecular material or the like, in order to improve blood permeability.

The interior of the blood reservoir tank portion 302 forms a portion of the blood storing portion 310 for temporarily reserving blood, as shown in FIGS. 46 and 47. The capacity of the blood storing portion 310 is not particularly restricted. Normally, the capacity of the blood storing portion 310 is about 3,000 to 5,000 ml for adults and about 1,000 to 2,500 ml for children. The housing main body 323a is preferably substantially transparent or semi-transparent so that the amount and conditions of blood reserved therein may be readily observed. The downward projected portion 323c is a narrow portion with a reduced sectional area, whereby when the amount of blood reserved decreases, the amount of blood reserved or a change in the blood amount can be correctly and readily read. The blood reservoir tank portion 302 may be a soft type blood reservoir tank portion formed from a soft resin. Then, the blood reservoir tank portion 202 becomes a closed-type blood reservoir tank portion.

The blood delivery instrument 303 provided with the joint portion 381 to the blood reservoir tank portion 302 is firmly connected to a lower portion of the blood reservoir tank portion 302, as shown in FIGS. 47–49. The blood delivery instrument 303 includes the blood keeping portion 328, which forms a portion of the blood storing portion 310, and the two blood reserving members 303a, 303b, and the blood flow passage portions 335a, 335b connecting the blood reserving members 303a, 303b to the blood keeping portion 328 (the blood storing portion 310), and the blood discharge opening 307.

A first blood flow passage portion 335a communicates only with a first delivery blood reserving member 303a, and the second blood flow passage portion 335b communicates only with the second delivery blood reserving member 303b. Disposed at boundary sites between the blood storing portion 310 and the blood flow passage portions 335a, 335b are first check valves 333a, 333b that allow flow of blood from the blood storing portion 310 toward the blood flow passage portions 335a, 335b (that is, toward the blood delivery instrument 303) and restricts (prevents) the reverse flow of blood.

The first check valves 333a, 333b function as passage control members for blocking the communication between the blood storing portion 310 and the delivery blood reserving members 303a, 303b during the operation of the blood delivering drive units 304 as described below. The blood delivery instrument 303 is provided with the blood discharge opening 307 for communication with the blood flow passage portions 335a, 335b. Provided near the blood discharge opening 307 are second check valves 334a, 334b that allow blood flow toward a side downstream from the blood flow passage portions 335a, 335b (that is, downstream from the blood delivery instrument 303) and restricts the reverse flow of blood. The second check valves 334a, 334b function as passage control members for blocking reverse blood flow from the downstream side toward the delivery blood reserving members 303a, 303b (that is, into the blood flow passage portions 335a, 335b) when the blood delivering drive unit 304 is not operated.

Each check valve 333, 334 has a disc-shaped movable valve body a portion of which is secured to the housing. Preferably, the movable valve body of each check valve has a slightly less specific gravity than blood, and a hardness of about 3 to 7 on Shore A scale. The valve bodies are preferably formed from, for example, styrene-based elastomer oil gel, silicone gel or the like, to a thickness of about 0.5 to 5 mm.

Each of the delivery blood reserving members 303a, 303b includes the delivery blood reserving member body part 341a, 341b formed from a hard material, the flexible diaphragm 342a, 342b supported or fixed at its peripheral end to the delivery blood reserving member body part 341, and the blood reserving portion 330a, 330b (FIG. 47) formed between the delivery blood storing member body part 341a, 341b and the flexible diaphragm 342a, 342b.

FIG. 47 is an enlarged sectional view of the blood delivery mechanism and a lower portion of the blood storing portion and their surroundings in the blood delivery mechanism-equipped blood reservoir tank shown in FIG. 44, wherein the flexible diaphragms 342a, 342b are not pressed (blood is not being delivered). FIG. 48 is an enlarged sectional view of the blood delivery mechanism and a lower portion of the blood storing portion and their surroundings in the blood delivery mechanism-equipped blood reservoir tank shown in FIG. 44, wherein the flexible diaphragms 342a, 342b are pressed (blood is being delivered). FIG. 49 is a further enlarged sectional view of a portion shown in FIG. 48.

Each blood reserving member 303a, 303b includes the flexible diaphragm 342a, 342b forming a portion of the blood reserving portion 330a, 330b. The flexible diaphragms 342a, 342b are formed from a flexible material. The blood delivery mechanism-equipped blood reservoir tank 300 is provided with the blood delivering drive units 304a, 304b that operate, at the time of blood delivery, to deform the flexible diaphragms 342a, 342b, that is, deformable portions, so as to force blood out of the blood reserving members 303a, 303b. The blood delivering drive units 304a, 304b will be described below.

Each blood reserving member body portion 341a, 341b is provided with the inwardly concavity surface portion 354a, 354b having the shape of a bowl. A peripheral end portion of each flexible diaphragm 342a, 342b is retained to a peripheral end portion of the concavity surface portion 354a, 354b of the blood reserving member body portion 341a, 341b in such a manner that the peripheral end portion of the flexible diaphragm 342a, 342b is inclined toward a central portion of the concavity surface portion 354a, 354b. The entire inner surface of each blood reserving member body portion 341a, 341b, including the peripheral end portion, is receded in the form of a bowl. This receded or concave surface of each blood reserving member body portion 341a, 341b closely contacts the flexible diaphragm 342a, 342b at the time blood delivery. Thus, each blood reserving portion 330a, 330b formed between the flexible diaphragm 342a, 342b and the concave surface of the blood reserving member body portion 341a, 341b is a space that is variable in capacity. Diaphragm retaining annular members 353a, 353b have a shape that conforms to the shape of an inclined peripheral end portion of the corresponding blood reserving member body portions 341a, 341b (a portion slightly inward from the peripheral edge). That is, each diaphragm retaining annular member 353a, 353b is formed so that it can be disposed within the peripheral end portion of the corresponding blood reserving member body portion 341a, 341b, and so that the diaphragm retaining annular member becomes substantially parallel to the inclined portion of the blood reserving member body portion 341a, 341b slightly inward from the peripheral end portion thereof. An outer peripheral surface of each diaphragm retaining annular member 353a, 353b protrudes in a taper form and faces the blood reserving member body portion 341a, 341b.

The peripheral end portion of each flexible diaphragm 342a, 342b is clamped between the peripheral end portion of the blood reserving member body portion 341a, 341b (a portion slightly inward from the peripheral end) and the outer peripheral portion of the diaphragm retaining annular member 353a, 353b. Corresponding to the shape of the clamping portion, the peripheral end portion of each flexible diaphragm 342a, 342b is inclined toward a central portion of the concavity surface portion 354a, 354b of the blood reserving member body portion 341a, 341b. Therefore, even when pressed against the concavity surface portion 354a, 354b of the blood reserving member body portion 341a, 341b, each flexible diaphragm 342a, 342b does not form a substantial bent point, that is, does not cause stress concentration at any point therein. Therefore, the incidence of damages to or breakage of the flexible diaphragms 342a, 342b is very low despite being repeatedly pressed against the concavity surface portions 354a, 354b of the blood reserving member body portions 341a, 341b.

The inner peripheral surface of each diaphragm retaining annular member 353a, 353b forms an inclined annular surface that is inclined toward a central portion of the concavity surface portion 354a, 354b of the blood reserving member body portion 341a, 341b and that is substantially flush with the concavity surface portion 354a, 354b, when the diaphragm retaining annular member 353a, 353b is set to clamp the flexible diaphragm 342a, 342b. Each blood reserving member-pressurizing portion 343a, 343b, formed of a sheet material for pressing the flexible diaphragm 342a, 342b as described below, is restricted at its peripheral end portion by the inclined annular surface of the diaphragm retaining annular member 353a, 353b, when expanded. Therefore, at the time of depression of the diaphragm as shown in FIGS. 48 and 49, the blood reserving member-pressurizing portions 343a, 343b do not cause stress in the flexible diaphragms 342a, 342b, even at an annular contact end portion of each flexible diaphragm 342a, 342b (a portion adjacent to the distal peripheral end of the diaphragm retaining annular member 353a, 353b) at which stress is most likely to occur.

When the diaphragms are not depressed as shown in FIG. 47, each flexible diaphragm 342a, 342b bends at a clamped portion boundary therein (a portion adjacent to the distal peripheral end of the diaphragm retaining annular member 353a, 353b). However, in this state of the diaphragms, the flexible diaphragms 342a, 342b merely receive a pressure caused by a difference in height between the blood surfaces in the blood storing portion 310 and the blood reserving portions 330a, 330b, so that the flexible diaphragms 342a, 342b will not be damaged or broken.

Each blood reserving member 303a, 303b has an air vent port 355a, 355b that communicates with an upper portion of the blood reserving portion 330a, 330b. More specifically, each air vent port 355a, 355b is formed in an upper portion of the blood reserving member body portion 341a, 341b that is near the clamped portion boundary in the flexible diaphragm 342a, 342b. A tube provided with an open/close device, such as a three-way cock, is connected to each air vent port 355a, 355b. Using the tube, air removal is performed at the time of priming. It is also possible to connect an end of a tube with an open/close device, such as a three-way cock, connected to an intermediate portion thereof, to the air vent port 355a, 355b and the other end of the tube to an upper portion of the blood storing portion (a portion that normally remains above the blood surface). In this case, it becomes necessary to provide an upper side surface of the housing main body 323a or the lid body 323b with a connecting port. By providing such an air vent port communicating with an upper end of the blood reserving portion, it becomes very easy to remove air from the blood reserving member at the time of priming.

The maximum amount of blood that can be reserved by the delivery blood reserving members 303a, 303b (the maximum amount that can be contained therein, that is, the capacity thereof) varies depending on the capacity of the blood reservoir tank portion 302 used. However, the capacity of the delivery blood reserving members 303a, 303b is preferably about 20–500 mL and, particularly, about 50–500 mL. More preferably, the capacity thereof is about 50–300 mL and, particularly, about 80–300 mL.

The flexible diaphragms 342a, 342b have a shape corresponding to the shape of the inner surfaces of the concavity surface portions 354a, 354b of the blood reserving member body portions 341a, 341b. It is preferred that the pressure needed to deform each diaphragm 342a, 342b be equal to or less than 100 mmH$_2$O, whereby the flexible diaphragms 342a, 342b become more sensitive in responding to changes in the amount of blood stored in the blood storing portion 310, so that reservation of amounts of blood proportional to the amount of blood stored in the blood storing portion 310 is more reliably ensured. The pressure needed to deform each flexible diaphragm 342a, 342b is more preferably equal to or less than 50 mmH$_2$O.

The diaphragms 342a, 342b may be suitably formed from, for example, polyurethane, silicon-based polymers, polyvinyl chloride, and the like. Particularly preferred materials are polyurethane and silicon-based polymers, which are presently widely used for members that contact blood.

It is preferred that the diaphragms 342a, 342b be sufficiently soft. As an index of softness, compliance may be employed. The diaphragms 342a, 342b of the blood reserving members 303a, 303b have a compliance of, preferably, 2 ml/sec.mmHg or higher and, more preferably, within the range of 5–30 ml/sec.mmHg, when the blood surface in the blood storing portion 310 of the blood reservoir tank 300 is lower than the uppermost portion of the inner space of each of the delivery blood reserving members 303a, 303b, that is, when the pressure sensitivity (liquid surface sensitivity) of the delivery blood reserving members 303a, 303b is effective. It is further preferred that the diaphragms 342a, 342b of the delivery blood reserving members 303a, 303b have a compliance that is lower than the aforementioned value, when the blood surface in the blood storing portion 310 of the blood reservoir tank 300 is higher than the uppermost portion of the inner space of each of the delivery blood reserving members 303a, 303b. The resistance against blood inflow into the delivery blood reserving members 303a, 303b can be expressed by rate of blood inflow to the delivery blood reserving members 303a, 303b. The rate of blood inflow to the delivery blood reserving members 303a, 303b is preferably 20–600 ml/sec.

It is preferred to provide each flexible diaphragm 342a, 342b with a reinforcement (not shown) which covers the outside of the diaphragm and whose peripheral end portion is fixed to the blood reserving member body portion 341a, 341b. Preferably, the diaphragm and the reinforcement combined have the following properties: the pressure needed to deform the diaphragm is equal to or less than 100 mmH$_2$O; the rupture strength is equal to or greater than 5 kg/cm$^2$, and the diaphragm itself produces substantially no self-restoring force against deformation. It is preferred that the diaphragm and the reinforcement of each delivery blood reserving member 303a, 303b be not adhered to each other at all or except at the peripheral end portions thereof. The reinforcements may be provided in the form of a woven fabric, a non-woven fabric, a knitted fabric, a sheet material or the like. In view of strength, the form of a woven or knitted fabric is preferred. As for examples of the material of the reinforcements, polyethylene terephthalate, nylon 6, nylon 66, regenerated cellulose, polypropylene, fiber-reinforced plastics (FRP, with aramid fiber or the like), stainless steel, aluminum or the like may be suitably used. Particularly preferred are polyethylene terephthalate, nylon 6, nylon 66, regenerated cellulose and polypropylene.

Each delivery blood reserving member 303a, 303b has, in addition to the blood reserving portion 330a, 330b provided therein, a blood flow opening 331a, 331b which is positioned at a lower portion of the delivery blood reserving member 303a, 303b (at a lower end thereof) and which communicates with the blood reserving portion 330a, 330b. Each blood reserving member 303a, 303b communicates with the blood flow passage portion 335a, 335b through the blood flow openings 331a, 331b. The delivery blood reserving members 303a, 303b are positioned above the first check valves 333a, 333b defining boundary sites between the blood storing portion 310 and the blood flow passage portions 335a, 335b. The delivery blood reserving members 303a, 303b extend substantially vertically upward. If the blood surface in the blood storing portion 310 is below the uppermost end of the blood reserving portion 330a, 330b (inner space) of each delivery blood reserving member 303a, 303b, amounts of blood proportional to the blood surface in the blood storing portion 310 flow into the delivery blood reserving members 303a, 303b. If the blood surface in the blood storing portion 310 is above the uppermost end of the blood reserving portion 330a, 330b (inner space) of each delivery blood reserving member 303a, 303b, the maximum amount of blood flows into the delivery blood reserving members 303a, 303b (as shown in FIG. 47) since the maximum capacity of the delivery blood reserving members 303a, 303b is fixed.

More specifically, the delivery blood reserving members 303a, 303b receive pressure proportional to the amount of blood stored in the blood storing portion 310, thus forming pressure-sensitive containers. If the amount of blood (liquid surface) in the blood storing portion 310 is equal to or greater than a predetermined amount (in this embodiment, the blood surface in the blood storing portion 310 is above the uppermost end of the inner space of each delivery blood reserving member 303a, 303b), the amount of blood reserved in the delivery blood reserving members 303a, 303b is determined by the maximum capacity thereof, not by the pressure corresponding to the amount of blood stored in the blood storing portion 310. That is, the delivery blood reserving members 303a, 303b reserve the maximum amount of blood. If the amount of blood stored in the blood storing portion 310 is equal to or less than the predetermined amount (in this embodiment, the blood surface in the blood storing portion 310 is below the uppermost end of the inner space of each delivery blood reserving member 303a, 303b), the pressure sensitivity of the delivery blood reserving members 303a, 303b becomes effective so that the delivery blood reserving members 303a, 303b reserve amounts of blood proportional to the amount of blood stored in the blood storing portion 310 (that is, the height of the blood surface in the blood storing portion 310). In short, the delivery blood reserving members 303a, 303b function to automatically reserve amounts of blood proportional to the amount of blood stored in the blood storing portion 310 when the amount of blood in the blood storing portion 310 is equal to or less than the predetermined value.

The delivery blood reserving members 303a, 303b do not spontaneously draw in blood, that is, do not substantially have self-shape-restoring characteristic. If the delivery blood reserving members 303a, 303b were formed so that the members have a preset shape and self-shape-restoring characteristic, the delivery blood reserving members 303a, 303b would restore their preset shape when the load from the drive members for forcing blood out of the members 303a, 303b is removed after blood is thereby forced out. Then the self-restoring force of the delivery blood reserving members 303a, 303b would cause a suction force, whereby blood would be drawn back into the delivery blood reserving members 303a, 303b from the side of the blood reservoir tank portion 302. In short, the delivery blood reserving members 303a, 303b would retain a certain minimum level of blood, below which the pressure sensitivity could not be effective.

In the blood delivery mechanism-equipped blood reservoir tank according to this embodiment, the blood filter 306 extends through the blood keeping portion 329 of the blood reservoir tank portion 302, to the blood keeping portion 328 of the blood delivery instrument 303. The lower end of the blood filter 306 is positioned below the lower ends of the blood reserving portions 330a, 330b. That is, the lower end of the blood filter 306 is positioned so as to remain below the blood surface in the blood storing portion 310 even if the blood surface lowers to the same height as the lower ends of the blood reserving portions 330a, 330b of the blood reserving members 303a, 303b.

Therefore, even when the amount of blood stored in the blood storing portion 310 decreases to or below a predetermined value so that the blood reserving members 303a, 303b function to reserve amounts of blood proportional to the amount of blood in the blood storing portion 310, there occurs substantially no bubbling due to flood inflow because the lower end of the blood filter 306 is positioned below the blood surface in the blood storing portion 310. For the same reason, substantially no or very little bubbling due to blood inflow occurs when the amount of blood in the blood storing portion 310 increases back to or above the predetermined value.

The capacity of each blood flow passage portion 335a, 335b (that is, a blood passage partially defined by the blood inlet of the blood reserving portion 330a, 330b and the first and second check valves 333a, 334a or 333b, 334b) is preferably equal to or less than 150 mL. Each blood flow passage portion 335a, 335b represents a blood passage partially defined by the first and second check valves 333a, 334a or 333b, 334b and the blood inlet of the blood reserving portion 330a, 330b of the blood reserving member 303a, 303b (the inner surface of the diaphragm 342a, 342b) when the flexible diaphragm 342a, 342b are closed or depressed.

The minimum sectional area of each blood flow passage portion 335a, 335b is equal to or greater than 1.0 cm$^2$. With such a sectional area of each blood flow passage portion 335a, 335b, the pressure sensitivity of the blood reserving members 303a, 303b will not be impeded, but can be made sufficiently high so that the blood reserving members 303a, 303b will reserve amounts of blood proportional to the amount of blood in the blood storing portion 310 (that is, the blood surface in the blood reservoir tank portion 302) when the amount of blood stored is equal to or less than a predetermined value. It is preferred that the pressure loss of each blood flow passage portion 335a, 335b (the pressure loss of a blood passage) be as small as possible. In this invention, the pressure loss is preferably 330 mmH$_2$O or less and, particularly, 110 mmH$_2$O and, more preferably, 100 mmH$_2$O. With such a pressure loss, a sufficiently high pressure sensitivity and good operation can be achieved. The minimum sectional area of each blood flow passage portion 335a, 335b is more preferably 1.5 cm$^2$ or greater, whereby a favorable pressure sensitivity of the blood reserving members can be ensured.

It is also preferred that the capacity of each blood flow passage portion 335a, 335b be smaller than the maximum amount of blood that can be reserved in the blood reserving members 303a, 303b (the maximum amount that can be contained therein), whereby the entire volume of blood in the blood flow passage portion 335a, 335b can be forced out thereof by blood discharged from the blood reserving member 303a, 303b, thereby minimizing blood stagnation in the blood flow passage portion 335a, 335b.

The blood reserving member body portions 341a, 341b may suitably be formed from, for example, polycarbonate, acrylic resin, polyethylene terephthalate, polyethylene, polypropylene, polystyrene, polyvinyl chloride, acryl-styrene copolymers, and acryl-butadiene-styrene copolymers, and the like. Particularly preferred materials are polycarbonate, acrylic resin, polystyrene, and polyvinyl chloride. In this embodiment, the blood reserving member body portion 341a and the blood flow passage portion 335a are unitarily formed as a single member. Similarly, the blood reserving member body portion 341b and the blood flow passage portion 335b are unitarily formed. However, it is also possible to separately provide a blood reserving member body part and a blood flow passage part and then connect them.

The blood delivering drive units 304a, 304b are disposed outside the blood delivery instrument 303 in such a manner as to cover the blood reserving members 303a, 303b, respectively. The blood delivering drive units 304a, 304b and the blood delivery instrument 303 form a blood delivery mechanism.

Each blood delivering drive unit 304a, 304b is provided with the blood reserving member-pressurizing portion 343a, 343b formed of an expandable sheet material for operating to deliver blood out of the corresponding blood reserving member 303a, 303b. Each blood delivering drive unit 304a, 304b further includes a header 345a, 345b provided with the blood delivering fluid flow port 344a, 344b extending diagonally downwardly outward from a central portion of the header 345a, 345b, and a securing ring 346a, 346b for securing the header 345a, 345b to the blood reserving member body portion 341a, 341b.

Each blood reserving member-pressurizing portion 343a, 343b has an expanded or thickened peripheral end portion 347a, 347b. The thickened peripheral end portion 347a, 347b and an annular portion slightly inwardly of the thickened peripheral end portion 347a, 347b are clamped between the peripheral end portion of the header 345a, 345b and the peripheral end portion of the diaphragm retaining annular member 353a, 353b, and thereby substantially airtightly retained. Each diaphragm retaining annular member 353a, 353b retains both the diaphragm 342a, 342b and the blood reserving member-pressurizing portion 343a, 343b, and controls excessive expansion of the diaphragm 342a, 342b. Since the blood reserving member-pressurizing portion 343a, 343b of each blood delivering drive unit 304a, 304b is an expandable or stretchable sheet member for expansion and contraction achieved by a fluid, the incidence of damaging or breaking the diaphragm by pressurization thereon is minimum. Furthermore, a relatively inward peripheral end portion of each blood reserving member-pressurizing portion 343a, 343b is restricted by the inclined annular surface of the diaphragm retaining annular member 353a, 353b when the blood reserving member-pressurizing portion 343a, 343b is expanded.

The inclined annular surface of each diaphragm retaining annular member 353a, 353b is inclined toward a central portion of the concavity surface portion 354a, 354b of the blood reserving member body portion 341a, 341b and that is substantially flush with the concavity surface portion 354a, 354b. Therefore, the blood reserving member-pressurizing portions 343a, 343b do not cause stress in the flexible diaphragms 342a, 342b, even at an annular contact end portion of each flexible diaphragm 342a, 342b (a portion adjacent to the distal peripheral end of the diaphragm retaining annular member 353a, 353b) at which stress is most likely to occur.

For use, a blood delivering fluid supply machine (not shown) is connected to the blood delivering fluid flow ports 344a, 344b. By supplying and discharging a fluid (liquid or gas) by a compressor provided in the blood delivering fluid supply machine, the expanding and contracting driving of the blood reserving member-pressurizing portions 343a, 343b is repeated. The blood reserving member-pressurizing portion 343a, 343b of each blood delivering drive unit 304a, 304b does not contact the diaphragm 342a, 342b of the blood reserving member 303a, 303b when not expanded (contracted) as shown in FIG. 47. When expanded, the blood reserving member-pressurizing portion 343a, 343b of each blood delivering drive unit 304a, 304b pressurizes the diaphragm 342a, 342b of the blood reserving member 303a, 303b in cooperation with the blood reserving member body portion 341a, 341b, thereby discharging blood out of the interior of the blood reserving member 303a, 303b (the interior of the blood reserving portion 330a, 330b).

The spaces 352a, 352b between the blood reserving members 303a, 303b (the diaphragms 342a, 342b) and the blood reserving member-pressurizing portions 343a, 343b (that is, spaces between the blood reserving members 303a, 303b and the blood delivering drive units 304a, 304b) are in communication with the outside. More specifically, each space 352a, 352b formed between the blood reserving member 303a, 303b and the blood reserving member-pressurizing portion 343a, 343b is in communication with the outside through a passage partially formed by an opening 348a, 348b that is formed in the diaphragm retaining annular member 353a, 353b (a component member of the blood delivering drive unit 304a, 304b) and an opening 349a, 349b that is formed in the securing ring 346a, 346b. Thus, in this embodiment, each blood delivering drive unit 304a, 304b has a passage for connecting the space between the blood reserving member 303a, 303b and the blood delivering drive unit 304a, 304b to the outside.

The shape and the manner of communication of the spaces 352a, 352b between the blood reserving members 303a, 303b and the blood reserving member-pressurizing portions 343a, 343b are not restricted by what is described above, as long as the spaces 352a, 352b communicate with the outside and do not form closed spaces. For example, if the securing rings 346a, 346b are not air-tightly fixed to the blood reserving member body portions 341a, 341b, communication passages for the spaces 352a, 352b may be formed by merely forming an opening only in each diaphragm retaining annular member 353a, 353b for communication with the outside. It is also possible to form a plurality of openings in a diaphragm retaining annular member 353a, 353b. In this case, the spaces 352a, 352b do not form tightly closed spaces, the spaces serve as decompression spaces when the blood reserving member-pressurizing portions 343a, 343b contract from an expanded state, thereby preventing the blood reserving members 303a, 303b from drawing in blood.

Preferred examples of the elastic material used to form the blood reserving member-pressurizing portions 343a, 343b include synthetic rubbers such as urethane rubber, silicone rubber, butadiene rubber and the like, natural rubbers such as latex rubber and the like, and elastomers such as olefin-based elastomer, amide-based elastomer, styrene-based elastomer (for example, styrene-butadiene-styrene copolymers, styrene-isoprene-styrene copolymers, styrene-ethylenebutylene-styrene copolymers), polyurethane elastomer and the like.

The blood delivering drive unit may adjust the amount of blood forced out of the blood reserving member by adjusting the amount or pressure of the fluid fed into the drive unit. The amount of blood delivered may be easily changed by adjusting the amount or pressure of the fluid fed into the blood delivering drive unit while fixing the number of times of driving the blood delivering drive unit in every predetermined length of time.

The blood delivery mechanism-equipped blood reservoir tank 300 of this embodiment is equipped with the two sets of the delivery blood storing member 303 and the blood delivering drive unit 304, as described above. Further, the two separate blood flow passage portions 335 (335a, 335b) are provided without communication therebetween, as shown in FIGS. 47 and 48. By providing two or more sets thereof in this manner, the capacity of each delivery blood reserving member 303a, 303b and each blood delivering drive unit 304a, 304b can be reduced, so that the blood inflow and discharge response improves. Furthermore, if two or more sets of the delivery blood storing member 303 and the blood delivering drive unit 304 are provided, good blood flow may be achieved by shifting the expanding strokes of the blood delivering drive units 304a, 304b in timing from each other. If the expanding timing of the blood delivering drive units 304a, 304b is thus shifted, flow of blood from one blood reserving member to the other in this embodiment never occurs since the individual blood reserving members are provided with the separate blood flow passage portions 335a, 335b. The construction of the invention is not limited by this embodiment. The number of sets of the delivery blood reserving member and the blood delivering drive unit may also be one, or three or more. In addition, although the blood delivering drive units 304a, 304b in this embodiment repeat expansion and contraction through fluid operation, the blood delivering drive unit is not restricted by this driving manner. For example, the blood delivering drive unit may mechanically drive a pressurizing plate to pressurize the blood reserving member.

If two sets of the delivery blood reserving member and the blood delivering drive unit are provided as in blood delivery mechanism-equipped blood reservoir tank 300 and, furthermore, the individual blood delivering drive units can be separately controlled by a fluid supply machine for blood delivery, it becomes possible to select the form of blood flow for delivery, more specifically, select a pulse flow or a constant flow, considering the conditions of a patient, the type of the artificial lung used or the like. It becomes also possible to change the form of delivery blood flow while in use. More specifically, a substantially constant blood flow can be achieved by shifting the phases of the blood flow out of the individual delivery blood reserving members 303a, 303b by substantially 180° from each other, that is, by shifting the phases of fluid flowing into and out of the blood delivering drive units 304a, 304b by substantially 180° from each other. A good pulse flow can be achieved by setting the phases of blood flow out of the individual blood reserving members 303a, 303b to substantially the same phase or within ±30°, that is, by setting the phases of fluid flowing into and out of the blood delivering drive units 304a, 304b to substantially the same phase or within ±30°. If three or more sets of the delivery blood storing member and the blood delivering drive unit are provided, the form of blood flow will become a substantially constant flow by shifting the phases of blood flow out of the individual delivery blood reserving members by an angle obtained by dividing 360° by the number of the sets provided.

In the blood delivery mechanism-equipped blood reservoir tank 300, the diaphragms 342a, 342b of the blood reserving members 303a, 303b are surrounded by the headers 345a, 345b and the like, and are not exposed to outside. Thus, the function of protective covers for the diaphragms are provided.

Figure 53:
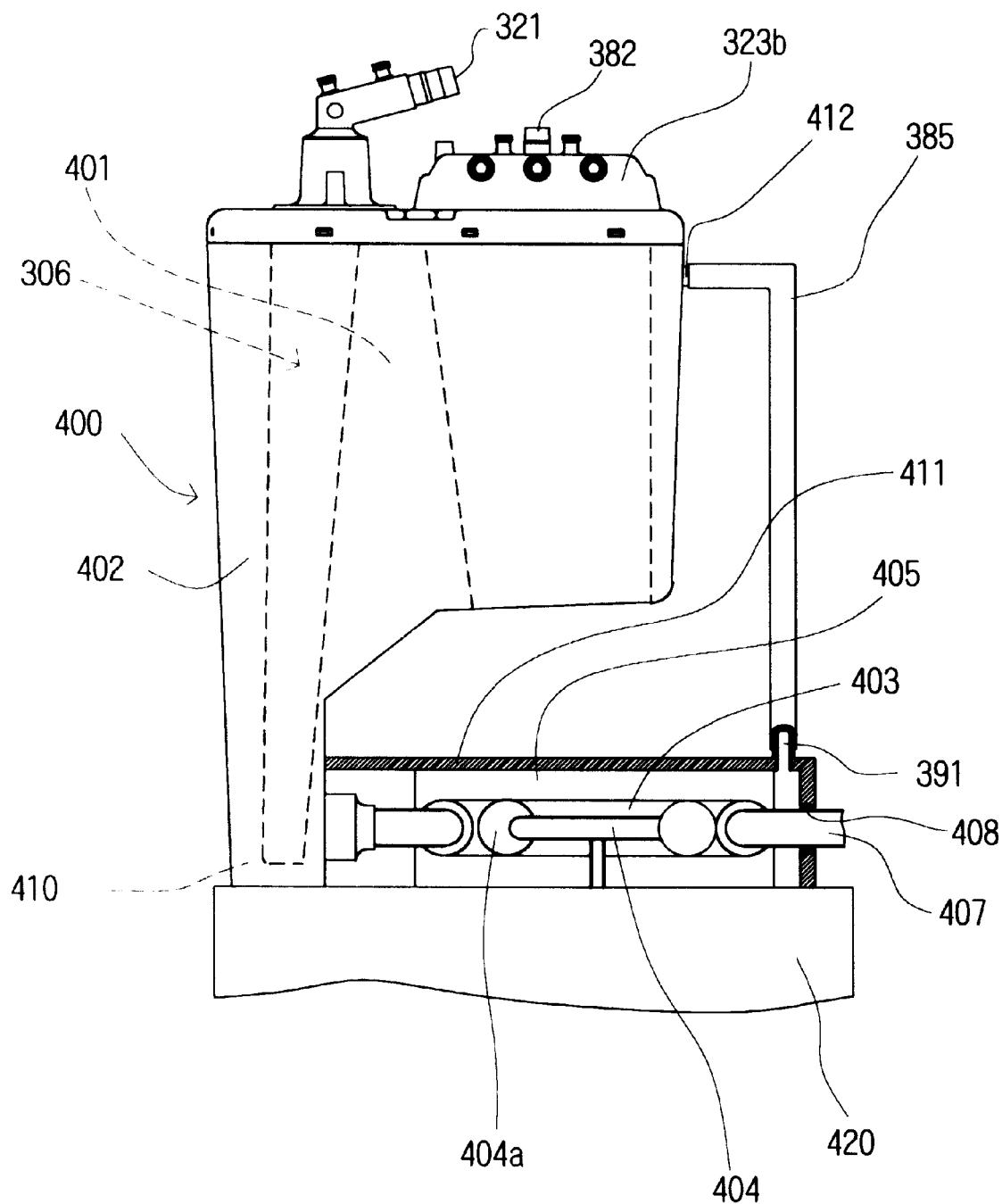
FIG. 53 is a partially cut-away side view of a blood delivery mechanism-equipped blood reservoir tank according a further embodiment of the present invention.
Figure 54:
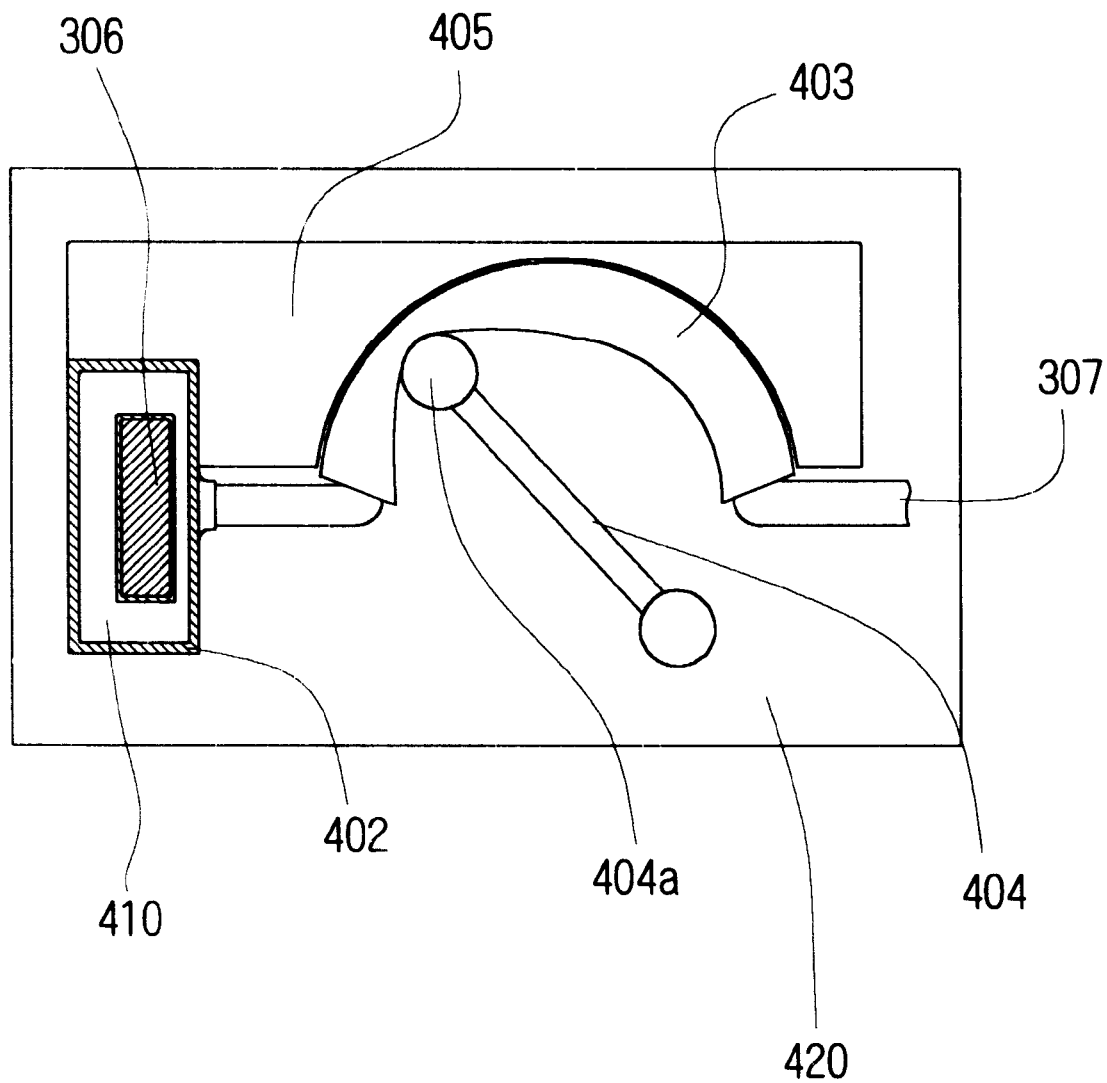
FIG. 54 is a sectional view of a lower portion of the blood delivery mechanism-equipped blood reservoir tank shown in FIG. 53, taken on a horizontal plane, wherein a case member is removed.

The blood delivery mechanism-equipped blood reservoir tank of the present invention is not restricted by the foregoing embodiment, but may be provided as a blood delivery mechanism-equipped blood reservoir tank 400 as shown in FIGS. 53 and 54. FIG. 53 is a partially cut-away side view of a blood delivery mechanism-equipped blood reservoir tank according a further embodiment of the present invention. FIG. 54 is a sectional view of a lower portion of the blood delivery mechanism-equipped blood reservoir tank shown in FIG. 53, taken on a horizontal plane, wherein a case member is removed.

The blood delivery mechanism-equipped blood reservoir tank 400 of this embodiment differs from the blood delivery mechanism-equipped blood reservoir tank 300 of the foregoing embodiment in the mechanism of blood reserving members and blood reserving member-pressurizing portions.

Similar to the blood delivery mechanism-equipped blood reservoir tank 300 of the foregoing embodiment, the blood delivery mechanism-equipped blood reservoir tank 400 of this embodiment includes a blood storing portion 410, and a blood reserving member including a blood reserving portion that communicates with the blood storing portion 410. The blood reserving portion reserves amounts of blood proportional to the amount of blood stored in the blood storing portion when the amount of blood stored in the blood storing portion is equal to or less than a predetermined value. The blood reserving portion allows blood to flow out of the interior thereof when pressed from outside. The blood reserving member is a soft tubular body 403. A pump 404 is provided as a blood reserving member-pressurizing member for pressurizing the soft tubular body 403 to force blood out of the interior of the soft tubular body 403. The blood delivery mechanism-equipped blood reservoir tank 400 further includes a case member 411 that substantially air-tightly separates, from the outside, the soft tubular body 403 and a pumping portion for pressurizing the soft tubular body 403 to deliver blood therefrom, and a communication passage (formed by a communication member 385) connecting the interior of the case member 411 and an upper portion of the blood storing portion in communication.

In the blood delivery mechanism-equipped blood reservoir tank 400, the blood reserving member is formed by the soft tubular body 403 extending horizontally. The soft tubular body 403 has substantially no self-restoring characteristic, as in the blood reserving members described above. Therefore, if the amount of blood stored in the blood storing portion 410 decreases so that the blood surface in the blood storing portion 410 becomes lower than an upper end of the soft tubular body 403, the soft tubular body 403 reserves amounts of blood corresponding to the height of blood surface, thus performing pressure-sensitive operation. The soft tubular body 403 is connected with a tube 407 that forms a blood discharge opening.

Employed as a blood reserving member-pressurizing member is the pump 404, which pressurizes the soft tubular body 403 to force blood out of the interior thereof. The pump 404 in this embodiment is a roller pump. The pump may also be a peristaltic pump. The pump 404 delivers blood from the soft tubular body 403 in a squeezing manner such that a squeezed or compressed portion achieves a closed state in the soft tubular body 403. Therefore, the two check valves provided in the blood delivery mechanism-equipped blood reservoir tank 300 of the foregoing embodiment are not necessary in this embodiment. The blood delivery mechanism-equipped blood reservoir tank 400 further includes a soft tubular body-supporting portion 405. The soft tubular body 403 is squeezed between the soft tubular body-supporting portion 405 and a roller 404a of the roller pump 404.

As in the blood delivery mechanism-equipped blood reservoir tank 300, a bubble eliminating member 306 in the blood delivery mechanism-equipped blood reservoir tank 400 extends to a proximity of a bottom of the blood reservoir tank portion 302, and the lower end of thereof is positioned below a lower end of the soft tubular body 403, that is, a blood reserving member. In other words, the blood filter 306 is provided so that the lower end thereof remains below the blood surface (on or below the blood surface) in the blood storing portion 410 even if the blood surface therein becomes the same height as the lower ends of the soft tubular body 403.

Therefore, even when the amount of blood stored in the blood storing portion 410 decreases to or below a predetermined value so that the soft tubular body 403 functions to reserve amounts of blood proportional to the amount of blood in the blood storing portion 410, there occurs substantially no bubbling due to flood inflow because the lower end of the blood filter 306 is positioned below the blood surface in the blood storing portion 410. For the same reason, substantially no or very little bubbling due to blood inflow occurs when the amount of blood in the blood storing portion 410 increases back to or above the predetermined value.

The blood delivery mechanism-equipped blood reservoir tank 400 may also be provided with two or more sets of the blood reserving member and the blood reserving member-pressing member.

The blood delivery mechanism-equipped blood reservoir tank 400 is provided with the case member 411 that substantially air-tightly separates, from the outside, the soft tubular body 403 and a pumping portion for pressurizing the soft tubular body 403 to deliver blood therefrom, and the communication passage 385 connecting the interior of the case member 411 and an upper portion of the blood storing portion 410 in communication. More specifically, the case member 411 is mounted on the pump main body 404, and substantially air-tightly separates the soft tubular body-supporting portion 405 and the roller 404a and the like of the roller pump 404 from the outside. Therefore, the space enclosing at least the soft tubular body 403 is not in direct communication with the outside. As shown in FIG. 53, the blood delivery mechanism-equipped blood reservoir tank 400 has a suction device connecting port 382, and a communication member connecting port 412 forming a communication passage (communicating with the blood storing portion 401). The case member 411 has a communication member connecting port 391. The communication member connecting port 412 is provided with an air-permeable and blood-impermeable member (not shown). The blood-impermeable member may be a membrane filter, a sintered filter or the like. It is preferred that the pressure loss of the blood-impermeable member be small. The communication member connecting port 412 may be positioned at any site where the possibility of contact with blood is small. Although the communication member connecting port 412 is provided so as to communicate with an uppermost end of the interior of the blood reservoir tank in FIG. 53, this disclosed construction is not restrictive. For example, the communication member connecting port 412 may also be provided in an upper portion of a housing 323a of the blood reservoir tank. The case member 411 has an opening for air-tightly holding the tube 407 (extending therethrough). The opening of the case member 411 is provided with an O-ring 408 formed from an elastomer or rubber such as silicone rubber, urethane rubber or the like.

The communication member connecting ports 391 and 412 are connected by the communication member 385. The communication member 385 may be a hard or soft tube.

Lately, the conveyance of blood into the blood reservoir tank and the drainage of blood from a patient are often performed by a method using a suction device (negative pressure applying device) connected to the blood reservoir tank. When this device is operated, the pressure in the blood reservoir tank portion becomes negative, and the negative pressure affects the interior of a soft tubular body. That is, the soft tubular body becomes exposed to a negative pressure inside due to the operation of the suction device (negative pressure applying device), while receiving the atmospheric pressure on the outside. Therefore, the soft tubular body is pressed by a differential pressure between the inside and outside pressures, so that the liquid surface-sensitive (pressure-sensitive, pre-load-sensitive) function of the soft tubular body, that is, the delivery blood reserving member, may be impeded. However, in the aforementioned construction in which the space (the interior of the case member 411) enclosing the blood storing portion 401 and the soft tubular body 403 are connected by the communication member 385, when suction from the blood reservoir tank portion is performed so that the pressure in the blood reservoir tank portion becomes negative, the pressure in the case member 411 simultaneously becomes negative, thereby avoiding the impeding of the pre-load-sensitivity performance of the soft tubular body 403 corresponding to the amount of blood stored (the height of liquid surface). The communication member connecting port 391 may also be provided with an air-permeable and blood-impermeable member (not shown). The blood-impermeable member may be a membrane filter, a sintered filter or the like. It is preferred that the pressure loss of the blood-impermeable member be small.

A still embodiment of the blood delivery mechanism-equipped blood reservoir tank of the invention will be described with reference to FIGS. 50–52.

Figure 50:
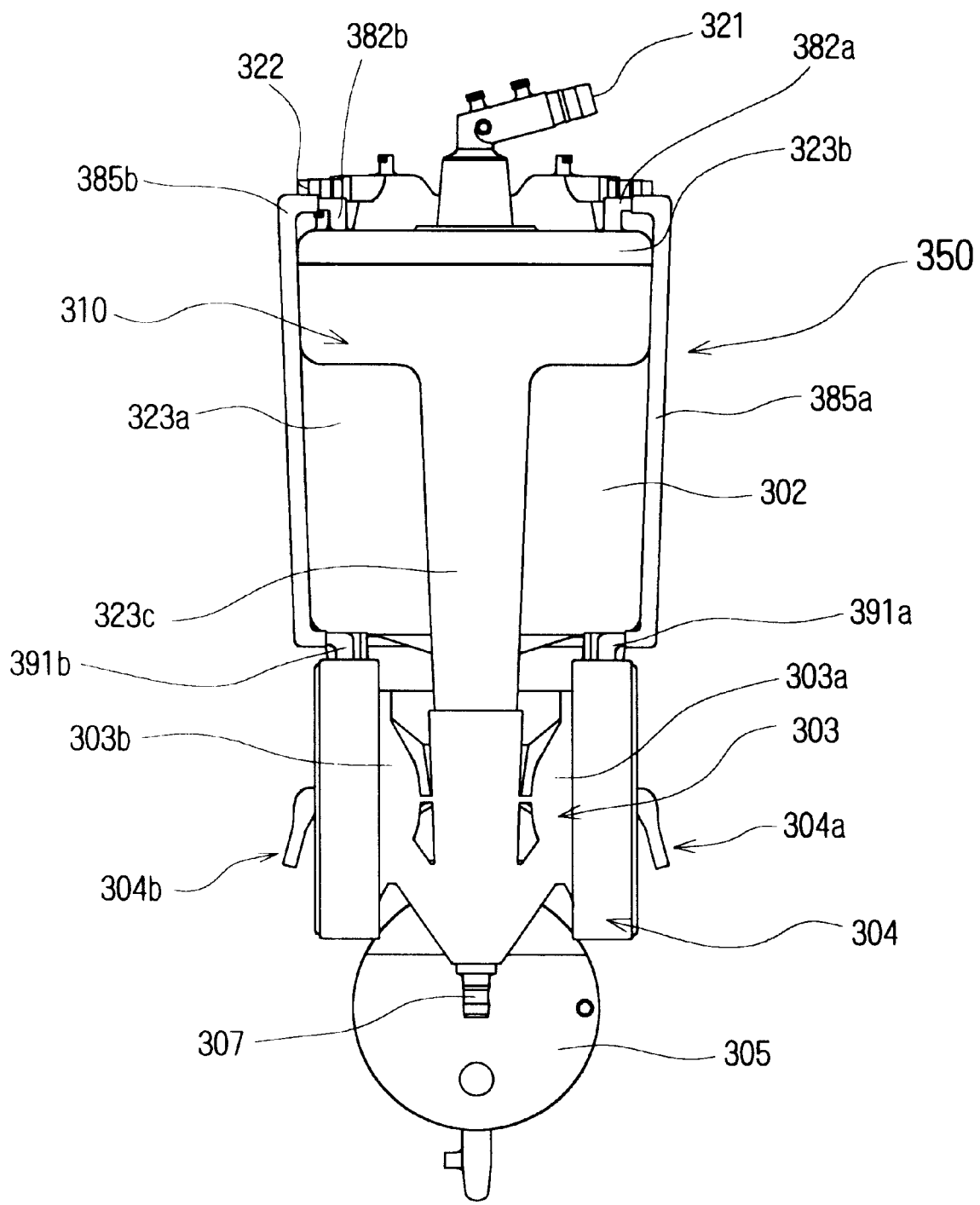
FIG. 50 is a front elevation of a blood delivery mechanism-equipped blood reservoir tank according to a further embodiment of the present invention, with an artificial lung connected.

FIG. 50 is a front elevation of a blood delivery mechanism-equipped blood reservoir tank 350 according to an embodiment of the present invention, with an artificial lung connected. FIG. 51 is a side view of the blood delivery mechanism-equipped blood reservoir tank according to the embodiment, with the artificial lung connected. FIG. 52 is an enlarged sectional view of the blood delivery mechanism and a lower portion of a blood storing portion and their surroundings in the blood delivery mechanism-equipped blood reservoir tank shown in FIG. 50, at the time of blood delivery.

The blood delivery mechanism-equipped blood reservoir tank 350 of this embodiment is substantially the same in a basic construction as the blood delivery mechanism-equipped blood reservoir tank 300 described above. Like portions are represented by like reference characters in the drawings, and will not be described again. The blood delivery mechanism-equipped blood reservoir tank 350 differs from the blood delivery mechanism-equipped blood reservoir tank 300 in that the blood delivery mechanism-equipped blood reservoir tank 350 includes a communication passage for communication between a space formed between the diaphragm and the blood reserving member-pressurizing portion and an upper portion of the blood storing portion. Therefore, the space between the diaphragm and the blood reserving member-pressurizing portion is not in direct communication with the outside in this embodiment. The communication passage will be described in detail below.

Figure 51:
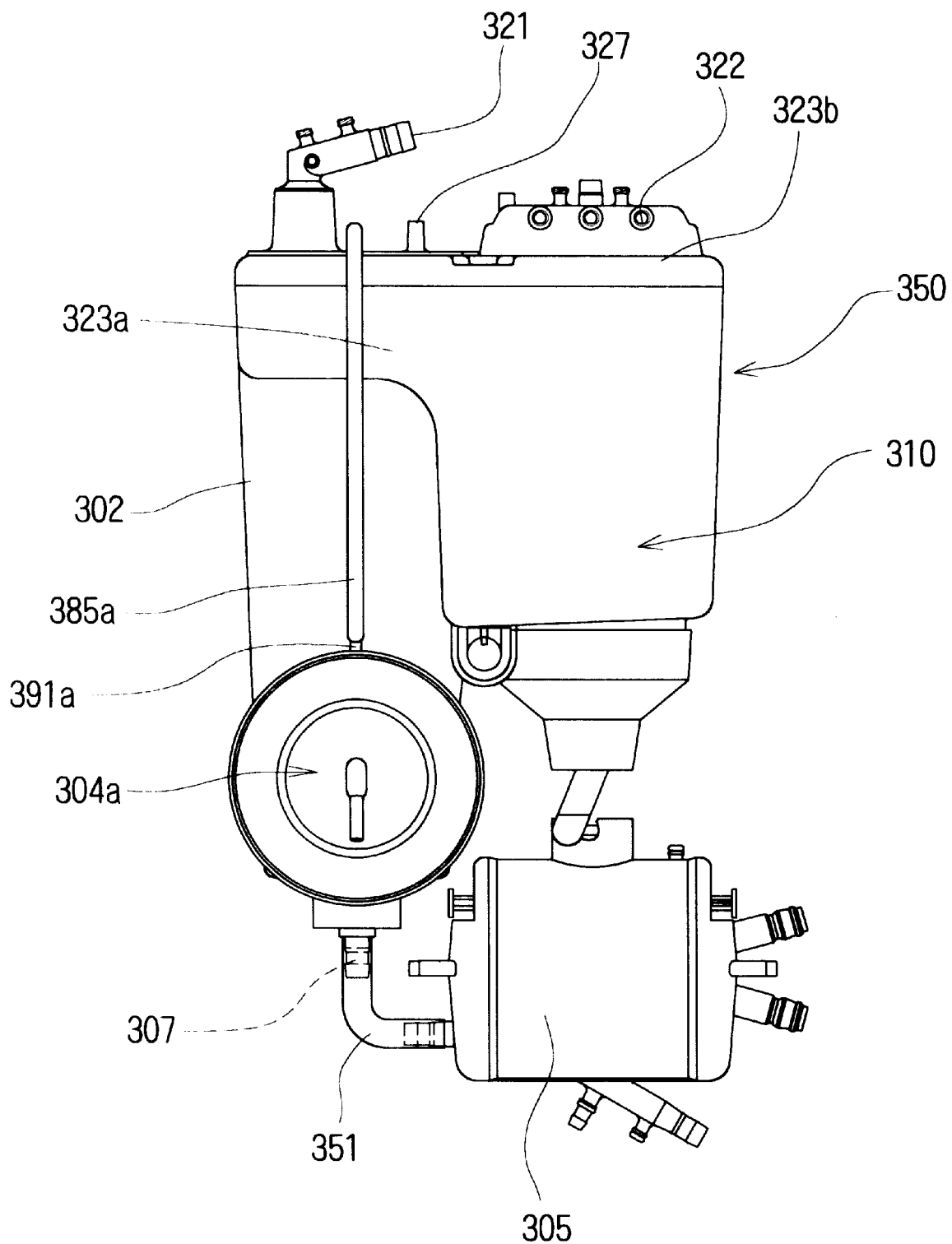
FIG. 51 is a side view of the blood delivery mechanism-equipped blood reservoir tank according to the embodiment, with the artificial lung connected.
Figure 52:
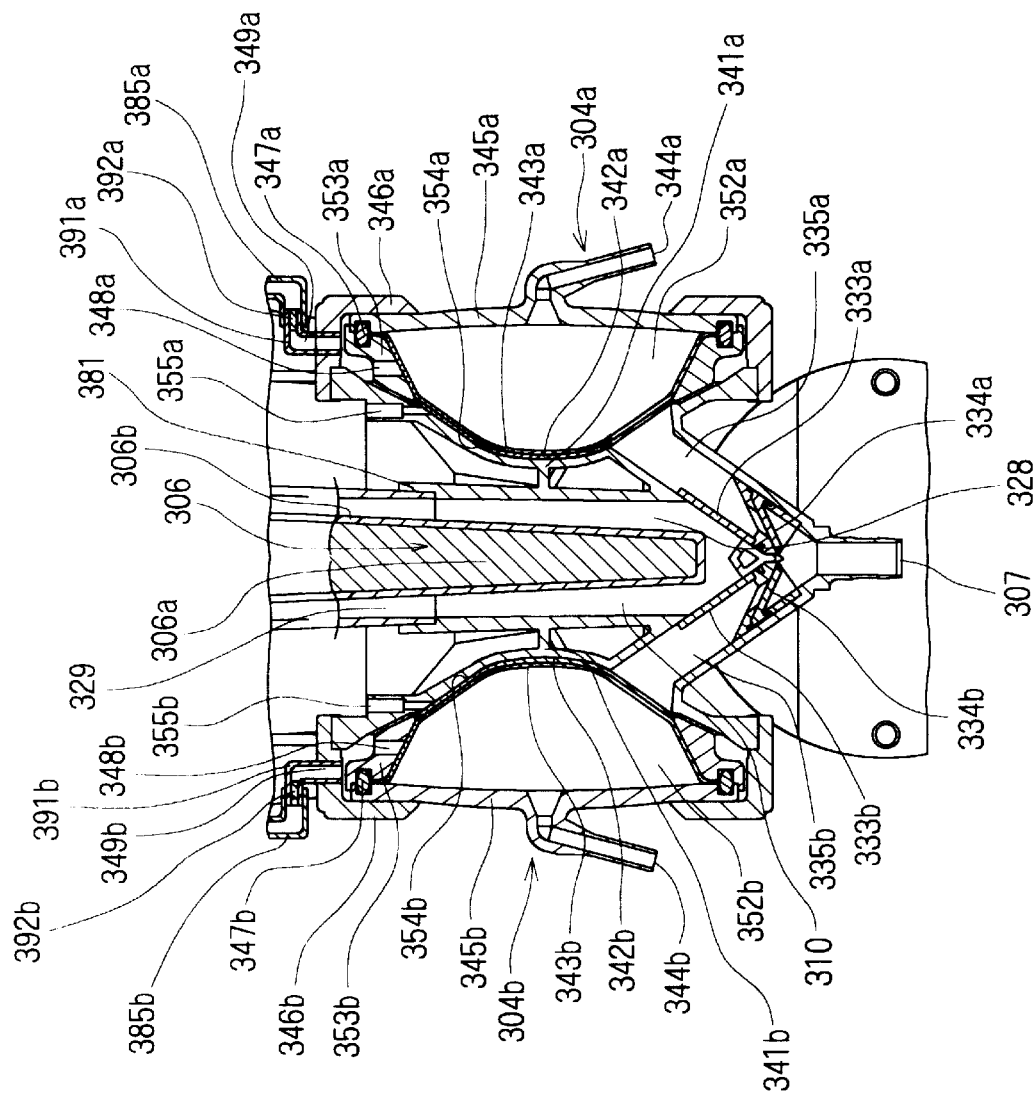
FIG. 52 is an enlarged sectional view of the blood delivery mechanism and a lower portion of a blood storing portion and their surroundings in the blood delivery mechanism-equipped blood reservoir tank shown in FIG. 50, at the time of blood delivery.

In the blood delivery mechanism-equipped blood reservoir tank 350, a lid body 323b has, as shown in FIGS. 50 and 51, a suction device connecting port 382, and communication ports 382a, 382b for connecting to passages that are formed in blood delivering drive units 304a, 304b so as to connect spaces 352a, 352b between the diaphragms and the blood reserving member-pressurizing portions, to the outside. The communication ports 382a, 382b are provided with air-permeable and blood-impermeable members (not shown). The blood-impermeable members may be membrane filters, sintered filters or the like. It is preferred that the pressure loss of the blood-impermeable members be small. The communication ports 382a, 382b may be positioned at any sites where the possibility of contact with blood is small. Although the communication ports 382a, 382b are provided so as to communicate with uppermost end portions of the interior of the blood reservoir tank in FIGS. 50 and 51, this disclosed construction is not restrictive. For example, the communication ports 382a, 382b may also be provided in upper portions of a housing 323a of the blood reservoir tank. Communication members 385a, 385b are connected to the communication ports 382a, 382b, respectively. The communication members 385a, 385b form communication passages connecting passages (openings 349a, 349b) of the blood delivering drive units 304a, 304b to an upper portion of the blood storing portion. The communication members 385a, 385b may be hard or soft tubes.

The portions between the delivery blood reserving members 303a, 303b and the corresponding blood delivering drive units 304a, 304b are air-tightly sealed, except for the passages (openings 348a, 348b and the openings 349a, 349b). Therefore, the spaces 352a, 352b between the delivery blood reserving members 303a, 303b and the blood delivering drive units 304a, 304b communicate with the outside only through those passages.

In this embodiment, communication ports 391a, 391b are connected to the openings 348a, 348b formed in diaphragm retaining annular members 353a, 353b, for communication with the blood storing portion in the blood reservoir tank portion. The communication ports 391a, 391b are in communication with the aforementioned communication ports 382a, 382b through the communication members 385a, 385b. Therefore, the blood storing portion is in communication with the spaces 352a, 352b formed between the delivery blood reserving members 303a, 303b (the diaphragms 342a, 342b) and the blood reserving member-pressurizing portions 343a, 343b.

Lately, the conveyance of blood into the blood reservoir tank and the drainage of blood from a patient are often performed by a method using a suction device (negative pressure applying device) connected to the blood reservoir tank. When this device is operated, the pressure in the blood reservoir tank portion becomes negative, and the negative pressure affects the interiors of delivery blood reserving members. That is, the delivery blood reserving members become exposed to a negative pressure inside due to the operation of the suction device (negative pressure applying device), while receiving the atmospheric pressure on the outside. Therefore, the delivery blood reserving members are pressed by a differential pressure between the inside and outside pressures, so that the liquid surface-sensitive (pressure-sensitive, pre-load-sensitive) function of the delivery blood reserving members may be impeded. However, in the aforementioned construction in which the blood storing portion 310 (blood keeping portion 329 in the blood reservoir tank portion 302) is in communication with the spaces 352a, 352b formed between the delivery blood reserving members 303a, 303b (the diaphragms 342a, 342b) and the blood reserving member-pressurizing portions 343a, 343b through the communication members 385a, 385b, when suction from the blood reservoir tank portion 302 is performed so that the pressure in the blood reservoir tank portion 302 becomes negative, the pressure in the spaces 352a, 352b between the delivery blood reserving members 303a, 303b (the diaphragms 342a, 342b) and the blood reserving member-pressurizing portions 343a, 343b simultaneously becomes negative. This construction thus avoids the impeding of the pre-load-sensitivity performance of the delivery blood reserving members 303a, 303b corresponding to the amount of blood stored in the blood storing portion 310 (the height of liquid surface therein). The positions of the communication ports 391a, 391b, that is, the positions of the passages, may be any positions as long as the ports or passages communicate with the spaces 352a, 352b. The communication ports 391a, 391b may also be provided with air-permeable and blood-impermeable members (not shown). The blood-impermeable members may be membrane filters, sintered filters or the like. It is preferred that the pressure loss of the blood-impermeable members be small.

Where the communication members 385a, 385b are provided, a closed space is formed by the spaces 352a, 352b and the blood storing portion 310. It is expected that the pressure in the closed space will slightly decrease when the blood reserving member-pressurizing portions 343a, 343b contract from the expanded state. However, the pressure in the blood storing portion 310 decreases as the pressure in the spaces 352a, 352b decreases, so that no pressure difference occurs across the diaphragms. Therefore, suction of blood into the delivery blood reserving members 303a, 303b by a reduced pressure will not occur.

In a blood delivery mechanism-equipped blood reservoir tank according to the invention, the lower end of the bubble eliminating member or the bubble removing member is positioned below the lower end of the blood reserving portion of the blood reserving member.

Furthermore, in a blood delivery mechanism-equipped blood reservoir tank according to the invention, the lower end of the bubble eliminating member or the bubble removing member is positioned so as to remain below the blood surface in the blood storing portion even when the blood surface therein lowers to the same height as the lower end of the blood reserving portion of the blood reserving member.

Therefore, even when the amount of blood stored in the blood storing portion decreases to or below a predetermined value so that the blood reserving member functions to reserve amounts of blood proportional to the amount of blood in the blood storing portion, there occurs substantially no bubbling due to flood inflow because the lower end of the bubble eliminating member of the bubble removing member is positioned below the blood surface in the blood storing portion. For the same reason, substantially no or very little bubbling due to blood inflow occurs when the amount of blood in the blood storing portion increases back to or above the predetermined value.

In a blood delivery mechanism-equipped blood reservoir tank according to the invention, the blood reserving member includes a body portion of the blood reserving member which body portion is provided with a concavity surface portion formed from a hard material, and a flexible diaphragm whose peripheral end portion is retained adjacent to a peripheral end portion of the concavity surface portion of the body portion of the blood reserving member so that the peripheral end portion of the diagram is inclined toward a central portion of the concavity surface portion. The blood delivering drive unit includes a blood reserving member-pressurizing portion formed from an expandable sheet material, and a blood delivering fluid flow port for expanding and contracting the blood reserving member-pressurizing portion. The flexible diaphragm is pressed against the concavity surface portion of the body portion of the blood reserving member, without forming any substantial bent point, when the blood reserving member-pressurizing portion is expanded.

Therefore, even when pressed against the concavity surface portion of the blood reserving member body portion, the flexible diaphragm does not form a substantial bent point, that is, does not cause stress concentration at any point therein. Therefore, the incidence of damages to or breakage of the flexible diaphragms is very low despite being repeatedly pressed against the concavity surface portion of the blood reserving member body portion. That is, the diaphragm can be continually used for an extended period.

In a blood delivery mechanism-equipped blood reservoir tank according to the invention, the blood reserving member includes a body portion of the blood reserving member which body portion is formed from a hard material, and a flexible diaphragm whose peripheral portion is retained to the body portion of the blood reserving member. The blood delivering drive unit includes a blood reserving member-pressurizing portion formed from an expandable sheet material, and a blood delivering fluid flow port for expanding and contracting the blood reserving member-pressurizing portion. The blood delivery mechanism-equipped blood reservoir tank further includes a communication passage that connects a space formed between the diaphragm and the blood reserving member-pressurizing portion to the outside.

In this construction, the space formed between the diaphragm and the blood reserving member-pressurizing portion communicates with the outside through the passage; that is, the space formed between the diaphragm and the blood reserving member-pressurizing portion is not a closed space. Therefore, when the blood reserving member-pressurizing portion contacts from an expanded state, this space will not become a pressure-reduced space. Consequently, the function of reserving amounts of blood proportional to the amount of blood stored in the blood storing portion can be reliably performed.

It is preferred that the blood contact surfaces in all the delivery blood storing member-equipped blood reservoir tanks, the blood delivery mechanism-equipped blood reservoir tanks and the blood delivery instruments for an extracorporeal blood circulation circuit described above be non-thrombogenic surfaces. Particularly, the blood contact surfaces of the delivery blood storing members or the delivery blood reserving members, the blood passages, the first check valves and the second check valves are preferred to be non-thrombogenic surfaces.

A non-thrombogenic surface may be formed by subjecting a surface to the coating treatment with a non-thrombogenic material followed by fixation thereof. Examples of the non-thrombogenic material that may suitably be used are heparin, urokinase, HEMA-St-HEMA copolymers, poly-HEMA, and the like.

Preferably, the non-thrombogenic surface is formed by treating a substrate with ozone to form functional group-bearing oxides on the substrate surface and applying heparin to the surface so that an amino group of heparin forms a covalent bond with the functional group directly or through at least one coupling agent. This method allows heparin to be fixed on the blood contact surface without the use of a solvent, thereby minimizing changes of physical properties (e.g., flexibility, elasticity and strength) of the substrate presenting the blood contact surface.

Through ozone treatment, oxides are formed on the substrate surface, containing various functional groups, for example, high reactive functional groups such as aldehyde, ketone, and epoxy groups.

Functional groups of heparin can directly bond with these functional groups. However, such direct bonding method may have problems of steric hindrance and the like. A method wherein a spacer (coupling agent) is introduced to the functional groups prior to fixation of heparin is easy and useful in view of development of the heparin activity. Either a coupling agent or a combination of two or more coupling agents may be used. Compounds having at least two aldehyde or epoxy groups are preferred as coupling agents.

Where two or more coupling agents are used, it is preferred that a coupling agent (spacer coupling agent) of a compound having at least two functional groups, such as amino groups, be first bonded with the functional groups previously formed on the substrate to form amino acid or the like on the substrate, and then heparin be bonded with the substrate using a coupling agent (heparin-fixing coupling agent) of a compound having at least two aldehyde or epoxy groups. In bonding heparin, the coupling agent is preferably introduced into the reaction system simultaneously with or subsequent to introduction of heparin.

If an amino group is introduced using a spacer coupling agent, the amino group exhibits substantially the same reactivity as the amino group of heparin in the reaction system, so that subsequent fixation of heparin to the substrate by the heparin-fixing coupling agent will take place more effectively.

Where the functional group of a coupling agent to directly bond with heparin or the functional group introduced into the substrate is aldehyde group, it is preferable to use heparin in which some N-sulfate groups are desulfurized into primary amino groups.

It is preferred that the spacer coupling agent be one that forms a bond (covalent bond) with the functional group formed on the substrate by ozone treatment and have at least two primary amino groups. Examples of the spacer coupling agent having at least two amino groups include polyethylene imine (PEI), polyethylene glycol diamine, ethylene diamine, and tetramethylene diamine, and the like.

Aldehyde compounds and epoxy compounds are preferable as a coupling agent used for fixing heparin to the substrate. Preferred examples of the aldehyde compounds are glutaraldehyde, glyoxal, succindialdehyde, and the like. Preferred examples of the epoxy compounds are polyethylene glycol diglycidyl ether, 1,4-butanediol-diglycidyl ether, sorbitol diglycidyl ether, glycerol diglycidyl ether, and the like.

Illustrative examples may be: Denacol EX-421, 521, 611, 612, 614, and 614B where the epoxy compound is sorbitol diglycidyl ether; Denacol EX-313 where the diepoxy compound is glycerol diglycidyl ether; Denacol EX-810, 811, 851, 821, 830, 832, 841, and 861 where the diepoxy compound is polyethylene glycol diglycidyl ether, all commercially available from Nagase Chemicals K.K. Denacol EX-313, 421, 512, 521, 810, 811, 821, and 851 are preferred when the difference in epoxy reactivity is considered. In the above-mentioned heparin fixation, the coupling-off of heparin is minimized since the bond between polyethylene imine fixed to the substrate and glutaraldehyde and the bond between glutaraldehyde and heparin are both covalent bonds.

While the present invention has been described with reference to what are presently considered to be preferred embodiments thereof, it is to be understood that the invention is not limited to the disclosed embodiments or constructions. To the contrary, the invention is intended to cover various modifications and equivalent arrangements included within the spirit and scope of the appended claims.

What is claimed is:

1. A delivery blood storing member-equipped blood reservoir tank comprising:

a blood reservoir tank portion; and a delivery blood storing member that communicates with the blood reservoir tank portion for receiving blood from the blood reservoir tank portion, the delivery blood storing member allowing blood to flow out of an interior thereof when pressed from outside, the delivery blood storing member reserving an amount of blood in accordance with a height of liquid surface in the blood reservoir tank portion if an amount of blood in the blood reservoir tank portion becomes equal to or less than a predetermined value, the amount of blood stored in said delivery blood storing member being independent of the pressing, the delivery blood storing member including a body part of the delivery blood storing member which body part is formed from a hard material, and a flexible diaphragm whose peripheral end is fixed to the body part of the delivery blood storing member, the diaphragm producing substantially no self-restoring force against deformation.

2. A delivery blood storing member-equipped blood reservoir tank according to claim 1, wherein the delivery blood storing member further comprises a reinforcement which covers the diaphragm and whose peripheral end is fixed to the body part of the delivery blood storing member.

3. A delivery blood storing member-equipped blood reservoir tank according to claim 2, wherein a pressure needed to deform the diaphragm is equal to or less than 100 mmH$_2$O.

4. A delivery blood storing member-equipped blood reservoir tank according to claim 1, wherein the delivery blood storing member further comprises a reinforcement which covers the diaphragm and whose peripheral end is fixed to the body part of the delivery blood storing member, a second diaphragm which covers the reinforcement and whose peripheral end is fixed to the body part of the delivery blood storing member, and a second reinforcement which covers the second diaphragm and whose peripheral end is fixed to the body part of the delivery blood storing member.

5. A delivery blood storing member-equipped blood reservoir tank according to claim 1, further comprising a first check valve disposed between the blood reservoir tank portion and the delivery blood storing member, the first check valve checking blood flow toward the blood reservoir tank portion, and a second check valve that checks blood flow from a downstream side toward the delivery blood storing member.

6. A delivery blood storing member-equipped blood reservoir tank according to claim 1, further comprising a protective cover housing at least a diaphragm portion of the delivery blood storing member, the protective cover being capable of housing a diaphragm pressing member that is driven when blood is to be sent out of the delivery blood storing member during operation so that the diaphragm pressing member presses a diaphragm side of the delivery blood storing member.

7. A delivery blood storing member-equipped blood reservoir tank according to claim 1, further comprising a diaphragm pressing member that is driven when blood is to be sent out of the delivery blood storing member during operation so that the diaphragm pressing member presses a diaphragm side of the delivery blood storing member, and a protective case housing at least a diaphragm portion of the delivery blood storing member.

8. A delivery blood storing member-equipped blood reservoir tank according to claim 1, wherein at least two sets of the delivery blood storing members are provided.

9. A delivery blood storing member-equipped blood reservoir tank comprising:
a blood reservoir tank portion; and
a delivery blood storing member that communicates with the blood reservoir tank portion for receiving blood from the blood reservoir tank portion, the delivery blood storing member allowing blood to flow out of an interior thereof when pressed from outside, the delivery blood storing member reserving an amount of blood in accordance with a height of liquid surface in the blood reservoir tank portion if an amount of blood in the blood reservoir tank portion becomes equal to or less than a predetermined value, the amount of blood stored in said delivery blood storing member being independent of the pressing,
the delivery blood storing member including
a body part of the delivery blood storing member which body part is formed from a hard material,
a flexible diaphragm whose peripheral end is fixed to the body part of the delivery blood storing member, and
a reinforcement which covers the diaphragm and whose peripheral end is fixed to the body part of the delivery blood storing member.

10. A delivery blood storing member-equipped blood reservoir tank according to claim 9, wherein the delivery blood storing member further comprises a second diaphragm which covers the first diaphragm and whose peripheral end is fixed to the body part of the delivery blood storing member, and a second reinforcement which covers the second diaphragm and whose peripheral end is fixed to the body part of the delivery blood storing member.

11. A delivery blood storing member-equipped blood reservoir tank according to claim 9, further comprising a first check valve disposed between the blood reservoir tank portion and the delivery blood storing member, the first check valve checking blood flow toward the blood reservoir tank portion, and a second check valve that checks blood flow from a downstream side toward the delivery blood storing member.

12. A delivery blood storing member-equipped blood reservoir tank according to claim 9, wherein at least two sets of the delivery blood storing members are provided.

13. A blood delivery instrument for use in an extracorporeal blood circulation circuit, comprising:
a connecting portion to the extracorporeal blood circulation circuit; and
a delivery blood storing member that receives blood from the extracorporeal blood circulation circuit and allows blood to flow out of an interior thereof when pressed from outside, the delivery blood storing member reserving an amount of blood in accordance with a height of liquid surface in a blood reservoir tank provided in the extracorporeal blood circulation circuit or a height of liquid surface in an upstream portion of the blood delivery instrument upstream from the delivery blood storing member, if an amount of blood present in the blood reservoir tank or an amount of blood present in the upstream portion of the blood delivery instrument becomes equal to or less than a predetermined value,
the amount of blood stored in said delivery blood storing member being independent of the pressing, the delivery blood storing member including
a body part of the delivery blood storing member which body part is formed from a hard material, and
a flexible diaphragm whose peripheral end is fixed to the body part of the delivery blood storing member, the diaphragm producing substantially no self-restoring force against deformation.

14. A blood delivery instrument according to claim 13, wherein the delivery blood storing member further comprises a reinforcement which covers the diaphragm and whose peripheral end is fixed to the body part of the delivery blood storing member.

15. A blood delivery instrument according to claim 13, further comprising a diaphragm pressing member that is driven when blood is to be sent out of the delivery blood storing member during operation so that the diaphragm pressing member presses a diaphragm side of the delivery blood storing member, and a protective case housing at least a diaphragm portion of the delivery blood storing member.

16. A blood delivery instrument according to claim 13, wherein the connecting portion to the extracorporeal blood circulation circuit comprises a blood flow inlet port provided at an upper end, and a blood reserving portion extending downward and being capable of reserving a predetermined amount of blood, and wherein the delivery blood storing member reserves an amount of blood in accordance with a height of liquid surface in the blood reserving portion if an amount of blood in the blood reserving portion becomes equal to or less than a predetermined value.

17. A blood delivery instrument according to claim 16, further comprising a first check valve disposed between the blood reserving portion and the delivery blood storing member, the first check valve checking blood flow toward the blood reserving portion, and a second check valve that checks blood flow from a downstream side toward the delivery blood storing member.

18. A blood delivery instrument according to claim 13, further comprising a first check valve disposed between the connecting portion and the delivery blood storing member, the first check valve checking blood flow toward the connecting portion, and a second check valve that checks blood flow from a downstream side toward the delivery blood storing member.

19. A blood delivery instrument for use in an extracorporeal blood circulation circuit, comprising:

a connecting portion to the extracorporeal blood circulation circuit; and a delivery blood storing member that receives blood from the extracorporeal blood circulation circuit and allows blood to flow out of an interior thereof when pressed from outside, the delivery blood storing member reserving an amount of blood in accordance with a height of liquid surface in a blood reservoir tank provided in the extracorporeal blood circulation circuit or a height of liquid surface in an upstream portion of the blood delivery instrument upstream from the delivery blood storing member, if an amount of blood present in the blood reservoir tank or an amount of blood present in the upstream portion of the blood delivery instrument becomes equal to or less than a predetermined value, the amount of blood stored in said delivery blood storing member being independent of the pressing, the delivery blood
storing member including a body part of the delivery blood storing member which body part is formed from a hard material, a flexible diaphragm whose peripheral end is fixed to the body part of the delivery blood storing member, and a reinforcement which covers the diaphragm and whose peripheral end is fixed to the body part of the delivery blood storing member.

20. A blood delivery instrument according to claim 19, wherein the delivery blood storing member further comprises a second diaphragm which covers the reinforcement and whose peripheral end is fixed to the body part of the delivery blood storing member, and a second reinforcement which covers the second diaphragm and whose peripheral end is fixed to the body part of the delivery blood storing member.

21. A blood delivery mechanism-equipped blood reservoir tank comprising:

a blood storing portion;

a blood reserving member including a blood reserving portion that communicates with the blood storing portion, the blood reserving portion reserving an amount of blood proportional to an amount of blood stored in the blood storing portion when the amount of blood stored in the blood storing portion becomes equal to or less than a predetermined value, the blood reserving portion allowing blood to flow out of an interior thereof when pressed from outside, the amount of blood stored in said blood reserving member being independent of the pressing; and at least one of a bubble eliminating member and a bubble removing member that is positioned inside the blood storing portion, a lower end of the at least one of the bubble eliminating member and the bubble removing member being positioned below a lower end of the blood reserving portion of the blood reserving member.

22. A blood delivery mechanism-equipped blood reservoir tank according to claim 21, wherein the at least one of the bubble eliminating member and the bubble removing member extends below an upper portion of the blood storing portion.

23. A blood delivery mechanism-equipped blood reservoir tank according to claim 21, wherein the blood reserving member comprises an air vent port that communicates with an upper end of the blood reserving portion.

24. A blood delivery mechanism-equipped blood reservoir tank according to claim 21, further comprising a blood reserving member-pressurizing portion that operates when blood is to be sent out of the blood reserving member.

25. A blood delivery mechanism-equipped blood reservoir tank according to claim 21, wherein the blood reserving member comprises a deformable portion that is formed from a flexible material and that forms a portion of the blood reserving portion, and wherein the blood delivery mechanism-equipped blood reservoir tank further comprises a blood reserving member-pressurizing portion that deforms the deformable portion at the time of blood delivery so that blood is forced out of an interior of the blood reserving member.

26. A blood delivery mechanism-equipped blood reservoir tank according to claim 21, wherein at least two sets of the blood reserving member and the blood reserving member-pressurizing portion are provided.

27. A blood delivery mechanism-equipped blood reservoir tank according to claim 21, wherein the blood reserving member is a soft material-made tubular body, and the blood reserving member-pressurizing portion is a pump that compresses the soft material-made tubular body to force blood out of an interior of the tubular body.

28. A blood delivery mechanism-equipped blood reservoir tank according to claim 27, further comprising a case member separating the soft material-made tubular body and a pump site that is a portion that compresses the soft material-made tubular body to force blood out of the interior of the tubular body, substantially air-tightly from outside, and a communication passage connecting between an interior of the case member and an upper portion of the blood storing portion.

29. A blood delivery mechanism-equipped blood reservoir tank comprising:

a blood storing portion;

a blood reserving member including a blood reserving portion that communicates with the blood storing portion and receives blood from the blood storing portion, the blood reserving portion reserving an amount of blood proportional to an amount of blood stored in the blood storing portion when the amount of blood stored in the blood storing portion becomes equal to or less than a predetermined value, the blood reserving portion allowing blood to flow out of an interior thereof when pressed from outside, the amount of blood stored in said blood reserving member being independent of the pressing; and at least one of a bubble eliminating member and a bubble removing member that is positioned inside the blood storing portion, a lower end of the at least one of the bubble eliminating member and the bubble removing member being positioned so as to remain below a surface of blood in the blood storing portion even if the surface of blood therein becomes the same level as a lower end of the blood reserving portion of the blood reserving member.

30. A blood reservoir tank equipped with a blood delivery mechanism comprising:

a blood storing portion;

a blood reserving member including a blood reserving portion that communicates with the blood storing portion, the blood reserving portion reserving an amount of blood proportional to an amount of blood stored in the blood storing portion when the amount of blood stored in the blood storing portion becomes equal to or less than a predetermined value, the blood reserving portion allowing blood to flow out of an interior thereof when pressed from outside, the amount of blood stored in said blood reserving member being independent of the pressing; and a blood delivering drive unit that operates when blood is to be sent out of an interior of the blood reserving member, the blood reserving member including a body portion of the blood reserving member which body portion is provided with a concavity surface portion formed from a hard material, and a flexible diaphragm retained liquid-tightly to a peripheral end portion of the concavity surface portion of the body portion of the blood reserving member, and the blood delivering drive unit including a blood reserving member-pressurizing portion formed from an expandable sheet material, and a blood delivering fluid flow port for expanding and contracting the blood reserving member-pressurizing portion, and the flexible diaphragm being pressed against the concavity surface portion of the body portion of the blood reserving member, without forming any substantial bent point, when the blood reserving member-pressurizing portion is expanded.

31. A blood delivery mechanism-equipped blood reservoir tank according to claim 30, wherein the blood reserving member comprises an annular member that holds the diaphragm, a surface of the diaphragm holding annular member closer to the body portion of the blood reserving member is an inclined surface inclined toward a central portion of the concavity surface portion corresponding to a shape of a peripheral end-adjacent portion of the concavity surface portion of the body portion of the blood reserving member, and wherein a peripheral end of the diaphragm is held in such a manner that the peripheral end of the diagram is pressed between the body portion of the blood reserving member and the diaphragm holding annular member.

32. A blood delivery mechanism-equipped blood reservoir tank according to claim 30, further comprising a header provided with the blood delivering fluid flow port, the header and the diaphragm holding annular member sandwiching a peripheral end portion of the blood reserving member-pressurizing portion therebetween, the header and the diaphragm holding annular member allowing a blood delivering fluid to be injected therebetween.

33. A blood delivery mechanism-equipped blood reservoir tank according to claim 30, further comprising a communication passage that connects a space formed between the diaphragm and the blood reserving member-pressurizing portion to the outside.

34. A blood delivery mechanism-equipped blood reservoir tank according to claim 30, wherein the blood reserving member comprises an air vent port communicating with an upper end of the blood reserving portion.

35. A blood delivery mechanism-equipped blood reservoir tank according to claim 30, wherein the diaphragm produces substantially no self-restoring force against deformation.

36. A blood delivery mechanism-equipped blood reservoir tank according to claim 30, wherein the blood reserving member comprises a reinforcement which covers the diaphragm and whose peripheral end is fixed to the body portion of the blood reserving member.

37. A blood reservoir tank equipped with a blood delivery mechanism comprising:

a blood storing portion;

a blood reserving member including a blood reserving portion that communicates with the blood storing portion, the blood reserving portion reserving an amount of blood proportional to an amount of blood stored in the blood storing portion when the amount of blood stored in the blood storing portion becomes equal to or less than a predetermined value, the blood reserving portion allowing blood to flow out of an interior thereof when pressed from outside, the amount of blood stored in said blood reserving member being independent of the pressing; and a blood delivering drive unit that operates when blood is to be sent out of an interior of the blood reserving member, the blood reserving member including a body portion of the blood reserving member which body portion is formed from a hard material, and a flexible diaphragm whose peripheral portion is retained to the body portion of the blood reserving member, the blood delivering drive unit including a blood reserving member-pressurizing portion formed from an expandable sheet material, and a blood delivering fluid flow port for expanding and contracting the blood reserving member-pressurizing portion, and a communication passage connecting a space formed between the diaphragm and the blood reserving member-pressurizing portion to the outside.

38. A blood reservoir tank equipped with a blood delivery mechanism comprising:

a blood storing portion;

a blood reserving member including a blood reserving portion that communicates with the blood storing portion, the blood reserving portion reserving an amount of blood proportional to an amount of blood stored in the blood storing portion when the amount of blood stored in the blood storing portion becomes equal to or less than a predetermined value, the blood reserving portion allowing blood to flow out of an interior thereof when pressed from outside, the amount of blood stored in said blood reserving member being independent of the pressing; and a blood delivering drive unit that operates when blood is to be sent out of an interior of the blood reserving member, the blood reserving member including a body portion of the blood reserving member which body portion is formed from a hard material, and a flexible diaphragm whose peripheral portion is retained to the body portion of the blood reserving member, the blood delivering drive unit including a blood reserving member-pressurizing portion formed from an expandable sheet material, and a blood delivering fluid flow port for expanding and contracting the blood reserving member-pressurizing portion, and a communication passage connecting a space formed between the diaphragm and the blood reserving member-pressurizing portion to an upper portion of the blood storing portion.

39. A blood delivery mechanism-equipped blood reservoir tank according to claim 38, wherein the blood reserving member comprises an air vent port that communicates with an upper end of the blood reserving portion.

40. A blood delivery mechanism-equipped blood reservoir tank comprising:

a blood storing portion;

a blood reserving member including a blood reserving portion that communicates with the blood storing portion, the blood reserving portion reserving an amount of blood proportional to an amount of blood stored in the blood storing portion when the amount of blood stored in the blood storing portion becomes equal to or less than a predetermined value, the blood reserving portion allowing blood to flow out of an interior thereof when pressed from outside, the amount of blood stored in said blood reserving member being independent of the pressing; and a blood reserving member-pressurizing portion that operates when blood is to be sent out of the blood reserving member, the blood reserving member being a soft material-made tubular body, the blood reserving member-pressurizing portion being a pump that compresses the soft material-made tubular body to force blood out of an interior of the tubular body, a case member separating the soft material-made tubular body and a pump site that is a portion that compresses the soft material-made tubular body to force blood out of the interior of the tubular body, substantially airtightly from the outside; and a communication passage connecting an interior of the case member to an upper portion of the blood storing portion.

41. A delivery blood storing member-equipped blood reservoir tank according to claim 1, wherein a pressure needed to deform the diaphragm is equal to or less than 100 mmH$_2$O.

* * * * *

UNITED STATES PATENT AND TRADEMARK OFFICE
CERTIFICATE OF CORRECTION

PATENT NO. : 6,123,519
DATED : September 26, 2000
INVENTOR(S) : Y. KATO, et al.

It is certified that error appears in the above-identified patent and that said Letters Patent is hereby corrected as shown below:

On the Title Page, Item

[56] References Cited

U.S. PATENT DOCUMENTS

Fourth listed patent is corrected to read:

4,552,552    1/1994    Polaschegg et al. ............ 604/4

Column 49, line 27, delete "mmII$_2$0" and insert --mmH$_2$0--

Signed and Sealed this

Fifteenth Day of May, 2001

*Attest:*

NICHOLAS P. GODICI

*Attesting Officer*    *Acting Director of the United States Patent and Trademark Office*